US008394947B2

(12) United States Patent
Bhat et al.

(10) Patent No.: US 8,394,947 B2
(45) Date of Patent: Mar. 12, 2013

(54) POSITIONALLY MODIFIED SIRNA CONSTRUCTS

(75) Inventors: Balkrishen Bhat, Carlsbad, CA (US); Eric E. Swayze, Carlsbad, CA (US); Thazha P. Prakash, Carlsbad, CA (US); Charles Allerson, San Diego, CA (US); Prasad Dande, Cambridge, MA (US); Richard H. Griffey, Vista, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 796 days.

(21) Appl. No.: 11/569,939

(22) PCT Filed: Mar. 3, 2004

(86) PCT No.: PCT/US2004/017485
§ 371 (c)(1),
(2), (4) Date: Dec. 3, 2007

(87) PCT Pub. No.: WO2005/120230
PCT Pub. Date: Dec. 22, 2005

(65) Prior Publication Data
US 2008/0146788 A1    Jun. 19, 2008

(51) Int. Cl.
*C07H 21/02* (2006.01)
*C07H 21/04* (2006.01)
*A61K 31/70* (2006.01)
*C12Q 1/68* (2006.01)

(52) U.S. Cl. ............... 536/24.5; 536/23.1; 536/24.1; 435/6; 514/44

(58) Field of Classification Search .................. None
See application file for complete search history.

(56) References Cited

U.S. PATENT DOCUMENTS

| | | |
|---|---|---|
| 3,687,808 A | 8/1972 | Merigan, Jr. et al. |
| 4,373,071 A | 2/1983 | Itakura |
| 4,381,344 A | 4/1983 | Rideout et al. |
| 4,401,796 A | 8/1983 | Itakura |
| 4,415,732 A | 11/1983 | Caruthers et al. |
| 4,426,330 A | 1/1984 | Sears |
| 4,458,066 A | 7/1984 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,507,433 A | 3/1985 | Miller et al. |
| 4,511,713 A | 4/1985 | Miller et al. |
| 4,534,899 A | 8/1985 | Sears |
| 4,587,044 A | 5/1986 | Miller et al. |
| 4,605,735 A | 8/1986 | Miyoshi et al. |
| 4,667,025 A | 5/1987 | Miyoshi et al. |
| 4,668,777 A | 5/1987 | Caruthers et al. |
| 4,689,320 A | 8/1987 | Kaji |
| 4,720,483 A | 1/1988 | Jansz et al. |
| 4,725,677 A | 2/1988 | Koster et al. |
| 4,757,141 A | 7/1988 | Fung et al. |
| 4,760,017 A | 7/1988 | McCormick |
| 4,762,779 A | 8/1988 | Snitman |
| 4,789,737 A | 12/1988 | Miyoshi et al. |
| 4,812,512 A | 3/1989 | Buendia et al. |
| 4,824,941 A | 4/1989 | Gordon et al. |
| 4,828,979 A | 5/1989 | Klevan et al. |
| 4,835,263 A | 5/1989 | Nguyen et al. |
| 4,845,205 A | 7/1989 | Huynh Dinh et al. |
| 4,849,320 A | 7/1989 | Irving et al. |
| 4,849,513 A | 7/1989 | Smith et al. |
| 4,876,335 A | 10/1989 | Yamane et al. |
| 4,904,582 A | 2/1990 | Tullis |
| 4,908,405 A | 3/1990 | Bayer et al. |
| 4,924,624 A | 5/1990 | Suhadolnik et al. |
| 4,948,882 A | 8/1990 | Ruth |
| 4,958,013 A | 9/1990 | Letsinger |
| 4,965,350 A | 10/1990 | Inoue et al. |
| 4,973,679 A | 11/1990 | Caruthers et al. |
| 4,981,957 A | 1/1991 | Lebleu et al. |
| 5,000,000 A | 3/1991 | Ingram et al. |
| 5,013,556 A | 5/1991 | Woodle et al. |
| 5,013,830 A | 5/1991 | Ohtsuka et al. |
| 5,023,243 A | 6/1991 | Tullis |
| 5,034,506 A | 7/1991 | Summerton et al. |
| 5,082,830 A | 1/1992 | Brakel et al. |
| 5,082,934 A | 1/1992 | Saba et al. |
| 5,108,921 A | 4/1992 | Low et al. |
| 5,109,124 A | 4/1992 | Ramachandran et al. |
| 5,112,963 A | 5/1992 | Pieles et al. |
| 5,118,800 A | 6/1992 | Smith et al. |
| 5,118,802 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| 5,138,045 A | 8/1992 | Cook et al. |
| 5,142,047 A | 8/1992 | Summerton et al. |
| RE34,069 E | 9/1992 | Koster et al. |
| 5,149,782 A | 9/1992 | Chang et al. |
| 5,149,797 A | 9/1992 | Pederson et al. |
| 5,151,510 A | 9/1992 | Stec et al. |

(Continued)

FOREIGN PATENT DOCUMENTS

| | | |
|---|---|---|
| CA | 2017369 C | 1/2001 |
| DE | 3915432 A1 | 11/1990 |

(Continued)

OTHER PUBLICATIONS

Damha, M.J. et al., "Hybrids of RNA and Arabinonucleic acids (ANA and 2' F-ANA) are substrates of Ribonuclease H," J. Am Chem. Soc., 1998, 120, 12976-12977.

(Continued)

*Primary Examiner* — Jennifer Pitrak McDonald
(74) *Attorney, Agent, or Firm* — Woodcock Washburn LLP

(57) ABSTRACT

The present invention provides oligomeric compounds having sufficient complementarity to hybridize to a nucleic acid target and methods for their use in modulating gene expression. In one embodiment the oligomeric compounds comprise double stranded constructs wherein one of the strands capable of hybridizing to a nucleic acid target, and has a plurality of modified ribofuranosyl nucleosides at defined locations. The presence of modifications at such defined positions greatly enhances the properties of the corresponding compositions.

15 Claims, 3 Drawing Sheets

U.S. PATENT DOCUMENTS

| | | |
|---|---|---|
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,177,198 A | 1/1993 | Spielvogel et al. |
| 5,185,444 A | 2/1993 | Summerton et al. |
| 5,188,897 A | 2/1993 | Suhadolnik et al. |
| 5,194,599 A | 3/1993 | Froehler et al. |
| 5,212,295 A | 5/1993 | Cook |
| 5,213,804 A | 5/1993 | Martin et al. |
| 5,214,134 A | 5/1993 | Weis et al. |
| 5,214,135 A | 5/1993 | Srivastava et al. |
| 5,214,136 A | 5/1993 | Lin et al. |
| 5,216,141 A | 6/1993 | Benner |
| 5,218,105 A | 6/1993 | Cook et al. |
| 5,220,007 A | 6/1993 | Pederson et al. |
| 5,223,618 A | 6/1993 | Cook et al. |
| 5,227,170 A | 7/1993 | Sullivan |
| 5,235,033 A | 8/1993 | Summerton et al. |
| 5,245,022 A | 9/1993 | Weis et al. |
| 5,254,469 A | 10/1993 | Warren, III et al. |
| 5,256,775 A | 10/1993 | Froehler |
| 5,258,506 A | 11/1993 | Urdea et al. |
| 5,262,536 A | 11/1993 | Hobbs, Jr. |
| 5,264,221 A | 11/1993 | Tagawa et al. |
| 5,264,423 A | 11/1993 | Cohen et al. |
| 5,264,562 A | 11/1993 | Matteucci |
| 5,264,564 A | 11/1993 | Matteucci |
| 5,272,250 A | 12/1993 | Spielvogel et al. |
| 5,276,019 A | 1/1994 | Cohen et al. |
| 5,278,302 A | 1/1994 | Caruthers et al. |
| 5,286,717 A | 2/1994 | Cohen et al. |
| 5,292,873 A | 3/1994 | Rokita et al. |
| 5,317,098 A | 5/1994 | Shizuya et al. |
| 5,319,080 A | 6/1994 | Leumann |
| 5,321,131 A | 6/1994 | Agrawal et al. |
| 5,354,844 A | 10/1994 | Beug et al. |
| 5,356,633 A | 10/1994 | Woodle et al. |
| 5,359,044 A | 10/1994 | Cook et al. |
| 5,366,878 A | 11/1994 | Pederson et al. |
| 5,367,066 A | 11/1994 | Urdea et al. |
| 5,371,241 A | 12/1994 | Brush |
| 5,378,825 A | 1/1995 | Cook et al. |
| 5,386,023 A | 1/1995 | Sanghvi et al. |
| 5,391,723 A | 2/1995 | Priest |
| 5,393,878 A | 2/1995 | Leumann |
| 5,395,619 A | 3/1995 | Zalipsky et al. |
| 5,399,676 A | 3/1995 | Froehler |
| 5,403,711 A | 4/1995 | Walder et al. |
| 5,405,938 A | 4/1995 | Summerton et al. |
| 5,405,939 A | 4/1995 | Suhadolnik et al. |
| 5,414,077 A | 5/1995 | Lin et al. |
| 5,416,016 A | 5/1995 | Low et al. |
| 5,416,203 A | 5/1995 | Letsinger |
| 5,417,978 A | 5/1995 | Tari et al. |
| 5,432,272 A | 7/1995 | Benner |
| 5,434,257 A | 7/1995 | Matteucci et al. |
| 5,446,137 A | 8/1995 | Maag et al. |
| 5,451,463 A | 9/1995 | Nelson et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,457,191 A | 10/1995 | Cook et al. |
| 5,459,127 A | 10/1995 | Felgner et al. |
| 5,459,255 A | 10/1995 | Cook et al. |
| 5,462,854 A | 10/1995 | Coassin et al. |
| 5,466,677 A | 11/1995 | Baxter et al. |
| 5,466,786 A | 11/1995 | Buhr et al. |
| 5,469,854 A | 11/1995 | Unger et al. |
| 5,470,967 A | 11/1995 | Huie et al. |
| 5,476,925 A | 12/1995 | Letsinger et al. |
| 5,484,908 A | 1/1996 | Froehler et al. |
| 5,486,603 A | 1/1996 | Buhr |
| 5,489,677 A | 2/1996 | Sanghvi et al. |
| 5,491,133 A | 2/1996 | Walder et al. |
| 5,502,177 A | 3/1996 | Matteucci et al. |
| 5,506,212 A | 4/1996 | Hoke et al. |
| 5,506,337 A | 4/1996 | Summerton et al. |
| 5,506,351 A | 4/1996 | McGee |
| 5,510,475 A | 4/1996 | Agrawal et al. |
| 5,512,295 A | 4/1996 | Kornberg et al. |
| 5,512,439 A | 4/1996 | Hornes et al. |
| 5,512,667 A | 4/1996 | Reed et al. |
| 5,514,785 A | 5/1996 | Van Ness et al. |
| 5,514,786 A | 5/1996 | Cook et al. |
| 5,519,126 A | 5/1996 | Hecht |
| 5,519,134 A | 5/1996 | Acevedo et al. |
| 5,521,291 A | 5/1996 | Curiel et al. |
| 5,525,465 A | 6/1996 | Haralambidis et al. |
| 5,525,711 A | 6/1996 | Hawkins et al. |
| 5,527,528 A | 6/1996 | Allen et al. |
| 5,527,899 A | 6/1996 | Froehler |
| 5,532,130 A | 7/1996 | Alul |
| 5,534,259 A | 7/1996 | Zalipsky et al. |
| 5,536,821 A | 7/1996 | Agrawal et al. |
| 5,539,082 A | 7/1996 | Nielsen et al. |
| 5,539,083 A | 7/1996 | Cook et al. |
| 5,541,306 A | 7/1996 | Agrawal et al. |
| 5,541,307 A | 7/1996 | Cook et al. |
| 5,541,313 A | 7/1996 | Ruth |
| 5,543,152 A | 8/1996 | Webb et al. |
| 5,543,158 A | 8/1996 | Gref et al. |
| 5,545,730 A | 8/1996 | Urdea et al. |
| 5,547,932 A | 8/1996 | Curiel et al. |
| 5,550,111 A | 8/1996 | Suhadolnik et al. |
| 5,552,538 A | 9/1996 | Urdea et al. |
| 5,552,540 A | 9/1996 | Haralambidis |
| 5,556,948 A | 9/1996 | Tagawa et al. |
| 5,561,043 A | 10/1996 | Cantor et al. |
| 5,561,225 A | 10/1996 | Maddry et al. |
| 5,563,253 A | 10/1996 | Agrawal et al. |
| 5,565,350 A | 10/1996 | Kmiec |
| 5,565,552 A | 10/1996 | Magda et al. |
| 5,565,555 A | 10/1996 | Froehler et al. |
| 5,567,810 A | 10/1996 | Weis et al. |
| 5,567,811 A | 10/1996 | Misiura et al. |
| 5,571,799 A | 11/1996 | Tkachuk et al. |
| 5,574,142 A | 11/1996 | Meyer, Jr. et al. |
| 5,576,302 A | 11/1996 | Cook et al. |
| 5,576,427 A | 11/1996 | Cook et al. |
| 5,578,717 A | 11/1996 | Urdea et al. |
| 5,578,718 A | 11/1996 | Cook et al. |
| 5,580,575 A | 12/1996 | Unger et al. |
| 5,580,731 A | 12/1996 | Chang et al. |
| 5,582,188 A | 12/1996 | Benderev et al. |
| 5,583,020 A | 12/1996 | Sullivan |
| 5,585,481 A | 12/1996 | Arnold, Jr. et al. |
| 5,587,361 A | 12/1996 | Cook et al. |
| 5,587,371 A | 12/1996 | Sessler et al. |
| 5,587,469 A | 12/1996 | Cook et al. |
| 5,591,584 A | 1/1997 | Chang et al. |
| 5,591,721 A | 1/1997 | Agrawal et al. |
| 5,591,722 A | 1/1997 | Montgomery et al. |
| 5,594,121 A | 1/1997 | Froehler et al. |
| 5,595,726 A | 1/1997 | Magda et al. |
| 5,595,756 A | 1/1997 | Bally et al. |
| 5,596,086 A | 1/1997 | Matteucci et al. |
| 5,596,091 A | 1/1997 | Switzer |
| 5,597,696 A | 1/1997 | Linn et al. |
| 5,597,909 A | 1/1997 | Urdea et al. |
| 5,599,797 A | 2/1997 | Cook et al. |
| 5,599,923 A | 2/1997 | Sessler et al. |
| 5,599,925 A | 2/1997 | Torii |
| 5,599,928 A | 2/1997 | Hemmi et al. |
| 5,602,240 A | 2/1997 | De Mesmaeker et al. |
| 5,607,922 A | 3/1997 | De Clercq et al. |
| 5,607,923 A | 3/1997 | Cook et al. |
| 5,608,046 A | 3/1997 | Cook et al. |
| 5,610,289 A | 3/1997 | Cook et al. |
| 5,610,300 A | 3/1997 | Altmann et al. |
| 5,612,469 A | 3/1997 | Goodchild |
| 5,614,617 A | 3/1997 | Cook et al. |
| 5,614,621 A | 3/1997 | Ravikumar et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |

| Patent | Date | Inventor |
|---|---|---|
| 5,631,148 A | 5/1997 | Urdea |
| 5,633,360 A | 5/1997 | Bischofberger et al. |
| 5,634,488 A | 6/1997 | Martin, Jr. |
| 5,635,488 A | 6/1997 | Cook et al. |
| 5,639,647 A | 6/1997 | Usman et al. |
| 5,639,873 A | 6/1997 | Barascut et al. |
| 5,643,889 A | 7/1997 | Suhadolnik et al. |
| 5,645,985 A | 7/1997 | Froehler et al. |
| 5,646,265 A | 7/1997 | McGee |
| 5,646,269 A | 7/1997 | Matteucci et al. |
| 5,652,355 A | 7/1997 | Metelev et al. |
| 5,652,356 A | 7/1997 | Agrawal |
| 5,658,731 A | 8/1997 | Sproat et al. |
| 5,658,873 A | 8/1997 | Bertsch-Frank et al. |
| 5,661,134 A | 8/1997 | Cook et al. |
| 5,663,312 A | 9/1997 | Chaturvedula |
| 5,663,360 A | 9/1997 | Bortolaso et al. |
| 5,670,633 A | 9/1997 | Cook et al. |
| 5,672,662 A | 9/1997 | Harris et al. |
| 5,672,695 A | 9/1997 | Eckstein et al. |
| 5,672,697 A | 9/1997 | Buhr et al. |
| 5,677,289 A | 10/1997 | Torrence et al. |
| 5,677,437 A | 10/1997 | Teng et al. |
| 5,677,439 A | 10/1997 | Weis et al. |
| 5,681,940 A | 10/1997 | Wang et al. |
| 5,681,941 A | 10/1997 | Cook et al. |
| 5,684,142 A | 11/1997 | Mishra et al. |
| 5,684,143 A | 11/1997 | Gryaznov et al. |
| 5,684,243 A | 11/1997 | Gururaja et al. |
| 5,688,941 A | 11/1997 | Cook et al. |
| 5,698,687 A | 12/1997 | Eckstein et al. |
| 5,700,785 A | 12/1997 | Suhadolnik et al. |
| 5,700,920 A | 12/1997 | Altmann et al. |
| 5,700,922 A | 12/1997 | Cook |
| 5,714,166 A | 2/1998 | Tomalia et al. |
| 5,714,331 A | 2/1998 | Buchardt et al. |
| 5,716,824 A | 2/1998 | Beigelman et al. |
| 5,719,262 A | 2/1998 | Buchardt et al. |
| 5,719,271 A | 2/1998 | Cook et al. |
| 5,721,218 A | 2/1998 | Froehler |
| 5,726,297 A | 3/1998 | Gryaznov et al. |
| 5,750,666 A | 5/1998 | Caruthers et al. |
| 5,750,669 A | 5/1998 | Rosch et al. |
| 5,750,692 A | 5/1998 | Cook et al. |
| 5,760,202 A | 6/1998 | Cook et al. |
| 5,760,209 A | 6/1998 | Cheruvallath et al. |
| 5,763,588 A | 6/1998 | Matteucci et al. |
| 5,770,713 A | 6/1998 | Imbach et al. |
| 5,770,716 A | 6/1998 | Khan et al. |
| 5,777,092 A | 7/1998 | Cook et al. |
| 5,780,607 A | 7/1998 | Goodnow, Jr. et al. |
| 5,789,576 A | 8/1998 | Daily et al. |
| 5,792,608 A | 8/1998 | Swaminathan et al. |
| 5,792,747 A | 8/1998 | Schally et al. |
| 5,792,844 A | 8/1998 | Sanghvi et al. |
| 5,792,847 A | 8/1998 | Buhr et al. |
| 5,801,154 A | 9/1998 | Baracchini et al. |
| 5,808,023 A | 9/1998 | Sanghvi et al. |
| 5,808,036 A | 9/1998 | Kool |
| 5,817,781 A | 10/1998 | Swaminathan et al. |
| 5,830,635 A | 11/1998 | Agnello |
| 5,830,653 A | 11/1998 | Froehler et al. |
| 5,837,835 A | 11/1998 | Gryaznov et al. |
| 5,837,852 A | 11/1998 | Chung et al. |
| 5,840,876 A | 11/1998 | Beigelman et al. |
| 5,854,410 A | 12/1998 | Arnold, Jr. et al. |
| 5,859,221 A | 1/1999 | Cook et al. |
| 5,861,493 A | 1/1999 | Cook et al. |
| 5,872,232 A | 2/1999 | Cook et al. |
| 5,874,553 A | 2/1999 | Peyman et al. |
| 5,891,683 A | 4/1999 | Usman et al. |
| 5,891,684 A | 4/1999 | Usman et al. |
| 5,898,031 A | 4/1999 | Crooke |
| 5,914,396 A | 6/1999 | Cook et al. |
| 5,936,080 A | 8/1999 | Stec et al. |
| 5,945,521 A | 8/1999 | Just et al. |
| 5,955,443 A | 9/1999 | Bennett et al. |
| 5,962,425 A | 10/1999 | Walder et al. |
| 5,965,720 A | 10/1999 | Gryaznov et al. |
| 5,965,721 A | 10/1999 | Cook et al. |
| 5,969,116 A | 10/1999 | Martin |
| 5,969,118 A | 10/1999 | Sanghvi et al. |
| 5,986,083 A | 11/1999 | Dwyer et al. |
| 5,998,203 A | 12/1999 | Matulic-Adamic et al. |
| 5,998,588 A | 12/1999 | Hoffman et al. |
| 6,001,841 A | 12/1999 | Cook et al. |
| 6,005,087 A | 12/1999 | Cook et al. |
| 6,005,094 A | 12/1999 | Simon et al. |
| 6,005,096 A | 12/1999 | Matteucci et al. |
| 6,007,992 A | 12/1999 | Lin et al. |
| 6,013,785 A | 1/2000 | Bruice et al. |
| 6,015,886 A | 1/2000 | Dale et al. |
| 6,020,475 A | 2/2000 | Capaldi et al. |
| 6,025,140 A | 2/2000 | Langel et al. |
| 6,028,183 A | 2/2000 | Lin et al. |
| 6,028,188 A | 2/2000 | Arnold, Jr. et al. |
| 6,033,910 A | 3/2000 | Monia et al. |
| 6,037,463 A | 3/2000 | Uhlmann et al. |
| 6,043,060 A | 3/2000 | Imanishi |
| 6,043,352 A | 3/2000 | Manoharan et al. |
| 6,046,306 A | 4/2000 | Breipohl et al. |
| 6,051,699 A | 4/2000 | Ravikumar |
| 6,087,484 A | 7/2000 | Goodchild |
| 6,096,875 A | 8/2000 | Khan et al. |
| 6,107,094 A * | 8/2000 | Crooke ......................... 435/455 |
| 6,111,085 A | 8/2000 | Cook et al. |
| 6,117,657 A | 9/2000 | Usman et al. |
| 6,121,437 A | 9/2000 | Guzaev et al. |
| 6,127,346 A | 10/2000 | Peyman et al. |
| 6,127,533 A | 10/2000 | Cook et al. |
| 6,133,246 A | 10/2000 | McKay et al. |
| 6,147,200 A | 11/2000 | Manoharan et al. |
| 6,150,510 A | 11/2000 | Seela et al. |
| 6,153,737 A | 11/2000 | Manoharan et al. |
| 6,166,188 A | 12/2000 | Cook et al. |
| 6,169,177 B1 | 1/2001 | Manoharan |
| 6,172,208 B1 | 1/2001 | Cook |
| 6,172,209 B1 | 1/2001 | Manoharan et al. |
| 6,172,216 B1 | 1/2001 | Bennett et al. |
| 6,207,646 B1 | 3/2001 | Krieg et al. |
| 6,210,892 B1 | 4/2001 | Bennett et al. |
| 6,220,025 B1 | 4/2001 | Mauti et al. |
| 6,222,025 B1 | 4/2001 | Cook et al. |
| 6,227,982 B1 | 5/2001 | Wurster |
| 6,239,265 B1 | 5/2001 | Cook |
| 6,239,272 B1 | 5/2001 | Beigelman et al. |
| 6,262,036 B1 | 7/2001 | Arnold, Jr. et al. |
| 6,262,241 B1 | 7/2001 | Cook et al. |
| 6,268,490 B1 | 7/2001 | Imanishi et al. |
| 6,271,358 B1 | 8/2001 | Manoharan et al. |
| 6,274,723 B1 | 8/2001 | Nilsen |
| 6,277,634 B1 | 8/2001 | McCall et al. |
| 6,277,967 B1 | 8/2001 | Manoharan |
| 6,281,201 B1 | 8/2001 | Suhadolnik et al. |
| 6,284,538 B1 | 9/2001 | Monia et al. |
| 6,287,860 B1 | 9/2001 | Monia et al. |
| 6,294,522 B1 | 9/2001 | Zablocki et al. |
| 6,300,319 B1 | 10/2001 | Manoharan |
| 6,307,040 B1 | 10/2001 | Cook et al. |
| 6,326,358 B1 | 12/2001 | Manoharan |
| 6,326,478 B1 | 12/2001 | Cheruvallath et al. |
| 6,329,346 B1 | 12/2001 | Muhlegger et al. |
| 6,331,617 B1 | 12/2001 | Weeks et al. |
| 6,335,432 B1 | 1/2002 | Segev |
| 6,335,434 B1 | 1/2002 | Guzaev et al. |
| 6,335,437 B1 | 1/2002 | Manoharan et al. |
| 6,344,436 B1 | 2/2002 | Smith et al. |
| 6,358,931 B1 | 3/2002 | Cook et al. |
| 6,365,379 B1 | 4/2002 | Lima et al. |
| 6,380,169 B1 | 4/2002 | Adams et al. |
| 6,395,437 B1 | 5/2002 | Wollesen |
| 6,395,474 B1 | 5/2002 | Buchardt et al. |
| 6,395,492 B1 | 5/2002 | Manoharan et al. |
| 6,410,702 B1 | 6/2002 | Swaminathan et al. |
| 6,414,127 B1 | 7/2002 | Lin et al. |
| 6,420,549 B1 | 7/2002 | Cook et al. |
| 6,426,220 B1 | 7/2002 | Bennett et al. |
| 6,436,640 B1 | 8/2002 | Simmons et al. |

| | | |
|---|---|---|
| 6,440,943 B1 | 8/2002 | Cook et al. |
| 6,444,806 B1 | 9/2002 | Veerapanani et al. |
| 6,465,628 B1 | 10/2002 | Ravikumar et al. |
| 6,476,205 B1 | 11/2002 | Buhr et al. |
| 6,486,308 B2 | 11/2002 | Kutyavin et al. |
| 6,506,559 B1 | 1/2003 | Fire et al. |
| 6,525,031 B2 | 2/2003 | Manoharan |
| 6,528,631 B1 | 3/2003 | Cook et al. |
| 6,531,584 B1 | 3/2003 | Cook et al. |
| 6,534,639 B1 | 3/2003 | Manoharan et al. |
| 6,559,279 B1 | 5/2003 | Manoharan et al. |
| 6,573,072 B1 | 6/2003 | Goodchild |
| 6,593,466 B1 | 7/2003 | Manoharan et al. |
| 6,656,730 B1 | 12/2003 | Manoharan |
| 6,670,461 B1 | 12/2003 | Wengel et al. |
| 6,673,611 B2 | 1/2004 | Thompson et al. |
| 6,683,167 B2 | 1/2004 | Metelev et al. |
| 6,794,499 B2 | 9/2004 | Wengel et al. |
| 6,818,759 B2 | 11/2004 | Beigelman et al. |
| 6,849,726 B2 | 2/2005 | Usman et al. |
| 6,887,906 B1 | 5/2005 | Teng et al. |
| 7,022,828 B2 | 4/2006 | McSwiggen |
| 2002/0049173 A1 | 4/2002 | Bennett et al. |
| 2002/0068708 A1 | 6/2002 | Wengel et al. |
| 2002/0071826 A1 | 6/2002 | Tamarkin et al. |
| 2002/0081577 A1 | 6/2002 | Kilkuskie et al. |
| 2002/0081736 A1 | 6/2002 | Conroy et al. |
| 2002/0102267 A1 | 8/2002 | Lu et al. |
| 2002/0132788 A1 | 9/2002 | Lewis et al. |
| 2002/0147332 A1 | 10/2002 | Kaneko |
| 2002/0151512 A1 | 10/2002 | Peyman et al. |
| 2002/0156235 A1 | 10/2002 | Manoharan et al. |
| 2002/0160393 A1 | 10/2002 | Symonds et al. |
| 2002/0162126 A1 | 10/2002 | Beach et al. |
| 2002/0165189 A1 | 11/2002 | Crooke |
| 2003/0004325 A1 | 1/2003 | Cook et al. |
| 2003/0027780 A1 | 2/2003 | Hardee et al. |
| 2003/0096286 A1 | 5/2003 | Crooke |
| 2003/0096287 A1 | 5/2003 | Crooke |
| 2003/0096784 A1 | 5/2003 | Crooke |
| 2003/0119777 A1 | 6/2003 | Crooke |
| 2003/0125241 A1 | 7/2003 | Wissenbach et al. |
| 2003/0139585 A1 | 7/2003 | Uhlmann et al. |
| 2003/0143732 A1 | 7/2003 | Fosnaugh et al. |
| 2003/0158403 A1 | 8/2003 | Manoharan et al. |
| 2003/0166282 A1 | 9/2003 | Brown et al. |
| 2003/0175906 A1 | 9/2003 | Manoharan et al. |
| 2003/0187240 A1 | 10/2003 | Cook et al. |
| 2003/0190635 A1 | 10/2003 | McSwiggen |
| 2003/0206887 A1 | 11/2003 | Morrissey et al. |
| 2003/0207804 A1 | 11/2003 | Manoharan et al. |
| 2003/0224377 A1 | 12/2003 | Wengel et al. |
| 2004/0001811 A1 | 1/2004 | Kreutzer et al. |
| 2004/0009938 A1 | 1/2004 | Manoharan et al. |
| 2004/0014957 A1 | 1/2004 | Eldrup et al. |
| 2004/0018999 A1 | 1/2004 | Beach et al. |
| 2004/0029275 A1 | 2/2004 | Brown et al. |
| 2004/0102618 A1 | 5/2004 | Crooke et al. |
| 2004/0146867 A1 | 7/2004 | Slattum et al. |
| 2004/0171033 A1 | 9/2004 | Baker et al. |
| 2004/0180351 A1 | 9/2004 | Giese et al. |
| 2004/0192626 A1 | 9/2004 | McSwiggen et al. |
| 2004/0259247 A1 | 12/2004 | Tuschl et al. |
| 2005/0020521 A1 | 1/2005 | Rana |
| 2005/0020525 A1 | 1/2005 | McSwiggen et al. |
| 2005/0080246 A1 | 4/2005 | Allerson et al. |
| 2005/0142535 A1 | 6/2005 | Damha et al. |
| 2005/0164209 A1 | 7/2005 | Bennett et al. |
| 2005/0181382 A1 | 8/2005 | Zamore et al. |
| 2005/0221275 A1 | 10/2005 | Bennett et al. |
| 2005/0245474 A1 | 11/2005 | Baker et al. |
| 2005/0261218 A1 | 11/2005 | Esau et al. |
| 2005/0273868 A1 | 12/2005 | Rana |
| 2006/0127891 A1 | 6/2006 | McSwiggen et al. |
| 2007/0031844 A1* | 2/2007 | Khvorova et al. ............ 435/6 |
| 2007/0032446 A1 | 2/2007 | Cook et al. |
| 2007/0167384 A1 | 7/2007 | Leake et al. |

FOREIGN PATENT DOCUMENTS

| | | |
|---|---|---|
| DE | 4110085 A1 | 1/1992 |
| DE | 10100588 A1 | 7/2002 |
| EP | 0260032 A1 | 3/1988 |
| EP | 0266168 A2 | 5/1988 |
| EP | 0269574 A2 | 6/1988 |
| EP | 0287313 A2 | 10/1988 |
| EP | 0339330 A2 | 11/1989 |
| EP | 339842 A2 | 11/1989 |
| EP | 0417999 A1 | 3/1991 |
| EP | 1389637 A1 | 2/2004 |
| JP | 2-264792 A | 10/1990 |
| WO | WO 86/05518 A1 | 9/1986 |
| WO | WO 89/12060 A1 | 12/1989 |
| WO | WO 90/15814 A1 | 12/1990 |
| WO | WO 91/06556 A1 | 5/1991 |
| WO | WO 91/10671 A1 | 7/1991 |
| WO | WO 91/15499 A1 | 10/1991 |
| WO | WO 92/02258 A1 | 2/1992 |
| WO | 92/03452 A1 | 3/1992 |
| WO | WO 92/03568 A1 | 3/1992 |
| WO | WO 92/07065 A1 | 4/1992 |
| WO | WO 92/20822 A1 | 11/1992 |
| WO | WO 92/20823 A1 | 11/1992 |
| WO | WO 92/22651 A1 | 12/1992 |
| WO | WO 93/07883 A1 | 4/1993 |
| WO | WO 93/24510 A1 | 12/1993 |
| WO | WO 94/01550 A1 | 1/1994 |
| WO | WO 94/02498 A1 | 2/1994 |
| WO | WO 94/02499 A1 | 2/1994 |
| WO | WO 94/02501 A1 | 2/1994 |
| WO | WO 94/17093 A1 | 8/1994 |
| WO | WO 94/23026 A1 | 10/1994 |
| WO | WO 94/26764 A1 | 11/1994 |
| WO | WO 96/07392 A2 | 3/1996 |
| WO | WO 96/11205 A1 | 4/1996 |
| WO | WO 97/26270 A2 | 7/1997 |
| WO | 97/30064 A1 | 8/1997 |
| WO | 97/46570 A1 | 12/1997 |
| WO | 98/16550 A1 | 4/1998 |
| WO | WO 98/39352 A1 | 9/1998 |
| WO | WO 98/52614 A2 | 11/1998 |
| WO | WO 99/14226 A2 | 3/1999 |
| WO | WO 99/32619 A1 | 7/1999 |
| WO | WO 00/08044 A1 | 2/2000 |
| WO | WO 00/44895 A1 | 8/2000 |
| WO | WO 00/44914 A1 | 8/2000 |
| WO | WO 00/49035 A1 | 8/2000 |
| WO | WO 00/63364 A2 | 10/2000 |
| WO | WO 00/76554 A1 | 12/2000 |
| WO | WO 01/29058 A1 | 4/2001 |
| WO | WO 01/36641 A2 | 5/2001 |
| WO | WO 01/36646 A1 | 5/2001 |
| WO | WO 01/48183 A2 | 7/2001 |
| WO | WO 01/049687 A2 | 7/2001 |
| WO | WO 01/75164 A2 | 10/2001 |
| WO | 02/38578 A1 | 5/2002 |
| WO | WO 02/36743 A2 | 5/2002 |
| WO | WO 02/44321 A2 | 6/2002 |
| WO | WO 03/070918 A2 | 8/2003 |
| WO | WO 03/072705 A2 | 9/2003 |
| WO | WO 2004/015107 A2 | 2/2004 |
| WO | 2004/044133 A2 | 5/2004 |
| WO | WO 2004/041889 A2 | 5/2004 |
| WO | WO 2004/043977 A2 | 5/2004 |
| WO | WO 2004/043978 A2 | 5/2004 |
| WO | WO 2004/043979 A2 | 5/2004 |
| WO | WO 2004/044133 A2 | 5/2004 |
| WO | WO 2004/044136 A2 | 5/2004 |
| WO | WO 2004/044138 A2 | 5/2004 |
| WO | WO 2004/044139 A2 | 5/2004 |
| WO | WO 2004/044140 A2 | 5/2004 |
| WO | WO 2004/083430 A2 | 9/2004 |
| WO | WO 2004/097049 A1 | 11/2004 |
| WO | WO 2004/113496 A2 | 12/2004 |
| WO | WO 2005/027962 A2 | 3/2005 |
| WO | 2005/121368 A1 | 12/2005 |
| WO | 2005/121371 A2 | 12/2005 |
| WO | 2005/121372 A2 | 12/2005 |

OTHER PUBLICATIONS

Chun-Nam Lok et al., "Potent gene-specific inhibitory properties of mixed backbone antisense oligonucleotides comprised of 2'-deoxy-2'-fluoro-D-arabinose and 2'-deoxyribose nucleotides," Biochemistry, 2002, 41, 3457-3467.
Min, K.-L. et al., "Oligonucleotides comprised of alternating 2'-deoxy-2'-fluoro-beta-D-arabinonucleosides and D-2'-deoxyribonucleosides (2'F-ANA/DNA 'Altimers') induce efficient RNA cleavage mediated by RNase H," Bioorganic & Medicinal Chemistry Letters, Sep. 2002, 12, 2651-2654.
Wilds, C.J. et al., "Duplex recognition by oligonucleotides containing 2'-deoxy-2'-fluoro-D-arabinose and 2'-deoxy-2'-fluoro-D-ribose. Intermolecular 2'-OH-phosphate contacts versus sugar puckering in the stabilization of triple helical complexes," Bioconjugate Chem., 1999, 10, 299-305.
Schoning, K.-U. et al., "Chemical etiology of nucleic structure: the alpha-Threofuranosyl-(3'→2') oligonucleotide system," Science, Nov. 17, 2000, 290, 1347-1351.
Leydier, C. et al., "4'-Thio-RNA: Synthesis of Mixed Base 4'-Thio-Oligoribonucleotides, Nuclease Resistance, and Base Pairing Properties with Complementary Single and Double Strand," Antisense Research and Development, 1995, 5, 167-174.
Elbashir et al., "RNA Interference is Mediated by 21 and 22 Nucleotide RNAs" Genes and Development, Jan. 2001, 15, 188-200.
Afonina, I. et al., "Sequence-specific arrest of primer extension on single-stranded DNA by an oligonucleotide-minor groove binder conjugate," Proc. Natl. Acad. Sci. USA (1996) 93:3199-3204.
Agrawal, et al., "Oligodeoxynucleoside Phosphoramidates and Phosphorothioates as Inhibitors of Human Immunodeficiency Virus" Proc. Natl. Acad. Sci. USA, 1988, 85, 7079-7083.
Agarwal, et al., "Synthesis and Enzymatic Properties of Deoxyribooligonucleotides Containing Methyl and Phenylphosphonate Linkages", Nucleic Acid Research 1979, 6, 3009-3024.
Agrawal, S. et al., "Synthesis and Anti-HIV Activity of Oligoribonucleotides and Their Phosphorothioate Analogs," Ann. N.Y. Acad. Sci., 1992, 2-10.
Agrawal, S. et al., "Antisense therapeutics: is it as simple as complementary base recognition?," Molecular Med. Today, vol. 6(2), pp. 72-81 (2000).
Agrawal, S., "Antisense Oligonucleotides: Towards Clinical Trials," TIBTECH, 1996, 14, 376-388.
Agris, et al., "Inhibition of Vesicular Stomatitis Virus Protein Synthesis and Infection by Sequence-Specific Oligodeoxyribonucleoside Methylphosphonates", Biochemistry 1986, 25, 6268-6275.
Akashi, et al., "Novel Stationary Phases for Affinity Chromatography. Nucleobase-Selective Recognition of Nucleosides and Nucleotides on Poly(9-vinyladenine)-Supported Silica Gel)", Chem. Letters, 1988, 1093-1096.
Alahari, "Novel chemically modified oligonucleotides provide potent inhibition of P-glycoprotein expression," J. Pharmacology and Experimental Therapeutics, 1998, 286(1), 419-428.
Alberts, et al., "DNA-Cellulose Chromatography", Meth. Enzymol., 1971, 21, 198-217.
Allerson, C.R. et al., Abstract of the 227th ACS National Meeting, Anaheim, CA, Mar. 28-Apr. 1, 2004.
Allerson, C.R. et al., "Fully 2'-Modified Oligonucleotide Duplexes with Improved in Vitro Potency and Stability Compared to Unmodified Small Interfering RNA," J. Med. Chem., 2005, 48, 901-904.
Amarzguioui, M., et al., "Tolerance for mutations and chemical modifications in a siRNA," Nucleic Acids Res., 2003, 31(2), 589-595.
Ambros, V. et al., "A uniform system for MicroRNA annotation," RNA (2003) 9: 277-279.
Ambros, V. et al., "MicroRNAs and Other Tiny Endogenous RNAs in C. elegans, "Curr Biol. (2003) 13: 807-818.
Ambros, V. et al., "MicroRNAs: Tiny Regulators with Great Potential," Cell (2001) 107: 823-826.
Antopolsky, M. et al., "Peptide-Oligonucleotide Phosphorothioate Conjugates with Membrane Translocation and Nuclear Localization Properties," Bioconjugate Chem. (1999) 10(4):598-606.

Arar, K. et al., "Synthesis and Antiviral Activity of Peptide-Oligonucleotide Conjugates Prepared by Using Na-(Bromoaceytl)peptides," Bioconjugate Chem. (1995) 6(5):573-577.
Arndt-Jovin, et al., "Covalent Attachment of DNA to Agarose", Eur. J. Biochem., 1975, 54, 411-418.
Arya, S. K. et al., "Alnhibition of RNA Directed DNA Polymerase of Murine Leukemia Virus by 2'-O-Alkylated Polyadenylic Acids," Biochemical and Biophysical Research Communications, 1974, 59(2), 608-615.
Arya, S. K. et al., "Inhibition of Synthesis of Murine Leukemia Virus in Cultured Cells by Polyribonucleotides and Their 2'-O-Alkyl Derivatives," Molecular Pharmacology, 1976, 12, 234-241.
Asseline, U. et al., "Nucleic acid-binding molecules with high affinity and base sequence specificity: Intercalating agents covalently linked to oligodeoxynucleotides," Proc. Natl. Acad. Sci USA (1984) 81: 3297-3301.
Astriab-Fisher et al., "Conjugates of antisense olgonucleotides with the TAT and antennapedia cell-penetrating peptides: effects on cellular update, binding to target sequences and biologic actions," Pharmaceutical Research (2002) 19(6): 744-754.
Astriab-Fisher, A. et al., "Antisense Inhibition of P-glycoprotein Expression Using Peptide-Oligonucleotide Conjugates," Biochem. Pharmacol. (2000) 60, 83-90.
Baker, B. F. et al., "Oligonucleotide-europium complex conjugate designed to cleave the 5' cap structure of the ICAM-I transcript potentiates antisense activity in cells," Nucleic Acids Res. (1999) 27(6):1547-1551.
Bartel, B. et al., "MicroRNAs: At the Root of Plant Development," Plant Physiol. (2003) 132, 709-717.
Bayer, E. et al., "A New Support for Polypeptide Synthesis in Columns," Tetrahedron Letters, 1970, 51, 4503-4505.
Beaucage S. and Iyer, R., "Advances in the synthesis of oligonucleotides by the phosphoramidite approach", Tetrahedron Letters, 1992, 48, 2223-2311.
Beaucage S. and Iyer, R., "The synthesis of modified oligonucleotides by the phosphoramidite approach and their applications", Tetrahedron, 1993, 49, 6123-6194.
Beigelman, L., et al., "Chemical modification of hammerhead ribozymes," J. of Biological Chem,. 1995, 270(43), 25702-25708.
Bevilacqua et al., "Minor-Groove Recognition of Double-Stranded RNA by the Double-Stranded RNA-Binding Domain from the RNA-Activated Protein Kinase PKR," Biochemistry, 1996, 35, 9983-9994.
Bhat, et al., "A Simple and Convenient Method for the Selective N-Acylations of Cytosine Nucleosides", Nucleosides and Nucleotides, 1989, 8, 179-183.
Biggadike, et al., "Short convergent route to homochiral carbocylic 2'-deoxynucleosides and carbocyclic robonucleosides", J. Chem. Soc. Chem. Commun. 1987, 1083-1084.
Blanks, et al., "An oligodeoxynucleotide affinity column for the isolation of sequence specific DNA binding proteins", Nucleic Acids Res., 1988, 16, 10283-10299.
Blomberg, P., "Control of replication of plasmid R1: the duplex between the antisense RNA, CopA, and its target, CopT, is processed specifically in vivo and in vitro by Rnase III", EMBO J., 1990, 9, 2331-2340.
Bollig, F. et al., "Affinity purification of ARE-binding proteins identifies poly(A)-binding protein 1 as a potential substrate in MK2-induced mRNA stabilization," Biochem. Biophys. Res. Commun. (2003) 301: 665-670.
Bongartz, J.-P. et al., "Improved biological activity of antisense oligonucleotides conjugated to a fusogenic peptide," Nucleic Acids Res. (1994) 22(22):4681-4688.
Bonora, G. M. et al., "Antisense activity of an anti-HIV oligonucleotide conjugated to linear and branched high molecular weight polyethylene glycols," Farmaco (1998) 53:634-637.
Bonora, G. M. et al., "Biological Properties of Antisense Oligonucleotides Conjugated to—Different High-Molecular Mass Poly(Ethylen Glycols)," Nucleosides Nucleotides (1999) 18(6 &7):1723-1725.
Bonora, G.M., et al., "A liquid-phase process suitable for large-scale synthesis of phosphorothioate oligonucleotides," Organic Process Res. & Develop., 2000, 225-231.

Borer, et al., "Stability of ribonucleic acid double-stranded helices," J. Mol. Biol., 1974, 86, 843-853.
Braasch, D.A. et al., "RNA Interference in Mammalian Cells by Chemically-Modified RNA," Biochemistry, 2003, 42, 7967-7975.
Branch, A., "A Good Antisense is Hard to Find," TIBS, 1998, 23, 45-50.
Branda et al., "Amplication of antibody production by phosphorothioate oligodeoxynucleotides," J. Lab. Clin. Med., 1996, 128(3), 329-338.
Branden, L. J. et al., "A peptide nucleic acid-nuclear localization signal fusion that mediates nuclear transport of DNA," Nature Biotech (1999) 17:784-787.
Brantl, S., "Antisense-RNA regulation and RNA interference," Biochimica et Biophysica Acta, 2002, 1575, 15-25.
Brill, et al., "Synthesis of Oligodeoxynucleoside Phosphorodithioates Via Thioamidites", J. Am. Chem. Soc. 1989, 111, 2321-2322.
Brown-Driver et al., "Inhibition of Translation of Hepatitis C Virus RNA by 2'-Modified Antisense Oligonucleotides," Antisense Nucleic Acid Drug Dev. (1999) 9(2): 145-154.
Buhr, C.A. et al., "Oligodeoxynucleotides containing C-7 propyne analogs of 7-deaza-2'-deoxyguanosine and 7-deaza-2'-deoxyadenosine," Nucleic Acids Research, 1996, 24(15), 2974-2980.
Bunemann, et al., Immobilization of denatured DNA to macroporous supports: I. Efficiency of different coupling procedures, Nucleic Acids Res., 1982, 10, 7163-7180.
Bunemann, H., "Immobilization of denatured DNA to macroporous supports: II. Steric and kinetic parameters of heterogeneous hybridization reactions", Nucleic Acids Res., 1982, 10, 7181-7196.
Butke, et al., "Facile synthesis of 2'amino-2deoxynucleoside from the corresponding arabino derivative," Nucleic Acid Chemistry, 1986, Part Three, 149-152.
Butler, M. et al., "Specific Inhibition of PTEN Expression Reverses Hyperglycemia in Diabetic Mice," Diabetes, 2002, 51, 1028-1034.
Caplen et al., "dsRNA-mediated gene silencing in cultured Drosophila cells: a tissue culture model for the analysis of RNA interference," GENE (2000) 252: 95-105.
Caplen, N.J., et al., "Specific inhibition of gene expression by small double-stranded RNAs in invertebrate and vertebrate systems," PNAS, 2001, 98(17), 9742-9747.
Carmell, M.A. et al., "the argonaute family: tentacles that reach into RNAi, developmental control, stem cell maintenance, and tumorigenesis," Genes and Development, 2002, 16, 2733-2742.
Caruthers, M., "Synthesis of Oligonucleotides and Oligonucleotide Analogues", in "Oligonucleotides. Antisense Inhibitors of Gene Expression.", J.S. Cohen, Ed., CRC Press, Inc., 7-24, (1989).
Castle, et al., "Imidazo[4, 5-D]pyridazines. I. Synthesis of 4,7-disubstituted derivatives", Journal of Organic Chemistry, 1958, 23, 1534-1538.
Cazalla, D. et al., "Nuclear Export and Retention Signals in the RS Domain of SR Proteins," Mol. Cell. Biol. (2002) 22(19):6871-6882.
Cazenave, C. et al., "Enzymatic amplification of translation inhibition of rabbit β-globin mRNA mediated by anti-messenger oligodeoxynucleotides covalently linked to intercalating agents", Nucl. Acids Res., 1987, 15, 4717-4736.
Cerutti, H., "RNA interference: traveling in the cell and gaining functions?" Trends in Genetics (2003) 19(1): 39-46.
Chaloin, L. et al., "Design of Carrier Peptide-Oligonucleotide Conjugates with Rapid Membrane Translocation and Nuclear Localization Properties," Biochem. Biophys. Res. Commun. (1998) 243:601-608.
Chen and Wu, "Studies on Fluoroalkylation and Fluroalkoxylation. Part 33. Direct Trifluoromethylation of Aryl Halides with Fluorosulphonyldifluoromethyl Iodide in the Presence of Copper: an Electron Transfer Induced Process," J. Chem. Soc., Perkin Transactions, 1989, 1, 2385-2387.
Chiang et al., "Antisense Oligonucleotides Inhibit Intercellular Adhesion Molecule 1 Expression by Two Distinct Mechanisms," J. Biol. Chem., 1991, 266, 18162-18171.
Chirila, T.V. et al., "The use of synthetic polymers for delivery of therapeutic antisense oligodeoxynucleotides," Biomaterials, vol. 23(2), pp. 321-342 (2002).

Chiu, Y.-L. et al., "RNAi in human cells: basic structural and functional features of small interfering RNA," Molecular Cell, Sep. 2002, 10, 549-561.
Chladek, et al., "Facile Synthesis of 2'Amino-2'Deoxyadenosine," J. Carbohydtrates, Necleosides & Nucleotides, 1980, 7, 63-75.
Chodosh, et al., "A Single Polypeptide Possesses the Binding and Transcription Activities of the Adenovirus Major Late Transcription Factor", Mol. Cell. Biol., 1986, 6, 4723-4733.
Choung, S. et al., "Chemical modification of siRNAs to improve serum stability without loss of efficacy," Biochemical and Biophysical Research Communications, 2006, 342, 919-927.
Christofferson et al., "Ribozymes as human therapeutic agents", J. Med. Chem., 1995, 38(12), 2023-2037.
Cogoni, C. et al., "Post-transcriptional gene silencing across kingdoms," Curr. Opin. Genet Dev., 2000, 10(6), 638-643.
Cohen, G. L. et al., "Sequence Dependent Binding of cis-Dichlorodiamrnineplatinum(II) to DNA," J. Am. Chem. Soc. (1980) 102(7), 2487-2488.
Concise Encyclopedia of Polymer Science and Engineering, pp. 858-859, Kroschwitz, J.I., Ed., John Wiley & Sons, 1990.
Constant et al., "Heterodimeric Molecules Including Nucleic Acid Bases and 9-Aminoacridine Spectroscopic Studies, Conformations, and Interactions with DNA", Biochemistry, 1988, 27, 3997-4003.
Cook, "Medicinal chemistry of antisense oligonucleotides—future opportunities," Anti-Cancer Drug Design, 1991, 6, 585-607.
PCT International Search Report dated Jan. 24, 2005 (PCTUS03/35087).
The PCT International Search Report dated Aug. 13, 2004 (PCT/US03/35072).
The PCT International Search Report dated Aug. 2, 2004 (PCT/US03/35068).
The PCT International Search Report dated Aug. 23, 2004 (PCT/US03/35063).
The PCT International Search Report dated Dec. 1, 2003 (PCT/US03/19043).
Corey, D. R. et al., "Generation of a Hybrid Sequence-Specific Single-Stranded Deoxyribonuclease," Science (1987) 238:1401-1403.
Corey, D. R. et al., "Sequence-Selective Hydrolysis of Duplex DNA by an Oligonucleotide-Directed Nuclease," J. Am. Chem. Soc. (1989) 111(22):8523-8525.
Corey, D. R., "48000-fold Acceleration of Hybridization by Chemically Modified Oligonucleotides," J. Am. Chem. Soc. (1995) 117(36):9373-9374.
Cossum, P.A. et al., "Disposition of the 14C-Labeled Phosphorothioate Oligonucleotide ISIS 2105 after Intravenous Administration to Rats," J. Pharmacol. Exp. Ther., 1993, 267(3), 1181-1190.
Couzin, J., "Small TNAs Make Big Splash," Science (2002) 298: 2296-2297.
Crawford, J.M., "Role of Vesicle-Mediated Transport Pathways in Hepatocellular Bile Secretion," Semin. Liver Dis., 1996, 16(2), 169-189.
Crooke, et al., "Kinetic characteristics of *Escherichia coli* Rnase H1: cleavage of various antisense oligonucleotide-RNA duplexes", Biochem. J., 1995, 312, 599-608.
Crooke, S.T. and Bennett, C.F., "Progress in Antisense Oligonucleotide Therapeutics", Annu. Rev. Pharmacol. Toxicol., 1996, 36, 107-129.
Crooke, S.T., Antisense Research & Application, Chapter 1, pp. 1-50, Publ. Springer-Verlag, Ed. S.T. Crooke (1998).
Cummins, L.L. et al., "Characterization of fully 2'modified oligoribonucleotide hetero- and homoduplex hybridization and nuclease sensitivity," Nucleic Acids Research, 1995, 23(11), 2019-2024.
Czauderna, F., et al., "Structural variations and stabilizing modifications of synthetic siRNAs in mammalian cells," Nucleic Acids Res., 2003, 31(11), 2705-2716.
Dagle, et al., "Pathways of Degradation and Mechanism of Action of Antisense Oligonucleotides in *Xenopus laevis* Embryos", Antisense Res. And Dev., 1991, 1, 11-20.
Dagle, et al., "Physical properties of oligonucleotides containing phosphoramidate-modified internucleoside linkages", Nucleic Acids Research, 1991, 19, 1805-1810.

Dagle, et al., "Targeted degradation of mRNA in *Xenopus oocytes* and embryos directed by modified oligonucleotides: studies of An2 and cyclin in embryogenesis", Nucleic Acids Research, 1990, 18, 4751-4757.

Dake, et al., "Purification and Properties of the Major Nuclease from Mitochondria of *Saccharomyces cerevisiae*", J. Biol. Chem., 1988, 263, 7691-7702.

Damha, et al., "Solution and solid phase chemical synthesis of arabinonucleotides", Can J. Chem., 1989, 831-839.

Dande, P. et al., Abstract from the 227th ACS National Meeting, Anaheim, CA, Mar. 28-Apr. 1, 2004.

Day, et al., "Immobilization of polynucleotides on magnetic particles", Biochem. J., 1991, 278, 735-740.

De las Heras, et al., "3'-C-Cyano-3'-Deoxythymidine," Tetrahedron Letters, 1988, 29, 941-944.

De Mesmeker, et al., "Antisense Oligonucleotides", Acc. Chem. Res., 1995, 28, 366-374.

DeClercq, E. et al., "Influence of various 2- and 2'-substituted polyadenyl acids on murine leukemia virus reverse transcriptase," Cancer Letters, 1979, 7, 27-37.

Denny, W.A., "DNA-intercalating ligands as anti-cancer drugs: prospects for future design," Anti-Cancer Drug Design, 1989, 4, 241-263.

Dignam, et al., "Accurate transcription initiation by RNA polymerase II in a soluble extract from isolated mammalian nuclei," Nucleic Acids Res., 1983, 11, 1475-1489.

Divakar, et al., "Approaches to the Synthesis of 2'-Thio Analogues of Pyrimidine Ribosides", J. Chem. Soc., Perkins Trans., I, 1990, 969-974.

Divakar, et al., "Reaction Between 2,2'-Anhydro-1-β-D-arabinofuranosyluracil and Thiolate Ions", J. Chem. Soc., Perkins Trans. I, 1982, 1625-1628.

Dreyer, et al., "Sequence-specific cleavage of single-stranded DNA: Oligodeoxynucleotide-EDTA-Fe(II)", Proc. Natl. Acad. Sci. USA, 1985, 82, 968-972.

Drmanac, et al., "DNA Sequence Determination by Hybridization: A Strategy for Efficient Large-Scale Sequencing", Science, 1993, 260, 1649-1652.

Duff, R. J. et al., "[17] intrabody Tissue-Specific Delivery of Antisense Conjugates in Animals: Ligand-Linker-Antisense Oligomer Conjugates," Methods Enzymol. (2000) 313:297-321.

Duncan, et al., "Affinity Chromatography of a Sequence-Specific DNA Binding Protein Using Teflon-Linked Oligonucleotides", Anal. Biochem., 1988, 169, 104-108.

Dunn, J.J. and Studier, F.W., "Effect of RNAase III Cleavage on Translation of Bacteriophage T7 Messenger RNAs", J. Mol. Biol., 1975, 99, 487-499.

Eckstein, et al., "Polynucleotides Containing 2'Chloro-2'Deoxyribose", Biochemistry, 1972, 11, 4336-4344.

Eddy, S.R., "Non-Coding RNA Genes and the Modern RNA World," Nature Rev. Genetics (2001) 2: 919-929.

Eder, P.S. and Walder, J.A., "Ribonuclease H from K562 Human Erythroleukemia Cells", J. Biol. Chem., 1991, 266, 6472-6479.

Efimov, V. A. et al., "Synthesis of Polyethylene Glycol—Oligonucleotide Conjugates," Bioorg. Khim. (1993) 19(8):800-804.

Elela, et al., "RNase III Cleaves Eukaryotic Preribosomal RNA at a U3 snoRNP-Dependent Site", Cell, 1996, 85, 115-124.

Elmén, J. et al., "Locked nucleic acid (LNA) mediated improvements in siRNA stability and functionality," Nucleic Acids Res. 2005, 33(1), 439-447.

EP Supplementary Search Report for EP 03716922 dated May 12, 2006.

Fahy, et al., "Design and synthesis of polyacrylamide-based oligonucleotide supports for use in nucleic acid diagnostics", Nucl. Acids Res., 1993, 21, 1819-1826.

Fazakerley, G.V., et al., "A→Z transition in the synthetic hexanucleotide (dCdGfl)3," FEBS, 1985, 182(2), 365-369.

Fire et al., "RNA-triggered gene silencing," TIG (1999) 15(9): 358-363.

Firestone, R. A., "Low-Density Lipoprotein as a Vehicle for Targeting Antitumor Compounds to Cancer Cells," Bioconjugate Chem. (1994) 105-113.

Fishel, et al., "Z-DNA Affinity Chromatography", Methods Enzymol., 1990, 184, 328-342.

Flanagan, W.M. et al., "Cellular penetration and antisense activity by a phenoxazine-substituted heptanucleotide," Nature Biotechnol. (1999) 17(1): 48-52.

Fodor, et al., "Light-Directed, Spatially Addressable Parallel Chemical Synthesis", Science, 1991, 251, 767-773.

Fox, et al., "Nucleosides. XVIII. Synthesis of 2'-Fluorothymidine, 2'-Flurodeoxyuridine, and Other 2'-Halogeno-2'-Deoxy Nucleosides 12", J Org. Chem., 1964, 29, 558-564.

Francis, A.W. et al., "Probing the Requirements for Recognition and Catalysis in Fpg and MutY with Nonpolar Adenine Isosteres," J. Am. Chem. Soc. (2003) 125(52): 16235-16242.

Fraser, A., et al., "Synthesis and conformational properties of 2'-deoxy-2'-methylthiopyrimidine and -purine nucleosides:potential antisense applications," J. Heterocycl. Chem., 1993, 30, 1277-1287.

Fraser, A.G. et al., "Functional genomic analysis of *C. elegans* chromosome 1 by systemic RNA interference," Nature, 2000, 408, 325-330.

Freskos, "Synthesis of 2'Deoxypyrimidine Nucleosides Via Copper (I) Iodine Catalysis," Nucleosides & Nucleotides, 1989, 8, 1075, 1076.

Fusi, et al., "Ribonucleases from the extreme thermophilic archaebacterium S. Solfataricus", Eur. J. Biochem., 1993, 16, 305-310.

Gabrielsen, et al., AMagnetic DNA affinity purification of yeast transcription factor $_T$-a new purification principle for the ultrarapid isolation of near homogeneous factor, Nucleic Acids Research, 1989, 17, 6253-6267.

Gaffney, et al., "A New Strategy for the Protection of eoxyguanosine During Oligonucleotide Synthesis," Tetrahedron Letters, 1982, 23, 2257-2260.

Gao, J. et al., "Expanded-Size Bases in Naturally Sized DNA: Evaluation of Steric Effects in Watson-Crick Pairing," J. Am. Chem. Soc. (2004) 126(38): 11826-11831.

Gbenle, "Simultaneous Isolation of Cytoplasmic Endoribonuclease and Exoribonucease of Trypanosoma Brucei", Mol. Biochem. Parasitol., 1985, 15, 37-47.

Gbenle, "Trypanosoma brucei: Calcium-Dependent Endoribonuclease is Associated with Inhibitor Protein," Exp. Parasitol., 1990, 71, 432-438.

Geary, R.S. et al., "Pharmacokinetic Properties of 2'-O-(2-Methoxyethyl)-Modified Oligonucleotide Analogs in Rats," J. Pharmacol. Exp. Therap., 1998, 296(3), 890-897.

Gerdes, K., et al., "Mechanism of Killer Gene Activation. Antisense RNA-dependent Rnase III Cleavage Ensures Rapid Turn-over of the Stable-Hok, SrnB and PndA Effector Messenger RNAs", J. Mol. Biol., 1992, 226, 637-649.

Gingeras, et al., "Hybridization properties of immobilized nucleic acids", Nucl. Acids Res., 1987, 15, 5373-5391.

Goldkorn, T. and Prockop, D.J., "A simple and efficient enzymatic method for covalent attachment of DNA to cellulose. Application for hybridization-restriction analysis and for in vitro synthesis of DNA probes", Nucleic Acids Res., 1986, 14, 9171-9191.

Goodchild, et al., "Conjugates of Oligonucleotides and Modified Oligonucleotides: A Review of their Synthesis and Properties", Bioconjugate Chem., 1990, 1(3), 165-187.

Gorlach, M. et al., "The mRNA Poly(A)-Binding Protein: Localization, Abundance, and RNABinding Specificity," Exp. Cells Res. (1994) 211:400-407.

Goss, T.A. and Bard, M., "High-performance affinity chromatography of DNA", J. Chromatogr., 1990, 508, 279-287.

Graham, et al., "Tritium Labeling of Antisense Oligonucleotides by Exchange with Tritiated Water," Nucleic Acids. Res., 1993, 16, 3737-3743.

Graham, M.J. et al., "In Vivo Distribution and Metabolism of a Phosphorothioate Oligonucleotide within Rat Liver after Intravenous Administration," J. Pharmacol. Exp. Therap., 1998, 286(1), 447-458.

Gravert, D.J., et al., "Organic synthesis on soluble polymer supports," Chem. Rev., 1997, 97, 489-509.

Griffey, R.H. et al., "2'-O-Aminopropyl Ribonucleotides: A Zwitterionic Modification that Enhances the Exonuclease Resistance and Biological Activity of Antisense Oligonucleotides," J. Med. Chem., 1996, 39(26), 5100-5109.

Grishok, A. et al., "Genetic Requirements for Inheritance of RNAi in *C. elegans*," Science, 2000, 287, 2494-2497.

Grünweller, A. et al., "Comparison of different antisense strategies in mammalian cells using locked nucleic acids, 2'-O-methyl RNA, phosphorothioates and small interfering RNA," Nucleic Acids Research, 2003, 31(12), 3185-3193.

Guckian, K.M. et al., "Structure and Base Pairing Properties of a Replicable Nonpolar Isostere for Deoxyadenosine," J Org Chem (1998) 63(26);9652-9656.

Guo, et al., "Direct fluorescence analysis of genetic polymorphisms by hybridization with oligonucleotide arrays on glass supports", Nucl. Acids Res., 1994, 22, 5456-5465.

Guo, S. et al., "par-1, a Gene Required for Establishing Polarity in *C. elegans* Embryos, Encodes a Putative Ser/Thr Kinase That is Asymmetrically Distributed," Cell, 1995, 81(4), 611-620.

Gura, T., "A silence that speaks volumes," Nature, 2000, 404, 804-808.

Guschlbauer, et al., "Nucleoside conformation is Determined by the Electronegativity of the Sugar Substituent," Nucleic Acids Res., 1980, 8, 1421-1433.

Guschlbauer, W. et al., "Poly-2'-deoxy-2'-fluoro-cytidylic acid: enzymatic synthesis, spectroscopic characterization and interaction with poly-inosinic acid," Nucleic Acid Research, 1977, 4(6),1933-1943.

Guschlbauer, W., et al., "Use of 2'-deoxy-2'-fluoro-necleosides in the study of polynucleotide conformation: a progress report," Nucleic Acid Research Symposium Series, 1982, 11,113-116.

Gutierrez, A.J. et al., "Antisense Gene Inhibition by C-5 Substituted Deoxyuridine-Containing Oligodeoxynucleotides," Biochemistry, 1997, 36(4), 743-748.

Guzaev, A. et al., "Conjugation of Oligonucleotides Via an Electrophilic Tether: N-Chloroacetarnidohexyl Phosphoramidite Reagent," Bioorg. Med. Chem. lett . (1998) 8:3671-3676.

Haeuptle and Dobberstein, "Translation arrest by oligonucleotides complementary to mRNA coding sequences yields polypeptides of predetermined length", Nucleic Acids Res., 1986, 14, 1427-1448.

Hall, J. et al., "Efficient sequence-specific cleavage of RNA using novel europium complexes conjugated to oligonucleotides," Chem. Biol. (1994) 1(3):185-190.

Hamada et al., "Effects on RNA Interference in Gene Expression (RNAi) in Cultured Mammalian Cells of Mismatches and the Introduction of Chemical Modifications at the 3'Ends of siRNAs," Antisense and Nucleic Acid Drug Development (2002) 12:301-309.

Hamilton et al., "A species of small antisense RNA in post-transcriptional gene silencing in plants," Science (1999) 286 (5441): 950-952.

Hammond et al., "Post-Transcriptional Gene Silencing byDouble-Stranded RNA," Nature, 2001, 2, 110-119.

Hansske, et al., "2'and 3'-ketonucleosides and their arabino and XYLO reduction products," Tetrahedron, 1984, 40, 125-135.

Hariton-Gazal, E. et al., "Targeting of Nonkaryophilic Cell-Permeable Peptides into the Nuclei of Intact Cells by Covalently Attached Nuclear Localization Signals," Biochemistry (2002) 41(29):9208-9214.

Henderson, B. R. et al., "A Comparison of the Activity, Sequence Specificity, and CRM1-Dependence of Different Nuclear Export Signals," Exp. Cell Res. (2000) 256:213-224.

Hertel, et al., "Synthesis of 2-deoxy-2,2-difluoro-D-ribose and 2-deoxy-2,2-difluoro-D-ribofuranosyl nucleosides," J. Org. Chem., 1988, 53, 2406-2409.

Hill, F. et al., "Polymerase recognition of synthetic oligodeoxyribonucleotides incorporating degenerate pyrimidine and purine bases," Proc. Natl. Acad. Sci. USA, 1998, 95, 4258-4263.

Hobbs, J. et al., Poly 2'-Deoxy-2'-Aminouridylic Acid, 1972, Biochem. Biophys. Res. Commun., 46(4), 1509-1515.

Hobbs, J. et al., "Polynucleotides Containing 2'-Amino 2'-deoxyribose and 2'-Azido-2'-deoxyribose," Biochem., 1973, 12, 5138-5145.

Hobbs, J. et al., "Polynucleotides Containing 2'-Chloro-2'-deoxyribose," Biochem., Eckstein et al., Ed., 1972, 11, 4336-4344.

Hoffman, K., "Imidazole and its Derivatives" in The Chemistry of Heterocyclic Compounds, Weissberger, A., Ed.,lnterscience Publishers, Inc., NewYork, 1953, 447.

Holen, T., et al., "Similar behaviour of single-strand and double-strand siRNAs suggests they act through a common RNAi pathway," Nucleic Acids Res., 2003, 31(9), 2401-2407.

Hornbeck, P. et al., Enzyme-Linked Immunosorbet Assays (ELIASE), Curr. Protocols Mol. Biol., 1991, John Wiley & Sons, pp. 11.2.1-11.2.22.

Hornung, V. et al., "Sequence-specific potent induction of IFN-a by short ineterfering RNA in plasmacytoid dendritic cells through TLR7," Nature Med., 2005, 11(3), 263-270.

Huang, L. et al., "Oligonucleotide conjugates of Eu(III) tetraazamacrocycles with pendent alcohol and amide groups promote sequence-specific RNA cleavage," J Biol Inorg. Chem (2000) 5:85-92.

Huh, N. et al., "Design, Synthesis, and Evaluation of Mitomycin-Tethered Phosphorothioate Oligodeoxynucleotides," Bioconjugate Chem. (1996) 7:659-669.

Hunter, "Genetics: a touch of elegance with RNAi," Current Biology, Current Science (1999) 9(12): R440-R442.

Hunziker, J. et al., "Nucleic acid analogues: synthesis and properties," Modern Synthetic Methods, 1995, 331, 334-417.

Hyrup, B. and Nielsen, P., "Peptide Nucleic Acids (PNA): Synthesis, Properties and Potential Applications", Bioorganic & Med. Chem., 1996, 4, 5-23.

Ikehara, et al, "Studies of Nucleosides and Nucleotides-LXV' Purine Cyclonucleosides-26 A Versatile Method for the Synthesis of Purine O-Cyclo-Bucleosides. The First Synthesis of 8,2'Anhydro-8-Oxy 9-B-D-Arabinofuranosylguanine," Tetrahedron, 1975, 31, 1369-1372.

Ikehara, et al, "Studies of Nucleosides and Nucleotides-LXXXVII. 1, Purine Cyclonucleosides. XLII. Synthesis of 2'deoxy-2'fluorofunaosine," Chem. and Pharm. Bull., 1981, 29, 1034-1038.

Ikehara, et al. "Purine cyclonucleosides. (43). Synthesis and properties of 2'halogen-2'deoxyguanosines 1," Chem and Pharm Bull., 1981, 29, 3281-3285.

Ikehara, et al., "A Linear Relationship Between Electronegativity of 2'-Substituents and Conformation of Adenine Nucleosides," Tetrahedron Letters, 1979, 42, 4073-4076.

Ikehara, et al., "Improved Synthesis of 2'-fluoro-2'deoxyadenosine and Synthesis and Carbon-13 NMR Spectrum of its 3',5'-cyclic Phosphate Derivative," Nucleosides & Nucleotides, 1983, 2, 373-385.

Ikehara, et al., "Polynucleotides. L. synthesis and properties of poly (2'chloro-2'-deoxyadenylic acid) and poly (2'-bromo-2'-deoxyadenylic acid)", Nucleic Acids Res., 1978, 4, 4249-4260.

Ikehara, et al., "Polynucleotides. LII. Synthesis and properties of poly (2'-deox-2'-fluoroadenylic acid)," Nucleic Acids Research, 1978, 5, 1877-1887.

Ikehara, et al., "Polynucleotides. LVI. Synthesis and Properties of Poly(2'-deoxy-2'-fluoroinosinic Acid)", Nucleic Acids Res., 1978, 5, 3315-3324.

Ikehara, et al., "Purine 8-Cyclonucleosides," Accts. Chem Res., 1969, 2, 47-53.

Ikehara, et al., "Studies of Nucleosides and Nucleotides-LXXIV1 Purine Cyclonucleosides—34 A New Method for the Synthesis of 2'-substituted 2'-deoxyadenosines," Tetrahedron, 1978, 34, 1133-1138.

Ikehara, et al., "Studies of Nucleosides and Nucleotides-LXXXII. 1 Cyclonucleosides. (39). 2 Synthesis and properties of 2'halogen-2'-deoxyadenosines," Chem. Pharm. Bull., 1978, 26, 2449-2453.

Ikehara, M., "2'-substituted 2'-deoxypurineucleotides their conformation and properties," Heterocycles, 1984, 21(1), 75-90.

Imazawa, et al., "Nucleosides and nucleotides. XII.1) Synthesis and properties of 2'-deoxy-2'-mercaptouridine and its derivates", Chem. Pharm. Bull., 1975, 23, 604-610.

Inoue et al., "Sequence dependent hydrolysis of RNA using modified oligonucleotide splints and Rnase H", FEBS Lett., 1987, 215(2), 327-330.

Inoue, et al., "Synthesis and hybridization studies on two complementary nona(2'-O-methyl) ribonucleotides", Nucleic Acid Res., 1987, 15, 6131-6148.

International Search Report Dated Aug. 23, 2004 for International Application No. PCT/US03/09808.

International Search Report dated Mar. 24, 2005 for International Application No. PCT/US03/35088.

International Search Report dated Nov. 18, 2004 for International Application No. PCT/US03/29294.

Jäger, A. et al., "Oligonucleotide N-alkylphosphoramidates: Synthesis and binding to polynucleotides", Biochemistry 1988, 27, 7237-7246.

Janik, B., et al., "Synthesis and Properties of Poly 2'-Fluoro-2'-Deoxyuridylic Acid," Biochem. Biophys. Res. Comm., 1972, 46(3), 1153-1160.

Jarvi, et al., "Synthesis and biological evaluation of dideoxunucleosides containing a difluoromethylene unit", Nucleosides & Nucleotides, 1989, 8, 1111-1114.

Jaschke, A. et al., "Synthesis and properties of oligodeoxyribonucleotide-polyethyleneg lycol conjugates," Nucleic Acids Res. (1994) 22(22):4810-4817.

Jayaraman, et al., "Selective Inhibition of Escherichia coli Protein Synthesis and Growth by Nonionic Oligonucleotides Complementary to the 3' end of 16S rRNA", Proc. Natl. Acad. Sci. USA 1981, 78(3), 1537-1541.

Jen et al., "Suppression of Gene Expression by Targeted Disruption of Messenger RNA: Available Options and Current Strategies," Stem Cells, 2000, 18, 307-319.

Jones, et al., "4'-substituted nucleosides. 5. hydroxymethylation of nucleoside 5'-aldehydes", J. Org. Chem., 1979, 44, 1309-1317.

Jones, et al., "Transient protection: Efficient one-flask synthesis of protected deoxynucleosides", J. Am. Chem. Soc., 1982, 104, 1316-1319.

Jones, L.J. et al., "RNA Quantitation by Fluorescence-Based Solution Assay: RiboGreen Reagent Characterization," Anal. Biochem., 1998, 265, 368-374.

Jorgensen. R. A. et al., "Chalcone synthase cosuppression phenotypes in petunia flowers: comparison of sense vs. antisense constructs and single-copy vs. complex T-DNA sequences," Plant Mol. Biol., 1996, 31(5), 957-973.

Juby, C. D. et al., "Facile Preparation of 3'0ligonucleotide-Peptide Conjugates," Tetrahedron Letters (1991) 32(7):879-882.

Kadonaga, J.T. And Tjian, R.,"Affinity purification of sequence-specific DNA binding proteins", Proc. Natl. Acad. Sci. USA, 1986, 83, 5889-5893.

Kadonaga, J.T., "Purification of Sequence-Specific Binding Proteins b DNA Affinity Chromatography", Methods in Enzymology, 1991, 208, 10-23.

Kasher, et al., "Rapid Enrichment of HeLa Trancription Factors IIIB and IIIC by Using Affinity Chromatography Based on Avidin-Biotin Interactions", Mol. and Cell. Biol., 1986, 6, 3117-3127.

Kawaguchi, et al., "Purification of DNA-binding transcription factors by their selective adsorption of the affinity atex particles", Nucleic Acids Research, 1989, 17, 6229-6240.

Kawasaki, et al., "Synthesis and Biophysical Studies of 2'-dRIBO-2'-F Modified Oligonucleotides", Conf. on Nucleic Acid Therapeutics, Clearwater, FL, Jan. 13-16, 1991, 10 pages.

Kawasaki, H/ et al., "Hesl is a target of MicroRNA-23 during retinoic-acid-induced neuronal differentiation of NT2 cells," Nature (2003) 423: 838-842.

Kennedy, "Hydrophobic Chromatography", Methods in Enzymology, 1990, 182, 339-343.

Khurshid et al., "The unique conformational stability of poly 2'-O-Ethyladenylic Acid," FEBS Letters, 1972, 28(1), 25.

Khvorova, A. et al., "Functional siRNAs Exhibit Strand Bias," Cell, 2003, 115(2), 209-216.

Kiaris, H. et al., "Antagonists of Growth Hormone-Releasing Hormone Inhibit the Growth of U-87MG Human Gliobastoma in Nude mice," Neoplasia, 2000, 2(3), 242-250.

Kielanowska et al., "Preparation and properties of poly 2'-O-ethylcytidylic acid," Nucl. Acids Res., 1976, 3(3), 817-824.

Kimura-Harada, "5-methyl-2-thiouridine: A new sulfur-containing minor constituent from rat liver glutamic acid and lysine tRNAs," FEBS Lett., 1971, 13, 335-338.

Kingston, R.E. et al., "Calcium Phosphate Transfection", Current Protocols in Neuroscience, 1997, Supplement 1, A.1C.1-A.1C.8.

Klopffer, A.E. et al., "Synthesis of 2'-Aminoalkyl-Substituted Fluorinated Nucleobases and Their Influence on the Kinetic Properties of Hammerhead Ribozymes," ChemBioChem (2004) 5: 707-716.

Klopffer, A.E. et al., "The effect of universal fluorinated nucleobases on the catalytic activity of ribozymes ," Nucleosides Nucleotides Nucleic Acids (2003) 22(5-8): 1347-1350.

Knecht, D., "Application of Antisense RNA to the Study of the Cytoskeleton: Background, Principles, and a Summary of Results Obtained with Myosin Heavy Chain", Cell Motil. Cytoskel., 1989, 14, 92-102.

Knochbin et al., "An antisense RNA involved in p53 mRNA maturation in murine erythroleukemia cells induced to differentiate", EMBO J., 1989, 8, 4107-4114.

Knorre, et al., "Complementary-Addressed Sequence-Specific Modification of Nucleic Acids", Progress in Nucleic Acid Research and Molecular Biology 1985, 32, 291-321.

Koizumi, M. et al., "Design of RNA enzymes distinguishing a single base mutation in RNA," Nucleic Acids Research, 1989, 17, 7059-7071.

Koole, et al., "Synthesis of phosphate-methylated DNA fragments using 9- fluorenylmethoxycarbonyl as transient base protecting group", J. Org. Chem., 1989, 54, 1657-1664.

Kraynack, B.A. et al., "Small interfering RNAs containing full 2'-O-methylribonucleotide-modified sense strands display Argonaute2/eIF2C2-dependent activity," RNA, 2006, 12, 163-176.

Krieg, A. M. et al., "Uptake of Oligodeoxyribonucleotides by Lymphoid Cells Is Heterogeneous and Inducible," Antisense Research and Development (1991) 1:161-171.

Krinke, L. et al., "RNase III-dependent hybrolysis of ÿcll-O gene mRNA mediated by ÿ OOP antisense RNA", Genes & Devel., 1990, 4, 2223-2233.

Krug, A., et al., "Synthesis of oligonucleotide probes containing 2'-deoxy-2'-fluoronucleosides for cleavage of RNA by RNase H," Biomed. Biochem. Acta, 1990, 49, 161-166.

Krug, A., et al., "The behaviour of 2'-deoxy-2'-fluorouridine incorporated into oligonucleotides by the phosphoramidite approach," Nucleosides & Nucleotides, 1989, 8(8), 1473-1483.

Krystal et al., "N-myc mRNA Forms an RNA-RNA Duplex with Endogenous Antisense Transcripts", Mol. and Cell. Biol., 1990, 10, 4180-4191.

Kuijpers, W. H. A. et al., "Specific Recognition of Antibody-Oligonucleotide Conjugates by Radiolabeled Antisense Nucleotides: A Novel Approach for Two-Step Radioimmunotherapy of Cancer," Bioconjugate Chem. (1993) 4(1):94-102.

Kuimelis, "Synthesis of oligodeoxynucleotides containing 2-thiopyrimidine residues—a new protection scheme," Nucleic Acids Res. 1994, 22(8), 1429-1436.

Kumar et al., "Antisense RNA: function and fate of duplex RNA in cells of higher eukaryotes," Microbiology and Molecular Biology Reviews (1998) 62(4): 1415-1434.

Kurchavov, N.A., et al., "A new phosphoramidite reagent for the incorporation of diazaphenoxazinone nucleoside with enhanced base-pairing properties into oligodeoxynucleotides," Nucleosides and Nucleotides, 1997, 16, 1837-1846.

Kurreck, J., "Antisense technologies, Improvement through novel chemical modifications," Eur. J. Biochem., 2003, 270(8), 1628-1644.

Kusmierek et al., "Alkyation of cytidine-5'-phosphate: Mechanisms of alkylation, influence of O'-alkylation on susceptibility of pyrimidine nucleotides to some nucleolytic enzymes, and synthesis of 2'-O-alkyl polynucleotides," ACTA Biochim. Polonica, 1973, 20(4), 365-381.

Lai J. S. et al., "Fluorinated DNA Bases as Probes of Electrostatic Effects in DNA Base Stacking," Angew. Chem. Int. Ed. (2003) 42: 5973-5977.

Lai, J. S. et al., "Selective Pairing of Polyfluorinated DNA Bases," J. Am. Chem. Soc. (2004) 126(10): 3040-3041.

Le Doan et al., "Sequence-Targeted Chemical Modifications of Nucleic Acids by Complementary Oligonucleotides Covalently Linked to Porphyrins", Nucleic Acid Research, 1987, 15, 8643-8659.

Lee, R.C. et al., "The C. elegans heterochronic gene lin-4 encodes small RNAs with antisense complementarity to lin-14," Cell, 1993, 75(5), 843-854.

Lee, Y. et al., "MicroRNA maturation: stepwise processing and subcellular localization," EMBO J. (2002) 21(17): 4663-4670.

Lee, Y. et al., "The nuclearRNase III Drosha initiates microRNA processing," Nature (2003) 425: 415-419.

Leeds, J.M. et al., "Pharmacokinetic Properties of Phosphorothioate Oligonucleotides," Nucleosides Nucleotides, 1997, 16(7-9), 1689-1693.

Lengyel, P., "Double-stranded RNA and interferon action," J. Interferon Res., 1987, 7, 511-519.

Letsinger et al., "Effects of Pendant Groups at Phosphorus on Binding Properties of D-ApA Analogues", Nucleic Acids Research, 1986, 14, 3487-3499.

Lewis, D.L. et al., "Efficient delivery of siRNA for inhibition of gene expression in postnatal mice," Nature Genetics, 2002, 32, 107-108.

Li, S. et al., "Folate-Mediated Targeting of Antisense Oligodeoxynucleotides to Ovarian Cancer Cells," Pharm. Res. (1998) 15(10):1540-1545.

Liao, "A pyrimidine-guanine sequence-specific ribonuclease from Rana catesbeiana (bullfrog) oocytes", Nucl. Acids Res., 1992, 20, 1371-1377.

Lima, W. F. et al., "Highly efficient endonucleolytic cleavage of RNA by a CyszHisz zinc-finger peptide," Proc. Natl. Acad. Sci. USA (1999) 96:10010-10015.

Lima, W.F. et al., "Binding affinity and specificity of Escherichia coli RNase H1: impact on the kinetics of catalysis of antisense oligonucleotide-RNA hybrids," Biochemistry, vol. 36, pp. 390-398 (1997).

Limbach, P.A. et al., "Summary: the modified nucleosides of RNA," Nucleic Acids Res., 1994, 22(12), 2183-2196.

Lin, K.-Y. et al., "Tricyclic 2'-Deoxycytidine Analogs: Synthesis and Incorporation into Oligodeoxynucleotides Which Have Enhanced Binding to Complementary RNA," J. Am. Chem. Soc., 1995, 117, 3873-3874.

Lin, M. et al., "Inhibition of collagenase type I expression by psoralen antisense oligonucleotides in dermal fibroblasts," Faseb J. (1995), 9, 1371-1377.

Lipardi, C., et al., "RNAi as random degradative PCR: siRNA primers convert mRNA into dsRNAs that are degraded to generate new siRNAs," Cell, 2001, 107, 297-307.

Liu, H. et al. "A Four Base Paired Genetic Helix with Expanded Size," Science (2003) 302; 868-871.

Liu, H. et al., "Toward a New Genetic System with Expanded Dimensions: Size-Expanded Analogues of Deoxyadenosine and Thymidine," J. Am Chem Soc. (2004) 126(4) 1102-1109.

Liu, K. et al., "Efficient Nuclear Delivery of Antisense Oligodeoxynucleotides and Selective Inhibition of CETP Expression by Apo E Peptide in a Human CETP-Stably Transfected CHO Cell Line," Arterioscler. Thromb. Vasc. Biol. (1999) 19:2207-2213.

Lixin, R. et al., "Novel Properties of the Nucleolar Targeting Signal of Human Angiogenin," Biochem. Biophys. Res. Comm. (2001) 284:185-193.

Loakes, D. et al., "The applications of universal DNA base analogues," Nucleic Acids Res., 2001, 29(12), 2437-2447.

Lohrmann et al., "New Solid Supports for DNA Synthesis", DNA, 1984, 3, 122.

Lukhtanov, E. A. et al., "Direct, Solid Phase Assembly of Dihydropyrroloindole Peptides with Conjugated Oligonucleotides," Bioconjugate Chem. (1996) 7(5):564-567.

Lund et al., "Assessment of methods for covalent binding of nucleic acids to magnetic beads, Dynabeads™, and the characteristics of the bound nucleic acids in hybridization reactions", Nucl. Acids Res., 1988, 16, 10861-10880.

Mahato et al., "Modulation of gene expression by antisense and antigene Oligodeoxynucleotides and small interfering RNA," Expert Opinion on Drug Delivery, Jan. 2005, 2(1), 3-28.

Manche et al., "Interactions between double-stranded RNA regulators and the protein kinase DAI," Mol. Cell Biol., 1992, 12(11), 5238-5248.

Maniak, M. et al., "Evidence for a feedback regulated back-up promoter which controls permanent expression of a Dictyostelium gene", Nucl. Acids Res., 1990, 18, 5375-5380.

Manoharan, M. et al., "Novel Functionalization of the Sugar Moiety of Nucleic Acids for Multiple Labeling in the Minor Groove," Tetrahedron Letters (1991) 32(49):7171-7174.

Manoharan, M., "2'-Carbohydrate modifications in antisense oligonucleotide therapy: importance of conformation, configuration and conjugation," Biochimica et Biophysica Acta, 1999, 1489, 117-130.

Manoharan, M., "Designer Antisense Oligonucleotides: Conjugation Chemistry and Functionality Placement," Antisense Research and Applications, Crooke and Lebleu, eds., CRC Press Boca Raton. FL, 1993, Chapter 17, 303-349.

Manoharan, M., "Oligonucleotide Conjugates as Potential Antisense Drugs with Improved Uptake, Biodistribution, Targeted Delivery and Mechanism of Action," Antisense & Nucleic Acid Drug Development (2002) 12:103-128.

Manoharan, M., "Oligonucleotide Conjugates in Antisense Technology," Antisense Drug Technology, Principles, Strategies, and Applications, Crooke, S. T. ed., Marcel Dekker, New York, (2001) Chapter 16, 391-467.

Manoharan, M., "RNA interference and chemically modified small interfering RNAs," Current Opinion in Chemical Biology, 2004, 8, 570-579.

Marcus-Sekura, "Comparative inhibition of chloramphenicol acetyltransferase gene expression by antisense oligonucleotide analogues having alkyl phosphotriester, methylphosphonate and phosphorothioate linkages", Nucleic Acids Res., 1987, 15, 5749-5763.

Marcus-Sekura, "Techniques for Using Antisense Oligodeoxyribonucleotides to Study Gene Expression", Anal. Biochemistry, 1988, 172, 289-295.

Markiewicz, et al., "Simultaneous Protection of 3'- and 5'-Hydroxyl Groups of Nucleosides", Nucleic Acid Chemistry, Part 3, pp. 229-231, L.B. Townsend, et al., Eds., J. Wiley and Sons, New York, 1986, 229-231.

Maruenda, H. et al., "Antisense Sequence-Directed Cross-Linking of DNA Oligonucleotides by Mitomycin C," Bioconjugate Chem. (1996) 7(5):541-544.

Maruenda, H. et al., "Antisense sequence-directed cross-linking of RNA oligonucleotides by mitomycin," Anti-Cancer Drug. Des. (1997) 12, 473-479.

Marwick, C., "First "Antisense" Drug Will Treat CMV Retinitis," J. Am. Med. Assoc., 1998, 280(10), 871.

Maskos, U. and Southern, E.M., "Oligonucleotide hybridisations on glass supports: a novel linker for oligonucleotide synthesis and hybridisation properties of oligonucleotides synthesised in situ", Nucl. Acids. Res., 1992, 20, 1679-1684.

Matson, et al., "Biopolymer Synthesis on Polypropylene Supports", Anal. Biochem., 1994, 217, 306-310.

Matsukura, M. et al., "Phosphorothioate Analogs of Oligodeoxynucleotides: Inhibitors of Replication and Cytopathic Effects of Human Immunodeficiency Virus", Proc. Natl. Acad. Sci. USA, 1987, 84, 7706-7710.

McBride, L.J. and Caruthers, M.H., "An Investigation of Several Deoxynucleoside Phosphoramidites Useful for Synthesizing Deoxyoligonucleotides", Tetrahedron Letters, 1983, 24, 245-248.

McCafferey, A.P. et al., "RNA interference in adult mice," Nature, 2002, 418, 38-39.

McIntyre et al., Antisense Res. Dev., 1993, 3, 309-322.

McQueen, C.A. et al., "Effect of Nalidixic Acid on DNA Repair in Rat Hepatocytes," Cell Biol. Toxicol., 1989, 5(2), 201-206.

Meegan, J.M. et al., "Double-Stranded Ribonuclease Coinduced with Interferon", Science, 1989, 244, 1089-1091.

Metelev, V. et al., "Study of antisense oligonucleotide phosphorothioates containing segments of oligodeoxynucleotides and 2'-o-methyloligoribonucleotides," Bioorg. & Med. Chem. Letts., 1994, 4(24), 2929-2934.

Meunier, L. et al., "The nuclear export signal-dependent localization of oligonucleopeptides enhances the inhibition of the protein expression from a gene transcribed in cytosol," Nucleic Acids Res. 1999, 27(13):2730-2736.

Meyer, et al., "Efficient, Specific Cross-Linking and Cleavage of DNA by Stable, Synthetic Complementary Oligodeoxynucleotides", J. Am. Chem. Soc. 1989, 111, 8517-8519.

Mili, S. et al., "Distinct RNP Complexes of Shuttling hnRNP Proteins with Pre-mRNA and mRNA. Candidate Intermediates in Formation and Export of mRNA," Mol. Cell Biol. (2001) 21(21):7307-7319.

Miller, et al., "A New Approach to Chemotherapy Based on Molecular Biology and Nucleic Acid Chemistry: Matagen (Masking Tape for Gene Expression", Anti-Cancer Drug Design, 1987, 2, 117-128.
Miller, et al., "Biochemical and Biological Effects of Nonionic Nucleic Acid Methylphosphonates", Biochemistry 1981, 20, 1874-1880.
Miller, et al., "Nonionic nucleic acid analogues. Synthesis and characterization of dideoxyribonucleoside methylphosphonates", Biochemistry 1979, 18, 5134-5143.
Miller, et al., "Synthesis and properties of adenine and thymine nucleoside alkyl phosphotriesters, the neutral analogs of dinucleoside monophosphates", J. Am. Chem. Soc. 1971, 93, 6657-6664.
Milligan, "Current concepts in antisense drug design," J. Med. Chem., 1993, 36, 1923-1937.
Miura et al., "Fluorometric determination of total mRNA with oligo(dT) immobized on microtiter plates", Clin. Chem., 1996, 42(11), 1758-1764.
Monia, et al., "Antitumor activity of a phosphorothioate antisense oligodeoxynucleotide targeted against c-raf kinase", Nature Medicine, 1996, 2, 668-675.
Monia, et al., "Evaluation of 2'-Modified Oligonucleotides Containing 2'-Deoxy Gaps as Antisense Inhibitors of Gene Expression", J. Biol. Chem., 1993, 268, 14514-14522.
Monia, et al., "Selective Inhibition of Mutant Ha-ras mRNA Expression by Antisense Oligonucleotides", J. Biol. Chem., 1992, 267, 19954-19962.
Moran, S. et al., "A thymidine triphosphate shape analog lacking watson-crick pairing ability is replicated with high sequence selectivity," Proc. Natl. Acad. Sci. USA (1997) 94 10506-10511.
Moran, S. et al., "Difluorotoluene, a Nonpolar Isostere for Thymine, Codes Specifically and Efficiently for Adenine in DNA Replication," J Am Chem Soc. (1997) 119(8) 2056-2057.
Moulds, C. et al., "Site and Mechanism of Antisense Inhibition by C-5 Propyne Oligonucleotides," Biochemistry, 1995, 34(15), 5044-5053.
Napoli, C. et al., "Introduction of a Chimeric Chalcone Synthase Gene into Petunia Results in Reversible Co-Suppression of Homologous Genes in trans," Plant Cell, 1990, 2(4), 279-289.
Narhi, et al., "Hydrophobic Interaction Chromatography in Alkaline pH", Anal. Biochem., 1989, 182, 266-270.
Nellen, W., C., "What makes an mRNA anti-sense-itive?", Curr. Opin. Cell. Biol., 1993, 18, 419-424.
Nellen, W., et al., "Mechanisms of gene regulation by endogenous and artificially introduced antisense RNA", Biochem., Soc. Trans., 1992, 20, 750-754.
Nelson, P. S. et al., "Bifunctional oligonucleotide probes synthesized using a novel CPG support are able to detect single base pair mutations," Nucleic Acids Res. (1989) 17(18):7187-7194.
Nestle, F.O. et al., "Cationic Lipid is not Required for Uptake and Selective Inhibitory Activity of ICAM-1 Phosphorothioate Antisense Oligonucleotides in Keratinocytes," J. Invest. Dermatol., 1994, 103, 569-575.
Nitta, et al., "Purification and Some Properties of Ribonuclease from *Xenopus laevis* Eggs", Biol. Pharm. Bull. (Jpn.), 1993, 16, 353-356.
Noguchi, et al., "Characterization of an Antisense Inr Element in the eIF-2αGene", J. Biol. Chem., 1994, 269, 29161-29167.
Noyes, et al., "Nucleic Acid Hybridization Using DNA Covalently Coupled to Cellulose", Cell, 1975, 5, 301-310.
Nykänen, A. et al, "ATP Requirements and Small Interfering RNA Structure in the RNA Interference Pathway," Cell, 2001, 107, 309-321.
Ohtsuka et al., "Recognition by Restriction Endonuclease EcoRI of Deoxyoctanucleotides containing modified sugar moieties," Eur. J. Biochem., Mar. 1984, 447-450.
Ohtsuki, et al., "Isolation and purification of double-stranded ribonuclease from calf thymus", J. Biol. Chem., 1977, 252, 483-491.
Olie, R.A. et al., "Analysis of ribosyl-modified, mixed backbone analogs of a bcl-2/bcl-xL antisense oligonucleotide," Biochimica et Biophysica Acta, 1576 (2002), 101-109.
Olsen, D.B., et al., "Study of a Hammerhead Ribozyme Containing 2'-Modified Adenosine Residues," Biochemistry, 1991, 30:, 9735-9741.

O'Neill, B.M. et al., "A Highly Effective Nonpolar Isostere of Deoxyguanosine: Synthesis, Structure, Stacking, and Base Pairing," J. Org. Chem. (2002) 67(17):5869-5875.
Opalinska et al., "Nucleic-acid therapeutics: basic principles and recent applications," Nature Review, 2002, 1, 503-514.
Outten, et al., "Synthetic 1-methoxybenzo[d]naphtho[1,2-b]pyran-6-one c-glycosides", J. Org. Chem. 1987, 52, 5064-5066.
Owen, et al., "Transcriptional activation of a conserved sequence element by ras requires a nuclear factor distinct from c-fos or c-jun", Proc. Natl. Acad. Sci USA, 1990, 87, 3866-3870.
Paddison, P.J., et al., "Stable suppression of gene expression by RNAi in mammalian cells," PNAS, 2002, 99(3), 1443-1448.
Parker, J.S. et al., "Structure insights into mRNA recognition from a PIWI domain-siRNA guide complex," Nature, 2005, 434, 663-666.
Parkes, et al., "A short synthesis of 3'-cyano-3'-Deoxythymidine", Tetra. Lett., 1988, 29, 2995-2996.
Parr, W. et al., "Solid-Phase Peptide Synthesis on an Inorganic Matrix having Organic Groups on the Surface," Angew Chem. Internat. Edit, 1972, 11 (4), 314-315.
Patzel et al., "A Theoretical Approach to Select Effective Antisense Oligodeoxyribonucleotides at High Statistical Probability," Nucleic Acids Research (1999) pp. 4328-4334.
Pease, et al., "Light-generated oligonucleotide arrays for rapid DNA sequence analysis", Proc. Natl. Acad. Sci. USA, 1994, 91, 5022-5026.
Peracchi, A., "Prospects for antiviral ribozymes and deoxyribozymes," Rev. Med. Virol., vol. 14, pp. 47-64 (2004).
Petersheim, et al., "Base-Stacking and Base-Pairing contributions to helix stability: thermodynamics of double-helix formation with CCGG, CCGGp, CCGGAp, ACCGGp, CCGGUp, and ACCGGUp", Biochemistry, 1983, 22, 256-263.
Pichon, C. et al., "Intracellular Routing and Inhibitory Activity of Oligonucleopeptides Containing a KDEL Motif," Mol. Pharmacol. (1997) 51:431-438.
Pieken, W.A. et al., "Kinetic Characterization of Ribonuclease-Resistant 2'-Modified Hammerhead Ribozymes," Science, 1991, 253, 314-317.
Pieken, W.A., et al., "Structure-Function Relationship of Hammerhead Ribozymes as Probed by 2'-Modifications," Nucleic Acids Symp Ser., 1991, 24, 51-53.
Pike et al., "Mixed Alkylation (Methylation and Ethylation) of Adenosine by Diazoethane in Aqueous 1,2-Dimethoxyethane," J. Org. Chem., 1974, 39(25), 3674-3676.
Pilet, J. et al., "Structural parameters of single and double helical polyribonucleotides," Biochem Biophys Res Commun, 1973, 52(2), 517-523.
Pitts, A.E. et al., "Inhibition of human telomerase by 2'-O-methyl-RNA," Proc. Natl. Acad. Sci. USA, 1998, 95, 11549-11554.
Pon, et al., "Derivatization of Controlled Pore Glass Beads for Solid Phase Oligonucleotide Synthesis", BioTech., 1988, 6, 768-773.
Poopeiko, N.E. et al., "*Xylo*-configured Oligonucleotides (XNA, Xylo Nucleic Acid): Synthesis of Conformationally Restricted Derivatives and Hybridization Towards DNA and RNA Complements," Biorganic & Medicinal Chemistry Letters 2003, vol. 13, pp. 2285-2290.
Porta, H. et al., "An allosteric hammerhead ribozyme," Biotechnology (N.Y.), 1995, 13(2), 161-164.
Prakash, T. P. et al., Abstract of the 227th ACS National Meeting, Anaheim,CA, Mar. 28-Apr. 1, 2004.
Prakash, T. P. et al., "Synthesis of Site-Specific Oligonucleotide-Polyamine Conjugates," Bioorg. Med. Chem. Lett. (1994) 4(14):1733-1738.
Prokipcak, et al., "Purification and Properties of a Protein that Binds to the C-terminal Coding Region of Human c-myc mRNA", J. Biol. Chem., 1994, 269, 9261-9269.
Puglisi, et al., "Absorbance melting curves of RNA", Methods in Enzymology, 1989, 180, 304-325.
Rajur, S. B. et al., "Covalent Protein-Oligonucleotide Conjugates for Efficient Delivery of Antisense Molecules," Bioconjugate Chem. (1997) 8(6):935-940.
Rajwanshi, V.K., et al., "LNA stereoisomers: xylo-LNA (α-D-xylo configured locked nucleic acid) and β-L-ribo configured locked nucleic acid)," Chem. Commun., 1999, 1395-1396.

Ranganathan, "Modification of the 21-Position of Purine Nucleosides: Synthesis of 21-a-Substituted-21-Deoxyadenosine Analogs", Tetrahedron Letters, 1977, 15, 1291-1294.
Ransford et al., "2'-O-Ethyl Pyrimidine Nucleosides," J. Carbohydrates—Nucleosides—Nucleotides, 1974, 1(3), 275-278.
Rao, et al., "A Novel One-step Procedure for the Conversion of Thymidine into 2,3'-Anhydrothymidine", J. Chem. Soc. Chem. Commun., 1989, 997-998.
Rausch, J.W. et al., "Hydrolysis of RNA/DNA hybrids containing nonpolar pyrimidine isosteres defines regions essential for HIV type 1 polypurine tract selection," PNAS (2003) 100(20): 11279-11284.
Reese, C.B., et al., "4-(1,2,4-Triazol-1-yl)-and 4-(3-Nitro-1,2,4-triazol-1-yl)-1-(β-D-Arabinofuranosyl)cytosine(Ara-C)", J. Chem. Soc. Perkin Trans. I, 1982, pp. 1171-1176.
Revankar et al., "Synthesis and Antiviral/Antitumor of Certain 3-Seazaguanine Nucleosides and Nucleotides", J. Med. Chem. 1984, 24, 1389-1396.
Rhodes, J. et al., "Therapeutic potentiation of the immune system by costimulatory Schiff-baseforming drugs," Nature (1995) 377(6544):71-75.
Robins, et al., "Nucleic acid related compounds. 41. Restricted furanose conformations of 3',5'-O(1,1,3,3-tetraisoprpyldisilox-1,3-diy1)nucleosides provide a convenient evaluation of anomeric configuration1,2", Can. J. Chem., 1983, 61, 1911-1920.
Robins, et al., "Nucleic Acid Related Compounds. 42. A General Procedure for the Efficient Deoxygenation of Secondary Alcohols. Regiospecific and Stereoselective Conversion of Ribonucleosides to 2'-Deoxynucleosides", J. Am. Chem. Soc., 1983, 105, 4059-4065.
Robins, et al., "Synthesis of 2'-Deoxytubercidin, 2'-Deoxyadenosine, and Related 2'-Deoxynucleosides via a Novel Direct Stereospecific Sodium Salt Glycosylation Procedure", J. Am. Chem. Soc., 1984, 106, 6379-6382.
Roelen et al., "Synthesis of Nucleic Acid Methylphos-Phonothioates", Nucleic Acids Research 1988, 16(15), 7633-7645.
Rottman et al., "Influence of 2'-O-Alkylation on the Structure of Single-Stranded Polynucleotides and the Stability of 2'-O-Alkylated Polynucleotide Complexes," Biochem., 1974, 13, 2762-2771.
Rottman, F. et al., "Polymers Containing 2'-O-Methylnucleotides. II. Synthesis of Heteropolymers," Biochem, 1969, 8(11), 4354-4361.
Rottman, F. et al., "Polynucleotides Containing 2'-0-Methyladenosine. I. Synthesis by Polynucleotide Phosphorylase," Biochem, 1968, 7, 2634-2641.
Ruby, et al., "An Early Hierarchic Role of U1 Small Nuclear Ribonucleoprotein in Splicesome Assembly", Science, 1988, 242, 1028-1035.
Rump, E. T. et al., "Preparation of Conjugates of Oligodeoxynucleotides and Lipid Structures and Their interaction with Low-Density Lipoprotein," Bioconjugate Chem. (1998) 9(3):341-349.
Ryan, et al., "Synthesis of 2-Thio-D-ribose and 2'-Thioadenosine Derivatives", J. Org. Chem., 1971, 36(18), 2646-2657.
Saito, H. and Richardson, C., "Processing of mRNA by Ribonuclease III Regulates Expression of Gene 1.2 of Bacteriophage T7", 1981, Cell, 27, 533-542.
Sambrook, et al., "Molecular Cloning. A Laboratory Manual", Cold Spring Harbor Laboratory Press, 1989, vol. 2, pp. 11.31-11.32.
San et al., "Safety and short term toxicity of a novel cationic lipid formulation for human gene therapy", Human Gene Therapy, 1993, 4, 781-788.
Sands, et al., 'Biodistribution and Metabolism of Internally 3H-Labeled Oligonucleotides. II. 3',5'-Blocked Oligonucleotides, Mol. Pharmacol., 1995, 47, 636-646.
Scaringe, S.A., Thesis entitled, "Design and Development of New Protecting Groups for RNA Synthesis," University of Colorado (1996).
Scherer et al., "Approaches for the sequence-specific knockdown of mRNA," Nat. Biotechnol., 2003, 21(12), 1457-1465.
Schott, "Template-Chromatographie an Stationar Gebundenen Oligonukleotiden", J. Chromatogr., 1975, 115, 461-476.
Schwartz, et al., "A microtransfection method using the luciferase-encoding reporter gene for the assay of human immunodeficiency virus LTR promoter activity", Gene, 1990, 88, 197-205.
Schwarz, D.S. et al., "Asymmetry in the Assembly of the RNAi Enzyme Complex," Cell, 2003, 115(2), 199-208.
Seela, et al., "Palindromic Octa- and Dodecanucleotides Containing 2'-Deoxytubercidin: Synthesis, Hairpin Formation, and Recognition by the Endodeoxyribonuclease", Biochemistry, 1987, 26, 2232-2238.
Seliger, H., et al., "Synthetic Oligonucleotides for Biomedical Applications," Nucleic Acids Symp Ser., 1991, 24:193-196.
Seliger, H., "Handelsubliche Polymere als Trager in der Oligonucleotidsynthese, 1", Die Makromolekulart Chemie, 1975, 176, 1611-1627.
Seliger, H., and Aumann, G., "Trager-Oigonucleotidsynthese an unvernetzten Copolymeren aus Vinylalkohol und N-Vinylpyrrolidon", Die Makromolekulare Chemie, 1975, 176, 609-627
Seliger,H. and Aumann, G., "Oligonucleotide Synthesis on a Polymer Support Soluble in Water and Pyridine", Tetrahedron Letters, 1973, No. 31, 2911-2914.
Shi, Y., "Mammalian RNAi for the masses," Trends in Genetics (2003) 19(1): 9-12.
Shibahara, S. et al., "Inhibition of human immunodeficiency virus (HIV-1) replication by synthetic oligo-RNA derivatives," Nucl. Acids Res., 1989, 17(1), 239-252.
Shuman, S. et al., "Site-specific Interaction of Vaccinia Virus Topoisomerase I with Base and Sugar Moieties in Duplex DNA," J. Biol Chem, 1993, 268, 18943-18950.
Siddell, S.G., "RNA Hybridization to DNA Coupled with Cyanogen-Bromide-Activated Sephadex", Eur. J. Biochem., 1978, 92, 621-629.
Sigman, "Nuclease Activity of 1,10-Phenanthroline-Copper Ion", Acc. Chem. Res., 1986, 19, 180-186.
Sijen, T. et al., "On the role of RNA amplification in dsRNA-triggered gene silencing," Cell, Nov. 16, 2001, 107, 465-476.
Singer et al., "Alkylation of Ribose in RNA Reacted with Ethylnitrosourea at Neutrality," Biochem., 1976, 15(23), 5052-5057.
Smith et al., "Antiviral effect of an oligo(nucleoside methylphosphonate) complementary to the splice junction of herpes simplex virus type 1 immediate early pre-mRNAs 4 and 5", Proc. Natl. Acad. Sci. USA, 1986, 83, 2787-2791.
Smith, et al., "The synthesis of oigonucleotides containing an aliphatic amino group at the 5'terminus: synthesis of fluorescent DNA primers for use in DNA sequence analysis", Nucl. Acids Res., 1985, 13, 2399-2412.
Smith, T.F. et al., "Comparison of Biosequences," Adv. Appl. Math., 1981, 2, 482-489.
Song, E. et al., "RNA interference targeting Fas protects mice from fulmiant hepatitis," Nature Med., 2003, 9(3), 347-351.
Song, J.-J. et al., "The Crystal Structure of Argonaute and Its Implication for RISC Slicer Activity," Science, 2004, 305, 1434-1437.
Song, J.-J. et al., "The crystal structure of the Argonaute2 PAZ domain reveals an RNA binding motif in RNAi effector complexes," Nature Struct. Biol., 2003, 10(12), 1026-1032.
Soutschek, J. et al., "Therapeutic silencing of a endogenous gene by systemic administration of modified siRNAs," Nature, 2004, 432(7014), 173-178.
Sproat, et al., "Highly Efficient Chemical Synthesis of 2'-O-methylioligoribunocleotides and Tetrabiotinylated Derivatives; Novel Probes That are Resistant to Degradation by RNA or DNA Specific Nucleases", Nucleic Acids Research, 1989, 17, 3373-3386.
Sproat, et al., "New synthetic routes to protected purine 2'-O-methylriboside-3'-O-phosphoramidites using a novel alkylation procedure", Nucleic Acids Research, 1990, 18, 41-49.
Stein, C.A. et al., Antisense Oligonucleotides as Therapeutic Agents—Is the Bullet Really Magical?, Science, 1993, 261, 1004-1012.
Stein, et al., "Oligodeoxynucleotides as Inhibitors of Gene Expression: A Review", Cancer Research, 1988, 48, 2659-2668.
Stein, et al., "Physicochemical properties of phosphorothioate oligodeoxynucleotides", Nucleic Acids Research, 1988, 16, 3209-3221.
Stolt, P. and Zillig, W., "Antisense RNA mediates transcriptional processing in an archaebacterium, indicating a novel kind of RNase activity", Mol. Microbiol., 1993, 7, 875-882.

Strickland, et al., "Antisense RNA Directed Against the 3' Noncoding Region Prevents Dormant mRNA Activation in Mouse Oocytes", Science, 1988, 241, 680-684.

Struck, "Vaccine R&D Success Rates and Development Times," Nature Biotechnology, May 1996, 14, 591-593.

Stufkens, et al., "Dynamic Jahn-Teller Effect in the Excited States of SeCl62-, SeBr62-, TeCl62- and TeBr62-", Recueil des Travaux Chimiques des Pays-Bas 1970, 89, 1185-1201.

Stull, et al., "Antigene, Ribozyme and Aptamer Nucleic Acid Drugs: Progress and Prospects", Pharm. Res., 1995, Pharm. Rev., 12, 465-482.

Suciu et al., "Synthesis of 9-(2,5-dideoxy-β-D-glycero-pent-4-enofuranosyl)adenine", Carbohydrate Research, 1975, 44, 112-115.

Sui, G., et al., "A DNA vector-based RNAi technology to suppress gene expression in mammalian cells," PNAS, 2002, 99(8), 5515-5520.

Syvanen, et al., "Quantification of polymerase chain reaction products by affinity-based hybrid collection", Nucl. Acids Res., 1988, 16, 11327-11338.

Szyf, et al., "Growth Regulation of Mouse DNA Methyltransferase Gene Expression", J. Biol. Chem., 1991, 266, 10027-10030.

Tamanini, F. et al., "The fragile X-related proteins FXRIP and FXRZP contain a functional nucleolar-targeting signal equivalent to the HIV-1 regulatory proteins," Hum. Mol. Genet. (2000) 9(10):1487-1493.

Tazawa et al., "A Novel Procedure for the Synthesis of 2'-O-Alkyl Nucleotides" Biochem., 1972, 11(26), 4931-4937.

Thompson,"Applications of Antisense and siRNAs During Preclinical Drug Development," DDT (2002) 7(17): 912-917.

Tidd, D.M. et al., "Evaluation of N-ras oncogene anti-sense, sense and nonsense sequence methylphosphonate oligonucleotide analogues," Anti-Cancer Drug Design, 1988, 3(2), 117-127.

Tosquellas, G. et al., "The pro-oligonucleotide approach: solid phase synthesis and preliminary evaluation of model pro-dodecathymidylates," Nucleic Acids Research, 1998, 26(9), 2069-2074.

Tracewell et al., In Vivo Modulation of Rat Cytochrome P450 1A1 by Double-Stranded Phosphorothioate Oligodeoxynucleotides, Toxicology and Applied Pharmacology, 1995, 135, 179-184.

Tseng et al., "Antisense Oligonucleotide Technology in the Development of Cancer Therapeutics", Cancer Gene Therapy, 1994, 1, 65-71.

Tuschl, T. et al., "Small interfering RNAs: a revolutionary tool for the analysis of gene function and gene therapy," Molecular Interventions, 2002, 2(3), 158-167.

U.S. Appl. No. 60/423,760, filed Nov. 5, 2002, by Baker et al.

Uhlmann et al., "Antisense Oligonucleotides: A New Therapeutic Principle", Chem. Rev., 1990, 90, 543-584.

Van der Krol, et al., "Modulation of Eukaryotic Gene Expression by Complementary RNA or DNA Sequences", BioTechniques, 1988, 6, 958-976.

Van Ness et al., "A versatile solid support system for oligodeoxynucleotide probe-based hybridization assays", Nucleic Acids Research, 1991, 19, 3345-3350.

Veronese et al., "Bioconjugation in pharmaceutical chemistry," II Farmaco, 1999, 54, 497-516.

Vickers, T.A. et al., "Efficient Reduction of Target RNAs by Small Interfering RNA and Rnase H-dependent Antisense Agents," J. Biol. Chem., 2003, 278(9), 7108-7118.

Volk et al., "An antisense transcript from the Xenopus laevis bFGF gene coding for an evolutionariy conserved 24 kd protein", EMBO J., 1989, 8, 2983-2988.

Wada, A. et al., "Nuclear export of actin: a novel mechanism regulating the subcellular localization of a major cytoskeletal protein," EMBO J. (1998) 17:1635-1641.

Walder, et al., "Antisense DNA and RNA: Progress and Prospects", Genes & Development, 1988, 2, 502-504.

Walder, et al., "Role of RNase H in Hybrid-Arrested Translation by Antisense Oligonucleotides", Proc. Natl. Acad. Sci. USA 1988, 85, 5011-5015.

Wang, J., et al., "Syhthesis and binding property of an oligonucleotide containing tetrafluorophenoxazine," Tetrahedron Lett., 1998, 39, 8385-8388.

Wang, X. et al., "Modular Recognition of RNA by a Human Pumilio-Homology Domain," Cell (2002) 110:501-512.

Wei, Z. et al., "Hybridization properties of oligodeoxynucleotide pairs bridged by polyarginine peptides," Nucleic Acids Res. (1996) 24(4):655-661.

Wein, G. et al., "The 3'-UTR of the mRNA coding for the major protein kinase C substrate MARCKS contains a novel CU-rich element interacting with MRNA stabilizing factors HuD and HuR," Eur. l. Biochem. (2003) 270:350-365.

Westermann et al., "Inhibition of expression of SV40 virus large T-antigen by antisense oligodeoxyribonucleotides", Biomed. B. Acta., 1989, 48, 85-93.

Wetlaufer et al., "Surfactant-Mediated Protein Hydrophobic-Interaction Chromatography", J. Chromatography, 1986, 359, 55-60.

Wianny et al., "Specific interference with gene function by double-stranded RNA in early mouse development," Nature Cell Biology (2000) 2: 70-75.

Wilds et al., "2'-Deoxy-2'-fluoro-B-D-arabinonucleosides and oligonucleotides (2'F-ANA): synthesis and phisicochemical studies," Nucleic Acids Res., 2000, 28, 3625-3635.

Williams, D.M., et al., 'Properties of 2'-Fluorothymidine-Containing Oligonucleotides: Interaction with Restriction Endonuclease EcoRV, Biochemistry, 1991, 30, 4001-4009.

Wright, P. et al., "Large Scale Synthesis of Oligonucleotides via Phosphoramidite Nucleosides and a High-loaded Polystyrene Support," Tetrahedron Lett., 1993, 34(21), 3373-3376.

Wu et al., "High Resolution Separation and Analysis of Biological Macromolecules", Methods in Enzymology, 1996, 270, 27-47.

Wu et al., "Purification and Properties of Drosophila Heat Shock Activator Protein", Science, 1987, 238, 1247-1253.

Wu, H. et al., "Identification and partial purification of human double strand RNase activity. A novel terminating mechanism for oligoribonucleotide antisense drugs," J. Biol. Chem, 1998, 273(5), 2532-2542.

Wu, H. et al., "Properties of Cloned and Expressed Human RNase H1," Journal of Biological Chemistry 1999, vol. 274, pp. 28270-28278.

Yang, Y. et al., "HIV-1 TAT-mediated protein transduction and subcellular localization using novel expression vectors," FEBS Letters (2002) 532, 36-44.

Yashima et al., "High-performance affinity chromatography of oligonucleotides on nucleic acid analogue immobilized silica gel columns", J. Chromatog., 1992, 603, 111-119.

Yasuda et al., "Purification and characterization of a ribonuclease from human spleen", Eur. J. Biochem., 1990, 191, 523-529.

Yeung, et al., "Photoreactives and Thermal Properties of Psoralen Cross-Links", Biochemistry 1988, 27, 3204-3210.

Yu, D. et al., "Hybrid oligonucleotides: synthesis, biophysical properties, stability studies, and biological activity," Bioorganic and Medicinal Chemistry, 1996, 4(10), 1685-1692.

Yu, J.-Y., et al., "RNA interference by expression of short-interfering RNAs and hairpin RNAs in mammalian cells," PNAS, 2002, 99(9), 6047-6052.

Yu, Y.T. et al., "A new method for detecting sites of 2'-O-methylation in RNA molecules," RNA, 1997, 3(3), 324-331.

Zamecnik, P.C. et al., "Inhibition of Rous sarcoma virus replication and cell transformation by a specific oligodeoxynucleotide," Proc. Natl. Acad. Sci. USA, 1978, 75(1), 280-284.

Zamore, P.D. et al., "Ancient Pathways Programmed by Small RNAs," Science, 2002, 296, 1265-1269.

Zamore, P.D. et al., "RNAi: Double-Stranded RNA Directs the ATP-Dependent Cleavage of mRNA at 21 to 23 Nucleotide Intervals," Cell, 2000, 101, 25-33.

Zanta, M. A. et al., "Gene delivery: A single nuclear localization signal peptide is sufficient to carry DNA to the cell nucleus," Proc. Natl. Acad. Sci. USA (1999) 96:91-96.

Zarytova, et al., "Affinity Chromatography of DNA Fragments and P-Modified Oligonucleotides", Analyt. Biochem., 1990, 188, 214-218.

Zhang et al., "Single Processing Center Models for Human Dicer and Bacterial RNase III," Cell, 2004, 118, 57-68.

Zhang et al., "Targeted Gene Silencing by Small Interfering RNA-Based Knock-Down Technology," Current Pharmaceutical Biotechnology, 2004, 5, 1-7.

Zhang, H. et al., "Reduction of liver Fas expression by an antisense oligonucleotide protects mice from fuminant hepatitis," Nature Biotech., 2000, 18, 862-867.

Zhang, Z. et al., "Uptake of N-(4'-pyridoxyl)amines and release of amines by renal cells: A model for transporter-enhanced delivery of bioactive compounds," Proc. Natl. Acad. Sci. USA (1991) 88:10407-10410.

Zhao, Q. et al., "Effect of Different Chemically Modified Oligodeoxynucleotides on Immune Stimulation," Biochemical Pharmacology, 1996, 51, 173-182.

Zhou, Y., et al., "Post-transcriptional suppression of gene expression in xenopus embryos by small interfering RNA," Nucleic Acids Res., 2002, 30(7), 1664-1669.

Zhu, T. et al., "Oligonucleotide-Poly-L-omithine Conjugates: Binding to Complementary DNA and RNA." Antisense Res. Dm. 119931 3:265-275, (1993).

Zmudzka, B. et al., "Poly 2'-0-methylcytidylic acid and the role of the 2'-hydroxyl in polynucleotide structure," Biochem Biophys Res Commun, 1969, 37(6), 895-901.

Zon, "Oligonucleotide Analogues as Potential Chemotherapy Agents", Pharm. Res., 1988, 5(9), 539-549.

Zon, "Synthesis of Backbone-Modified DNA Analogues for Biological Applications", J. Protein Chemistry, 1987, 6, 131-145.

Zuckermann, et al., "Efficient methods for attachment of thiol specific probes to the 3'-ends of synthetic oligodeoxyribonucleotides," Nucleic Acids Research, 1987, 15, 5305-5321.

Zuckermann, R. N. et al., "Site-Selective Cleavage of RNA by a Hybrid Enzyme," J. Am. Chem. SOC. (1988) 110:1614-1615.

U.S. Appl. No. 09/315,298, filed May 20, 1999, Teng et al.

Abe, A. et al., "Conformational Energies and the Random-Coil Dimensions and Dipole Moments of the Polyoxides $CH_3O[(CH_2)_yO]_xCH_3$," J. Am. Chem. Soc. (1976) 98(21):6468-6476.

Altmann, K.-H. et al., "Second generation antisense oligonucleotides: structure-activity relationships and the design of improved signal-transduction inhibitors," Biochem. Soc. Trans. 24:630-637. (1996).

Altmann, K.-H. et al., "Second Generation of Antisense Oligonucleotides: From Nuclease Resistance to Biological Efficacy in Animals," Chimica (1996) 50:168-176.

Altmann, K.-H. et al., "Second Generation Antisense Oligonucleotides—Inhibition of PKC-a and c-RAF Kinase Expression by Chimeric Oligonucleotides Incorporating 6'-Substituted Carbocyclic Nucleosides and 2'-O-Ethylene Glycol Substituted Ribonucleosides," Nucleosides Nucleotides (1997) 16(7-9):917-926.

Altschul, S. F. et al. "Basic Local Alignment Search Tool," J. Mol. Biol. (1990) 215:403-410.

Arnott, S. et al., "Optimised Parameters for A-DNA and B-DNA," Biochem. Biophys. Res. Comm. (1972) 47(6):1504-1509.

Baker, B. F. et al., "2'-O-(2-Methoxy)ethyl-modified Anti-intercellular Adhesion Molecule I (ICAM-I) Oligonucleotides Selectively Increase the ICAM-I mRNA Level and Inhibit Formation of the ICAM-I Translation Initiation Complex in Human Umbilical Vein Endothelial Cells," J. Biol. Chem. (1997) 272(18):11994-12000.

Bass, B. L., "Double-Stranded RNA as a Template for Gene Silencing," Cell (2000) 101:235-238.

Beaucage, S. L. et al., "Deoxynucleoside Phosphoramidites—A New Class of Key Intermediates for Deoxypolynucleotide Synthesis," Tetrahedron Lett. (1981) 22(20):1859-1862.

Berger, I. et al., "Crystal structures of B-DNA with incorporated 2'-deoxy-2'-fluoro-arabino-furanosyl thymines: implications of conformational preorganization for duplex stability," Nucleic Acids Res. (1998) 26(10):2473-2480.

Boutla, A. et al., "Short 5'-phosphorylated double-stranded RNAs induce RNA interference in Drosophila," Current Biol. (2001) 11:1776-1780.

Braasch, D. A. et al., "Locked nucleic acid (LNA): fine-tuning the recognition of DNA and RNA," Chem. Biol. (2001) 8:1-7.

Braasch, D. A. et al., "Antisense inhibition of gene expression in cells by oligonucleotides incorporating locked nucleic acids: effect of mRNA target sequence and chimera design," Nucleic Acids Res. (2002) 30(23):5160-5167.

Braasch, D. A. et al., "Novel Antisense and Peptide Nucleic Acid Strategies for Controlling Gene Expression," Biochem. (2002) 41(14):4503-4510.

Brantl, S., "Antisense-RNA regulation and RNA intereference,"Biochim. Biophys. Acta (2002) 1575:15-25.

Brazma, A. et al., "Gene expression data analysis," FEBS Letters (2000) 480:17-24.

Carulli, J. P. et al., "High Throughput Analysis of Differential Gene Expression," J. Cell. Biochem. Suppl. (1998) 30/31:286-296.

Celis, J. E. et al.. "Gene expression profiling: monitoring transcription and translation products using DNA microarrays and proteomics," Febs Lett. (2000) 480:2-16.

Chaput, J. C. et al., "DNA Polymerase-Mediated DNA Synthesis on a TNA Template," J. Am. Chem. Soc. (2003) 125(4):856-857.

Chiu,Y.-L. et al., "siRNA function in RNAi: A chemical modification analysis," RNA (2003) 9:1034-1048.

Conte, M. R. et al., "Conformational properties and thermodynamics of the RNA duplex $r(CGCAAAUUUGCG)_2$: comparison with the DNA analogue $d(CGCAAATTTGCG)_2$," Nucleic Acids Res. (1997) 25(13):2627-2634.

Cornell, W. D. et al., "A Second Generation Force Field for the Simulation of Proteins, Nucleic Acids, and Organic Molecules," J. Am. Chem. Soc. (1995) 117(19):5179-5197.

Crooke, S. T. et al., "Pharmacokinetic Properties of Several Novel Oligonucleotide Analogs in mice," J. Pharmacol. Exp. Ther. (1996) 277(2):923-937.

Dahl, B. H. et al., "A Flighty Reactive, Odourless Substitute for Thiphenol/Triethylmaine as a Deprotection Reagent in the Synthesis of Oligonucleotides and their Analogues," Acta Chem. Scand. (1990) 44:639-641.

Dellinger, D. J. et al., "Solid-Phase Chemical Synthesis of Phosphotioacetate and Thiophosphonoacetate Oligodeoxynucleotides," J. Am. Chem. Soc. (2003) 125(4):940-950.

Egli, M. et al., "RNA Hydration: A Detailed Look," Biochemistry (1996) 35(26):8489-8494.

Elayadi, A. N. et al., "Application of PNA and LNA oligomers to chemotherapy," Curr. Opin. Investig. Drugs (2001) 2(4):558-561.

Elbashir, S. M. et al., "RNA interference is mediated by 21- and 22-nucleotide RNAs," Genes Dev. (2001) 15:188-200.

Elbashir, S. M. et al., "Functional anatomy of siRNAs for mediating efficient RNAi in Drosophila melanogaster embryo lysate," Embo J (2001) 20(23):6877-6888.

Elbashir, S. M. et al., "Duplexes of 21-nucleotide RNAs mediate RNA interference in cultured mammalian cells," Nature (2001) 411:494-498.

Englisch, U. et al., "Chemically Modified Oligonucleotides as Probes and Inhibitors," Angew. Chem. Int. Ed. Engl. (1991) 30:613-629.

Faria, M. et al., "Phosphoramidate oligonucleotides as potent antisense molecules in cells and in vivo," Nature Biotech. (2001) 19:40-44.

Fedoroff, O. Y. et al., "Structure of a DNA:RNA Hybrid Duplex," J. Mol. Biol. (1993) 233:509-523.

Fire, A. et al., "Potent and specific genetic interference by double-stranded RNA in Caenorhabditis elegans," Nature (1998) 391:806-811.

Flanagan, W. M. et al., "A cytosine analog that confers enhanced potency to antisense oligonucleotides," Proc. Natl. Acad. Sci. USA (1999) 96:3513-3518.

Fluiter, K. et al., "In vivo tumor growth inhibition and biodistribution studies of locked nucleic acids (LNA) antisense oligonucleotides," Nucleic Acids Res. (2003) 31(3):953-962.

Freier, S. M. et al., "The ups and downs of nucleic acid duplex stability: structure-stability studies on chemically-modified DNA:RNA duplexes," Nucleic Acids Res. (1997) 25(22):4429-4443.

Frieden, M. et al., "Expanding the design horizon of antisense oligonucleotides with alpha-L-LNA," Nucleic Acids Res. (2003) 31(21):6365-6372.

Fromageot, H. P. M. et al., "The Synthesis of Oligonucleotides," Tetrahedron (1967) 23:2315-2331.

Fuchs, B. et al., "Identification of Differentially Expressed Genes by Mutually Subtracted RNA Fingerprinting," *Anal. Biochem.* (2000) 286:91-98.

Gait, M. J., "Oligoribonucleotides,"*Antisense Research and Applications* (1993) Crooke, S. T. and Lebleu, B. (eds.), CRC Press, Boca Raton, pp. 289-301.

Gait, M. J. et al., "Application of chemically synthesized RNA," *RNA: Protein Interactions* (1998) Smith (ed.), pp. 1-36.

Gallo, M. et al., "2'-C-Methyluridine Phosphoramidite: a new building block for the preparation of RNA analogues carrying the 2'-hydroxyl group," *Tetrahedron* (2001) 57:5707-13.

Going, J. J. et al., "Molecular Pathology and Future Developments," *Eur. J. Cancer* (1999) 35(14):1895-1904.

González, C. et al., "Structure and Dynamics of a DNA•RNA Hybrid Duplex with a Chiral Phosphorothioate Moiety: NMR and Molecular Dynamics with Conventional and Time-Averaged Restraints," *Biochem.* (1995) 34(15):4969-4982.

Griffin, B. E. et al., "The Synthesis of Oligoribonucleotides," *Tetrahedron* (1967) 23:2301-2313.

Gryaznov, S. et al., "Oligdeoxynucleotide N3'→P5' Phosphoramidates: Synthesis and Hybridization Properties," *J. Am. Chem. Soc.* (1994) 116(7):3143-3144.

Guillerm, D. et al., "Synthesis of 4'-Fluoroadenosine as an Inhibitor of S-Adenosyl-L-Homocysteine Hydrolase,"*Bioorg. Med. Chem. Lett.* (1995) 5(14):1455-1460.

Hakimelahi, G. H. et al., "High Yield Selective 3'-Silylation of Ribonucleosides," *Tetrahedron Lett.* (1981) 22(52):5243-5246.

Harry-O'Kuru, R. E. et al., "A Short, Flexible Route toward 2'-C-Branched Ribonucleosides," *J Org. Chem.* (1997) 62(6):1754-1759.

Heasman, J. "Morpholino Oligos: Making Sense of Antisense?" *Dev. Biol.* (200) 243:209-214, 2002.

Horton, N. C. et al., "The Structure of an RNA/DNA Hybrid: A Substrate of the Ribonuclease Activity of HIV-1 Reverse Transcriptase," *J. Mol. Biol.* (1996) 264:521-533.

Jacobson, K. A. et al., "Methanocarba Analogues of Purine Nucleosides as Potent and Selective Adenosine Receptor Agonists," *J. Med. Chem.* (2000) 43(11):2196-2203.

Jones, S. S. et al., "Migration of t-Butyldimethylsilyl Protecting Groups,"*J.C.S. Perkin I* (1979):2762-2764.

Jungblut, P. R. et al., "Proteomics in human disease: Cancer, heart and infections diseases," *Electrophoresis* (1999) 20:2100-2110.

Jurecic, R. et al., "Long-distance DD-PCR and cDNA microarrays," *Curr. Opin. Microbiol.* (2000) 3:316-321.

Kabanov, A. V. et al., "A new class of antivirals: antisense oligonucleotides combined with a hydrophobic substituent effectively inhibit influenza virus reproduction and synthesis of virus-specific proteins in MDCK cells," *FEBS Lett.* (1990) 259(2):327-330.

Kawasaki, A. M. et al., "Uniformly Modified 2'-Deoxy-2'-fluoro Phosphorothioate Oligonucleotides as Nuclease-Resistant Antisense Compounds with High Affinity and Specificity for RNA Targets," *J. Med. Chem.* (1993) 36(7):831-841.

Koshkin, A. A. et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition," *Tetrahedron* (1998) 54:3607-3630.

Koshkin, A. A. et al., "LNA (Locked Nucleic Acid): An RNA Mimic Forming Exceedingly Stable LNA:LNA Duplexes," *J. Am. Chem. Soc.* (1998) 120(50):13252-13253.

Kroschwitz, J. I. (ed.), "Polynucleotides," *Concise Encyclopedia of Polymer Science and Engineering* (1990) John Wiley & Sons, New York, pp. 858-859.

Kumar, R. et al., "The First Analogues of LNA (Locked Nucleic Acids): Phosphorothioate-LNA and 2'-Thio-LNA," *Bioorg. Med. Chem. Lett.* (1998) 8:2219-2222.

Kurchavov, N. A. et al., "A New Phosphoramidite Reagent for the Incorporation of Diazaphenoxazinone Nucleoside with Enhanced Base-Pairing Properties into Oligodeoxynucleotides," *Nucleosides Nucleotides* (1997) 16(10&11):1837-1846.

Lacerra, G. et al., "Restoration of hemoglobin a synthesis in erythroid cells from peripheral blood of thalassemic patients," *PNAS* (2000) 97(17):9591-9596.

Lane, A. N. et al., "NMR assignments and solution conformation of the DNA•RNA hybrid duplex d(GTGAACTT)•r(AAGUUCAC)," *Eur. J. Biochem.* (1993) 215:297-306.

Larson, E. J. et al., "Rapid DNA Fingerprinting of Pathogens by Flow Cytometry," *Cytometry* (2000) 41:203-208.

Larsson, M. et al., "High-throughput protein expression of cDNA products as a tool in functional genomics," *J. Biotech.* (2000) 80:143-157.

Lee, K. et al., Ring-Constrained (N)-Methanocarba Nucleosides as Adenosine Receptor Agonists: Independent 5'-Uronamide and 2'-Deoxy Modifications, *Bioorg. Med. Chem. Lett.* (2001) 11:1333-1337.

Lesnik, E. A. et al., "Relative Thermodynamic Stability of DNA, RNA and DNA:RNA Hybrid Duplexes: Relationship with Base Composition and Structure," *Biochem.* (1995) 34(34):10807-10815.

Letsinger, R. L. et al., "Cholesteryl-conjugated oligonucleotides: Synthesis, properties, and activity as inhibitors of replication of human immunodeficiency virus in cell culture," *Proc. Natl. Acad. Sci. USA* (1989) 86:6553-6556.

Lin, K.-Y. et al., "Tricyclic 2'-Deoxycytidine Analogs: Syntheses and Incorporation into Oligdcoxynuclcotides Which Have Enhanced Binding to Complementary RNA," *J. Am. Chem. Soc.* (1995) 117(13):3873-3874.

Lin, K.-Y. et al., "A Cytosine Analogue Capable of Clamp-Like Binding to a Guanine in Helical Nucleic Acids," *J. Am. Chem. Soc.* (1998) 120(33):8531-8532.

Madden, S. L. et al., "Serial analysis of gene expression: from gene discovery to target identification," *DDT* (2000) 5(9):415-425.

Manoharan, M. et al., "Chemical Modifications to Improve Uptake and Bioavailability of Antisense Oligonucleotides," *Ann. N.Y. Acad. Sci.* (1992) 660:306-309.

Manoharan, M. et al., "Introduction of a Lipophilic Thioether Tether in the Minor Groove of Nucleic Acids for Antisense Applications," *Bioorg. Med. Chem. Lett.* (1993) 3(12):2765-2770.

Manoharan, M. et al., "Cholic Acid-Oligonucleotide Conjugates for Antisense Applications," *Bioorg. Med. Chem. Lett.* (1994) 4(8):1053-1060.

Manoharan, M. et al., "Oligonucleotide Conjugates: Alteration of the Pharmacokinetic Properties of Antisense Agents," *Nucleosides Nucleotides* (1995) 14(3-5):969-973.

Manoharan, M. et al., "Lipidic Nucleic Acids." *Tetrahedron Letters* (1995) 36(21):3651-3654.

Martin, P., "Ein neuer Zugang zu 2'-O-Alkylribonucleosiden and Eigenschaften deren Oligonucleotide," *Helv. Chim. Acta* (1995) 78:486-504.

Martinez, J. et al., "Single-Stranded Antisense siRNAs Guide Target RNA Cleavage in RNAi," *Cell* (2002) 110:563-574.

Matteucci, M. D. et al., "Synthesis of Deoxyoligonucleotides on a Polymer Support," *J. Am. Chem. Soc.* (1981) 103(11):3185-3191.

Mellitzer, G. et al., "Spatial and temporal 'knock down' of gene expression by eleotroporation of double-stranded RNA and morpholinos into early postimplantation mouse embryos," *Mech. Dev.* (2002) 118:57-63.

Mishra, R. K. et al., "Improved leishmanicidal effect of phosphorothioate antisense oligonucleotides by LDL-mediated delivery," *Biochim. Biophys. Acta* (1995) 1264:229-237.

Montgomery, M. K. et al., "RNA as a target of double-stranded RNA-mediated genetic interference in *Caenorhabditis elegans*," *Proc. Natl. Acad. Sci. USA* (1998) 95:15502-15507.

Morita, K. et al., "2'-O,4'-C-Ethylene-Bridged Nucleic Acids (ENA): Highly Nuclease-Resistant and Thermodynamically Stable Oligonucleotides for Antisense Drug," *Bioorg. Med. Chem. Lett.* (2002) 12:73-76.

Morita, K. et al., "Synthesis and Properties of 2'-O,4'-C-Ethylene-Bridged Nucleic Acids (ENA) as Effective Antisense Oligonucleotides," *Bioorg Med. Chem.* (2003) 11:2211-2226.

Nasevicius, A. et al., "Effective targeted gene 'knockdown' in zebrafish," *Nature Genetics* (2000) 26:216-220.

Nielsen, P. E. et al., "Sequence-Selective Recognition of DNA by Strand Displacement with a Thymine-Substituted Polyamide," *Science* (1991) 254:1497-1500.

Nishikura, K., "A Short Primer on RNAi: RNA-Directed RNA Polymerase Acts as a Key Catalyst," *Cell* (2001) 107:415-418.

Oberhauser, B. et al., "Effective incorporation of 2'-O-methyl-oligoribonucleotides into liposomes and enhanced cell association through modification with thiocholestrol," *Nucleic Acids Res.* (1992) 20(3):533-538.

Ogilvie, K. K. et al., "The Use of Silyl Groups in Protecting the Hydroxyl Functions of Ribonucleosides," *Tetrahedron Letters* (1974) 15(33):2861-2863.

Ørum, H. et al., "Locked nucleic acids: A promising molecular family for gene-function analysis and antisense drug development," *Curr. Opin. Mol. Therap.* (2001) 3(3):239-243.

Owen, G. R. et al., "4'-Substituted Nucleosides. 3. Synthesis of Some 4'-Fluorouridine Derivatives," *J. Org. Chem.* (1976) 41(18):3010-3017.

Parrish, S. et al., "Functional Anatomy of a dsRNA Trigger: Differential Requirement for the Two Trigger Strands in RNA Interference," *Mol. Cell* (2000) 6:1077-1087.

Petersen, M. et al., "The conformations of locked nucleic acids (LNA)," *J. Mol. Recognit.* (2000) 13:44-53.

Pitsch, S., "Protecting Groups for the Synthesis of Ribonucleic Acids," *Chimi* (2001) 55(4):320-324.

Prashar, Y. et al., "Reads: A Method for Display of 3'-End Fragment of Restriction Enzyme-Digested cDNAs for Analysis of Differential Gene Expression," *Methods Enzymol.* (1999) 303:258-272.

Reddy, M. P. et al., "Fast Cleavage and Deprotection of Oligonucleotides," *Tetrahedron Letters* (1994) 35(25):4311-4314.

Reese, C. B. et al., "An Acetal Group Suitable for the Protection of 2'-Hydroxy Functions in Rapid Oligoribonucleotide Synthesis," *Tetrahedron Letters* (1986) 27(20):2291-2294.

Renneberg, D. et al., "Antisense properties of tricyclo-DNA," *Nucleic Acids Res.* (2002) 30(13):2751-2757.

Renneberg, D. et al., "Watson-Crick Base-Pairing Properties of Tricyclo-DNA," *J. Am. Chem. Soc.* (2002) 124(21):5993-6002.

Saison-Behmoaras, T. et al., "Short modified antisense oligonucleotides directed against Ha-*ras* point mutation induce selective cleavage of the mRNA and inhibit T24 cells proliferation," *EMBO J.* (1991) 10(5):1111-1118.

Sanghvi, Y. S. et al., "Heterocyclic Base Modifications in Nucleic Acids and Their Applications in Antisense Oligonucleotides," *Antisense Research and Applications* (1993) CRC Press, Boca Raton, pp. 276-278.

Scaringe, S. A. et al., "Novel RNA Synthesis Method Using 5'-*O*-Silyl-2'-*O*-orthoester Protecting Groups," *J. Am. Chem. Soc.* (1998) 120(45):11820-11821.

Scaringe, S. A., "RNA Oligonucleotide Synthesis via 5'-Silyl-2'-Orthoester Chemistry," *Methods* (2001) 23:206-217.

Schwartz, M. E. et al., "Rapid Synthesis of Oligoribonucleotides Using 2'-*O*-(o-Nitrobenzyloxymethyl)-Protected Monomers," *Bioorg. Med. Chem. Lett.* (1992) 2(9):1019-1024.

Schwarz, D. S. et al., "Evidence that siRNAs Function as Guides, Not Primers, in the *Drosophil* and Human RNAi Pathways,"*Mol. Cell* (2002) 10:537-548.

Searle, M. S. et al., "On the stability of nucleic acid structures in solution: enthalpy-entropy compensations, internal rotations and reversibility," *Nucleic Acids Res.* (1993) 21(9):2051-2056.

Shea, R. G. et al., "Synthesis, hybridization properties and antiviral activity of lipid-oligodeoxynucleotide conjugates," *Nucleic Acids Res.* (1990) 18(13):3777-3783.

Sheehan, D. et al., "Biochemical properties of phosphonoacetate and thiophosphonoactate oligodeoxyribonucleotides," *Nucleic Acids Res.* (2003) 31(14):4109-4118.

Singh, S. K. et al., "Synthesis of 2'-Amino-LNA: A Novel Conformationally Restricted High-Affinity Oligonucleotide Analogue with a Handle," *J. Org. Chem.* (1998) 63(26):10035-39.

Singh, S. K. et al., "LNA (locked nucleic acids): synthesis and high-affinity nucleic acid recognition," *Chem. Commun.* (1998) 455-456.

Skorski, T. et al.. "Antileukemia effect of c-*myc* N3'→P5' phosphoramidate antisense oligonucleotides in vivo," *Proc. Natl. Acad. Sci. USA* (1997) 94:3966-3971.

Steffens, R. et al., "Nucleic-Acid Analogs with Constraint Conformational Flexibility in the Sugar-Phosphate Backbone 'Tricyclo-DNA'," *Helv. Chim. Acta* (1997) 80:2426-2439.

Steffens, R. et al., "Synthesis and Thermodynamic and Biophysical Properties of Tricyclo-DNA." *J. Am. Chem. Soc.* (1999) 121(14):3249-3255.

Sutcliffe. J. G. et al.. "TOGA: An automated parsing technology for analyzing expression of nearly all genes." *PNAS* (2000) 97(5):1976-1981.

Svinarchuk, F. P. et al., "Inhibition of HIV proliferation in MT-4 cells by antisense oligonucleotide conjugated to lipophilic groups," *Biochimie* (1993) 75:49-54.

Tabara, H. et al., "RNAi in *C. elegans*: Soaking in the Genome Sequence," *Science* (1998) 282:430-431.

Tang, X.-Q. et al., "2'-*C*-Branched Ribonucleosides: Synthesis of the Phosphoramidite Derivatives of 2'-*C*-β-Methylcytidine and Their Incorporation into Oligonucleotides," *J. Org. Chem.* (1999) 64(3):747-754.

Tijsterman. M. et al., "RNA Helixase MUT-14-Dependent Gene Silencing Triggered in *C. elegans* by Short Antisense RNAs." *Science* (2002)295:694-697.

Timmons, L. et al., "Specific interference by ingested dsRNA," *Nature* (1998) 395:854.

Timmons. L. et al.. "Ingestion of bacterially expressed dsRNAs can produce specific and potent genetic interference in *Caenorhabditis elegans,*" *Gene* (2001) 263:103-112.

To, K.-Y., "Identification of Differential Gene Expression by High Throughput Analysis," *Comb. Chem. High Throughput Screen.* (2000) 3:235-241.

Tuschl, T. et al., "Targeted mRNA degradation by double-stranded RNA in vitro," *Genes Dev.* (1999) 13:3191-3197.

Wahlestedt, C. et al., "Potent and nontoxic antisense oligonucleotides containing locked nucleic acids," *PNAS* (2000) 97(10):5633-5638.

Wang, J. et al., "Synthesis and binding property of an oligonucleotide containing tetrafluorophenoxazine," *Tetrahedron Letters* (1998) 39:8385-8388.

Wang, J. et al., "Cyclohexene Nucleic Acids (CeNA): Serum Stable Oligonucleotides that Activate RNase H and Increase Duplex Stability with Complementary RNA," *J. Am. Chem. Soc.* (2000) 122(36):8595-8602.

Wengel, J. et al., "LNA (Locked Nucleic Acids)," *Nucleosides & Nucleotides* (1999) 18(6&7):1365-1370.

Wincott, F. et al., "Synthesis, deprotection, analysis and purification of RNA and ribozymes," *Nucleic Acids Res.* (1995) 23(14):2677-2684.

Wolfe, S., "The Gauche Effect. Some Stereochemical Consequences of Adjacent Electron Pairs and Polar Bonds,"*Acc. Chem. Res.* (1972) 5:102-111.

Wouters, J. et al., "5-Substituted Pyrimidine 1,5-Anhydronhexitols: Conformational Analysis and Interaction with Viral Thymidine Kinase," *Bioorg. Med. Chem. Lett.* (1999) 9:1563-1566.

Wu, X. et al., "Base-Pairing Systems Related to TNA: α-Threofuranosyl Oligonucleotides Containing Phosphoramidatc Linkages," *Org. Letters* (2002) 4(8):1279-1282.

Zhang, J. et al., "PowerBLAST: a New Network BLAST Application for Interactive or Automated Sequence Analysis and Annotation," *Genome Res.* (1997) 7:649-656.

\* cited by examiner

PTEN siRNA CONSTRUCTS bold type indicates 2'-MOE, plain text indicates 2'-OH

| Compound (sense_antisense) | Construct (Sense 5'→3' / Antisense) | | IC50 (nM) | Efficacy (% UTC) |
|---|---|---|---|---|
| 357271_357276 | P-5'--AACUAAGGACCAGAGACAA--3'<br>3'--UUGCAUUCCUGGUCUCUGUUU--5'--P | (19mer)<br>(20mer) (SEQ ID NO:19)<br>(SEQ ID NO:12) | 273 | 50 |
| 308746_357275 | 5'--AAGUAAGGACCAGAGACAAA--3'<br>3'--UUCAUUCCUGGCUCUCUGUUU--5'--P | (20mer)<br>(20mer) (SEQ ID NO:13)<br>(SEQ ID NO:12) | 7.2 | 81.7 |
| 308746_357276 | 5'--AAGUAAGGACCAGAGACAAA--3'<br>3'--UUCAUUCCUGGCUCUCUGUUU--5'--P | (20mer)<br>(20mer) (SEQ ID NO:13)<br>(SEQ ID NO:12) | 60.8 | 56.2 |
| 341406_357276 | 5'--AAGUAAGGACCAGAGACAAA--3'<br>3'--UUGCAUUCCUGGCUCUCUGUUU--5'--P | (19mer)<br>(20mer) (SEQ ID NO:19)<br>(SEQ ID NO:12) | 60.8 | 60.8 |
| 357278_357276 | P-5'--AACUAAGGACCAGAGACAA--3'<br>3'--UUGCAUUCCUGGCUCUCUGUUU--5'--P | (19mer)<br>(20mer) (SEQ ID NO:19)<br>(SEQ ID NO:12) | 64.6 | 57 |
| 308746_357275 | 5'--AAGUAAGGACCAGAGACAAA--3'<br>3'--UUCAUUCCUGGCUCUCUGUUU--5'--P | (20mer)<br>(20mer) (SEQ ID NO:13)<br>(SEQ ID NO:12) | 0.15 | 85.0 |

FIG. 1a

1/3 PTEN siRNA CONSTRUCTS bold type indicates 2'-MOE, plain text indicates 2'-OH

| Compound (sense_antisense) | Construct (Sense 5'→3' / Antisense) | | | IC50(nM) | Efficacy (% UTC) |
|---|---|---|---|---|---|
| 348458_357275 | P--5'--AAGUAAGGACCACCAGAAACACAA--3'<br>3'--UUCAUUCCUGGUGGUCUCUGUGUUU--5'--P | (19mer) (20mer) | (SEQ ID NO:19) (SEQ ID NO:12) | 0.15 | 83.0 |
| 359467_357275 | P--5'--AAGUAAGGACCACCAGAAACACAA--3'<br>3'--UUCAUUCCUGGUGGUCUCUGUGUUU--5'--P | (19mer) (20mer) | (SEQ ID NO:19) (SEQ ID NO:12) | 0.1 | 80.0 |
| 355771_357275 | P--5'--AAGUAAGGACCACCAGAAACACAA--3'<br>3'--UUCAUUCCUGGUGGUCUCUGUGUUU--5'--P | (19mer) (20mer) | (SEQ ID NO:19) (SEQ ID NO:12) | 5.5 | 70.0 |
| 357278_357275 | P--5'--AAGUAAGGACCACCAGAAACACAA--3'<br>3'--UUCAUUCCUGGUGGUCUCUGUGUUU--5'--P | (19mer) (20mer) | (SEQ ID NO:19) (SEQ ID NO:12) | 0.9 | 80.0 |
| 341406_357275 | 5'-- AAGUAAGGACCACCAGAAACACAA--3'<br>3'-- UUCAUUCCUGGUGGUCUCUGUGUUU--5' | (20mer) (20mer) | (SEQ ID NO:19) (SEQ ID NO:12) | 2.3 | 70 |
| 308746_357275 | P--5'-- AAGUAAGGACCACCAGAAACACAA--3'<br>3'-- UUCAUUCCUGGUGGUCUCUGUGUUU--5'--P | (20mer) (20mer) | (SEQ ID NO:19) (SEQ ID NO:12) | 20.0 | 60.0 |

FIG. 1b

PTEN siRNA CONSTRUCTS bold type indicates 2'-MOE, plain text indicates 2'-OH

| Compound (sense_antisense) | Construct (Sense 5'→3' / Antisense) | | IC50 (nM) | Efficacy (% UTC) |
|---|---|---|---|---|
| 357278_357276 | P-5'-AAGUAAGGACCAGAGACAA-3' <br> 3'-UUCAUUCCUGGUCGUCUGUUU-5'-p | (19mer) (SEQ ID NO:19) <br> (20mer) (SEQ ID NO:12) | N/A | 40.0 |
| 348458_357276 | P-5'-AAGUAAGGACCAGAGACAA-3' <br> 3'-UUCAUUCCUGGUCGUCUGUUU-5'-p | (19mer) (SEQ ID NO:19) <br> (20mer) (SEQ ID NO:12) | 122 | 61.0 |
| 359467_357276 | 5'-AAGUAAGGACCAGAGACAA-3' <br> 3'-UUCAUUCCUGGUCGUCUGUUU-5'-p | (19mer) (SEQ ID NO:19) <br> (20mer) (SEQ ID NO:12) | 15-150 | 25.0 |
| 348406_357276 | 5'-AAGUAAGGACCAGAGACAA-3' <br> 3'-UUCAUUCCUGGUCGUCUGUUU-5'-p | (19mer) (SEQ ID NO:19) <br> (20mer) (SEQ ID NO:12) | 159 | 51.0 |

FIG. 1c

POSITIONALLY MODIFIED SIRNA CONSTRUCTS

CROSS REFERENCED TO RELATED APPLICATIONS

This application is a U.S. National Phase filing under 35 U.S.C. 371 claiming priority to International Serial No. PCT/US2004/017485 filed Jun. 3, 2004, which is incorporated herein by reference in its entirety.

FIELD OF THE INVENTION

The present invention provides oligomeric compounds having sufficient complementarity to hybridize to a nucleic acid target and methods for their use in modulating gene expression. In one embodiment the oligomeric compounds comprise double stranded constructs wherein one of the strands capable of hybridizing to a nucleic acid target, and has a plurality of modified ribofuranosyl nucleosides at defined locations. The presence of modifications at such defined positions greatly enhances the properties of the corresponding compositions.

BACKGROUND OF THE INVENTION

In many species, introduction of double-stranded RNA (dsRNA) induces potent and specific gene silencing. This phenomenon occurs in both plants and animals and has roles in viral defense and transposon silencing mechanisms. This phenomenon was originally described more than a decade ago by researchers working with the petunia flower. While trying to deepen the purple color of these flowers, Jorgensen et al. introduced a pigment-producing gene under the control of a powerful promoter. Instead of the expected deep purple color, many of the flowers appeared variegated or even white. Jorgensen named the observed phenomenon "cosuppression", since the expression of both the introduced gene and the homologous endogenous gene was suppressed (Napoli et al., *Plant Cell,* 1990, 2, 279-289; Jorgensen et al., *Plant Mol. Biol.,* 1996, 31, 957-973).

Cosuppression has since been found to occur in many species of plants, fungi, and has been particularly well characterized in *Neurospora crassa,* where it is known as "quelling" (Cogoni and Macino, *Genes Dev.* 2000, 10, 638-643; Guru, *Nature,* 2000, 404, 804-808).

The first evidence that dsRNA could lead to gene silencing in animals came from work in the nematode, *Caenorhabditis elegans.* In 1995, researchers Guo and Kemphues were attempting to use antisense RNA to shut down expression of the par-1 gene in order to assess its function. As expected, injection of the antisense RNA disrupted expression of par-1, but quizzically, injection of the sense-strand control also disrupted expression (Guo and Kempheus, *Cell,* 1995, 81, 611-620). This result was a puzzle until Fire et al. injected dsRNA (a mixture of both sense and antisense strands) into *C. elegans.* This injection resulted in much more efficient silencing than injection of either the sense or the antisense strands alone. Injection of just a few molecules of dsRNA per cell was sufficient to completely silence the homologous gene's expression. Furthermore, injection of dsRNA into the gut of the worm caused gene silencing not only throughout the worm, but also in first generation offspring (Fire et al., *Nature,* 1998, 391, 806-811).

The potency of this phenomenon led Timmons and Fire to explore the limits of the dsRNA effects by feeding nematodes bacteria that had been engineered to express dsRNA homologous to the *C. elegans* unc-22 gene. Surprisingly, these worms developed an unc-22 null-like phenotype (Timmons and Fire, *Nature* 1998, 395, 854; Timmons et al., *Gene,* 2001, 263, 103-112). Further work showed that soaking worms in dsRNA was also able to induce silencing (Tabara et al., *Science,* 1998, 282, 430-431). PCT publication WO 01/48183 discloses methods of inhibiting expression of a target gene in a nematode worm involving feeding to the worm a food organism which is capable of producing a double-stranded RNA structure having a nucleotide sequence substantially identical to a portion of the target gene following ingestion of the food organism by the nematode, or by introducing a DNA capable of producing the double-stranded RNA structure (Bogaert et al., 2001).

The posttranscriptional gene silencing defined in *Caenorhabditis elegans* resulting from exposure to double-stranded RNA (dsRNA) has since been designated as RNA interference (RNAi). This term has come to generalize all forms of gene silencing involving dsRNA leading to the sequence-specific reduction of endogenous targeted mRNA levels; unlike co-suppression, in which transgenic DNA leads to silencing of both the transgene and the endogenous gene. Introduction of exogenous double-stranded RNA (dsRNA) into *Caenorhabditis elegans* has been shown to specifically and potently disrupt the activity of genes containing homologous sequences. Montgomery et al., suggest that the primary interference effects of dsRNA are post-transcriptional; this conclusion being derived from examination of the primary DNA sequence after dsRNA-mediated interference a finding of no evidence of alterations followed by studies involving alteration of an upstream operon having no effect on the activity of its downstream gene. These results argue against an effect on initiation or elongation of transcription. Finally they observed by in situ hybridization, that dsRNA-mediated interference produced a substantial, although not complete, reduction in accumulation of nascent transcripts in the nucleus, while cytoplasmic accumulation of transcripts was virtually eliminated. These results indicate that the endogenous mRNA is the primary target for interference and suggest a mechanism that degrades the targeted mRNA before translation can occur. It was also found that this mechanism is not dependent on the SMG system, an mRNA surveillance system in *C. elegans* responsible for targeting and destroying aberrant messages. The authors further suggest a model of how dsRNA might function as a catalytic mechanism to target homologous mRNAs for degradation. (Montgomery et al., *Proc. Natl. Acad. Sci. USA,* 1998, 95, 15502-15507).

Recently, the development of a cell-free system from syncytial blastoderm *Drosophila* embryos that recapitulates many of the features of RNAi has been reported. The interference observed in this reaction is sequence specific, is promoted by dsRNA but not single-stranded RNA, functions by specific mRNA degradation, and requires a minimum length of dsRNA. Furthermore, preincubation of dsRNA potentiates its activity demonstrating that RNAi can be mediated by sequence-specific processes in soluble reactions (Tuschl et al., *Genes Dev.,* 1999, 13, 3191-3197).

In subsequent experiments, Tuschl et al., using the *Drosophila* in vitro system, demonstrated that 21- and 22-nt RNA fragments are the sequence-specific mediators of RNAi. These fragments, which they termed short interfering RNAs (siRNAs) were shown to be generated by an RNase III-like processing reaction from long dsRNA. They also showed that chemically synthesized siRNA duplexes with overhanging 3' ends mediate efficient target RNA cleavage in the *Drosophila* lysate, and that the cleavage site is located near the center of the region spanned by the guiding siRNA. In addition, they suggest that the direction of dsRNA processing determines whether sense or antisense target RNA can be cleaved by the siRNA-protein complex (Elbashir et al., *Genes Dev.*, 2001, 15, 188-200). Further characterization of the suppression of expression of endogenous and heterologous genes caused by the 21-23 nucleotide siRNAs have been investigated in several mammalian cell lines, including human embryonic kidney (293) and HeLa cells (Elbashir et al., *Nature*, 2001, 411, 494-498).

Most recently, Tijsterman et al., have shown that, in fact, single-stranded RNA oligomers of antisense polarity can be potent inducers of gene silencing. As is the case for co-suppression, they showed that antisense RNAs act independently of the RNAi genes rde-1 and rde-4 but require the mutator/RNAi gene mut-7 and a putative DEAD box RNA helicase, mut-14. According to the authors, their data favor the hypothesis that gene silencing is accomplished by RNA primer extension using the mRNA as template, leading to dsRNA that is subsequently degraded suggesting that single-stranded RNA oligomers are ultimately responsible for the RNAi phenomenon (Tijsterman et al., *Science*, 2002, 295, 694-697).

Several recent publications have described the structural requirements for the dsRNA trigger required for RNAi activity. Recent reports have indicated that ideal dsRNA sequences are 21 nt in length containing 2 nt 3'-end overhangs (Elbashir et al, *EMBO*, 2001, 20, 6877-6887, Sabine Brantl, Biochimica et Biophysica Acta, 2002, 1575, 15-25.) In this system, substitution of the 4 nucleosides from the 3'-end with 2'-deoxynucleosides has been demonstrated to not affect activity. On the other hand, substitution with 2'-deoxynucleosides or 2'-OCH$_3$-nucleosides throughout the sequence (sense or antisense) was shown to be deleterious to RNAi activity.

Investigation of the structural requirements for RNA silencing in *C. elegans* has demonstrated modification of the internucleotide linkage (phosphorothioate) to not interfere with activity (Parrish et al., *Molecular Cell*, 2000, 6, 1077-1087). It was also shown by Parrish et al., that chemical modification like 2'-amino or 5'-iodouridine are well tolerated in the sense strand but not the antisense strand of the dsRNA suggesting differing roles for the 2 strands in RNAi. Base modification such as guanine to inosine (where one hydrogen bond is lost) has been demonstrated to decrease RNAi activity independently of the position of the modification (sense or antisense). Same "position independent" loss of activity has been observed following the introduction of mismatches in the dsRNA trigger. Some types of modifications, for example introduction of sterically demanding bases such as 5-iodoU, have been shown to be deleterious to RNAi activity when positioned in the antisense strand, whereas modifications positioned in the sense strand were shown to be less detrimental to RNAi activity. As was the case for the 21 nt dsRNA sequences, RNA-DNA heteroduplexes did not serve as triggers for RNAi. However, dsRNA containing 2'-2'-F modified nucleosides appeared to be efficient in triggering RNAi response independent of the position (sense or antisense) of the 2'-F modified nucleoside.

In one experiment the reduction of gene expression was studied using electroporated dsRNA and a 25mer morpholino in post implantation mouse embryos (Mellitzer et al., *Mechanisms of Development*, 2002, 118, 57-63). The morpholino oligomer did show activity but was not as effective as the dsRNA.

A number of PCT applications have recently been published that relate to the RNAi phenomenon. These include: PCT publication WO 00/44895; PCT publication WO 00/49035; PCT publication WO 00/63364; PCT publication WO 01/36641; PCT publication WO 01/36646; PCT publication WO 99/32619; PCT publication WO 00/44914; PCT publication WO 01/29058; and PCT publication WO 01/75164.

U.S. Pat. Nos. 5,898,031 and 6,107,094, each of which is commonly owned with this application and each of which is herein incorporated by reference, describe certain oligonucleotide having RNA like properties. When hybridized with RNA, these oligonucleotides serve as substrates for a dsRNase enzyme with resultant cleavage of the RNA by the enzyme.

In another recently published paper (Martinez et al., *Cell*, 2002, 110, 563-574) it was shown that double stranded as well as single stranded siRNA resides in the RNA-induced silencing complex (RISC) together with elF2C1 and elf2C2 (human GERp950 Argonaute proteins. The activity of 5'-phosphorylated single stranded siRNA was comparable to the double stranded siRNA in the system studied. In a related study, the inclusion of a 5'-phosphate moiety was shown to enhance activity of siRNA's in vivo in *Drosophilia* embryos (Boutla, et al., Curr. Biol., 2001, 11, 1776-1780). In another study, it was reported that the 5'-phosphate was required for siRNA function in human HeLa cells (Schwarz et al., *Molecular Cell*, 2002, 10, 537-548).

In one recently published paper the authors claim that inclusion of 2'-O-methyl groups into the sense, antisense or both the sense and antisense strands of a siRNA showed greatly reduced activity (Chiu, Ya-Lin and Rana, Tariq, M., *RNA*, 2003, 9, 1034-1048).

Like the RNAse H pathway, the RNA interference pathway of antisense modulation of gene expression is an effective means for modulating the levels of specific gene products and may therefore prove to be uniquely useful in a number of therapeutic, diagnostic, and research applications involving gene silencing. The present invention therefore further provides compositions useful for modulating gene expression pathways, including those relying on an antisense mechanism of action such as RNA interference and dsRNA enzymes as well as non-antisense mechanisms. One having skill in the art, once armed with this disclosure will be able, without undue experimentation, to identify preferred compositions for these uses.

SUMMARY OF THE INVENTION

In some embodiments, the present invention provides compositions comprising a first oligomeric compound and a second oligomeric compound, wherein:

at least a portion of the first oligomeric compound is capable of hybridizing with at least a portion of the second oligomeric compound;

at least a portion of the first oligomeric compound is complementary to and capable of hybridizing to a selected target nucleic acid;

the first and the second oligomeric compounds each comprise a plurality of nucleosides linked by internucleoside linking groups;

the first oligomeric compound comprises a plurality of modified ribofuranosyl nucleosides located at three or more, four or more, five or more, six or more, seven or more, or all of positions 1, 2, 3, 9, 12, 17, 18 and 19 of the first oligomeric compound, counting from the terminal 5'-hybridizing nucleoside of the first oligomeric compound;

wherein each of the first and second oligomeric compounds optionally comprises a phosphate group, a 3' or 5'-overhang or a conjugate group.

In some embodiments, the modified ribofuranosyl nucleosides of the first oligomeric compound are 4'-thio nucleosides. In further embodiments, the modified ribofuranosyl nucleosides of the first oligomeric compound are 2'-Omethyl nucleosides.

In further embodiments, the present invention provides compositions comprising a first oligomeric compound and a second oligomeric compound, wherein:

at least a portion of the first oligomeric compound is capable of hybridizing with at least a portion of the second oligomeric compound;

at least a portion of the first oligomeric compound is complementary to and capable of hybridizing to a selected target nucleic acid;

the first and the second oligomeric compounds each comprise a plurality of nucleosides linked by internucleoside linking groups;

each of the first and second oligomeric compounds optionally comprises a phosphate group, a 3' or 5'-overhang or a conjugate group;

the first oligomeric compound comprises a plurality of modified ribofuranosyl nucleosides located at positions 1-20 of the first oligomeric compound, counting from the terminal 5'-hybridizing nucleoside of the first oligomeric compound; wherein:

a) the nucleosides at positions 1-5, 8, 9 and 12-17 of the first oligomeric compound, counting from the terminal 5'-hybridizing nucleoside of the first oligomeric compound, are 2'-fluoro nucleosides; or b) the nucleosides at positions 6, 7, 10, 11, 18, 19 and 20 of the first oligomeric compound, counting from the terminal 5'-hybridizing nucleoside of the first oligomeric compound, are 2'-Omethyl nucleosides; or c) the nucleosides at positions 1-5, 8, 9 and 12-17 of the first oligomeric compound, counting from the terminal 5'-hybridizing nucleoside of the first oligomeric compound, are 2'-fluoro nucleosides; and the nucleosides at positions 6, 7, 10, 11, 18, 19 and 20 of the first oligomeric compound, counting from the terminal 5'-hybridizing nucleoside of the first oligomeric compound, are 2'-Omethyl nucleosides.

In further embodiments, the present invention provides compositions comprising a first oligomeric compound and a second oligomeric compound, wherein:

at least a portion of the first oligomeric compound is capable of hybridizing with at least a portion of the second oligomeric compound;

at least a portion of the first oligomeric compound is complementary to and capable of hybridizing to a selected target nucleic acid;

the first and the second oligomeric compounds each comprise a plurality of nucleosides linked by internucleoside linking groups;

each of the first and second oligomeric compounds optionally comprises a phosphate group, a 3' or 5'-overhang or a conjugate group;

the first oligomeric compound comprises a plurality of modified ribofuranosyl nucleosides located at three or more, four or more, five or more, six or more, of all of positions 5, 6, 9, 10, 17, 18 and 19 of the first oligomeric compound, counting from the terminal 5'-hybridizing nucleoside of the first oligomeric compound.

In further embodiments, the present invention provides compositions comprising a first oligomeric compound and a second oligomeric compound, wherein:

at least a portion of the first oligomeric compound is capable of hybridizing with at least a portion of the second oligomeric compound;

at least a portion of the first oligomeric compound is complementary to and capable of hybridizing to a selected target nucleic acid;

the first and the second oligomeric compounds each comprise a plurality of nucleosides linked by internucleoside linking groups;

each of the first and second oligomeric compounds optionally comprises a phosphate group, a 3' or 5'-overhang or a conjugate group;

the first oligomeric compound comprises a plurality of modified ribofuranosyl nucleosides located at three or more, four or more, five or more, or all of positions 5, 11, 14, 17, 18 and 19 of the first oligomeric compound, counting from the terminal 5'-hybridizing nucleoside of the first oligomeric compound.

In further embodiments, the present invention provides compositions comprising a first oligomeric compound and a second oligomeric compound, wherein:

at least a portion of the first oligomeric compound is capable of hybridizing with at least a portion of the second oligomeric compound;

at least a portion of the first oligomeric compound is complementary to and capable of hybridizing to a selected target nucleic acid;

the first and the second oligomeric compounds each comprise a plurality of nucleosides linked by internucleoside linking groups;

each of the first and second oligomeric compounds optionally comprises a phosphate group, a 3' or 5'-overhang or a conjugate group; and the first oligomeric compound comprises a plurality of modified ribofuranosyl nucleosides located at three or more, four of more, five or more, six or more, or all of positions 5, 8, 11, 14, 17, 18 and 19 of the first oligomeric compound, counting from the terminal 5'-hybridizing nucleoside of the first oligomeric compound.

In further embodiments, the present invention provides composition comprising a first oligomeric compound and a second oligomeric compound, wherein:

at least a portion of the first oligomeric compound is capable of hybridizing with at least a portion of the second oligomeric compound;

at least a portion of the first oligomeric compound is complementary to and capable of hybridizing to a selected target nucleic acid;

the first and the second oligomeric compounds each comprise a plurality of nucleosides linked by internucleoside linking groups;

each of the first and second oligomeric compounds optionally comprises a phosphate group, a 3' or 5'-overhang or a conjugate group; and the first oligomeric compound comprises a plurality of modified ribofuranosyl nucleosides located at two or more of positions 3, 7, and 15 of the first oligomeric compound, counting from the terminal 5'-hybridizing nucleoside of the first oligomeric compound.

In further embodiments, the present invention provides compositions comprising a first oligomeric compound and a second oligomeric compound, wherein:

at least a portion of the first oligomeric compound is capable of hybridizing with at least a portion of the second oligomeric compound;

at least a portion of the first oligomeric compound is complementary to and capable of hybridizing to a selected target nucleic acid;

the first and the second oligomeric compounds each comprise a plurality of nucleosides linked by internucleoside linking groups;

each of the first and second oligomeric compounds optionally comprises a phosphate group, a 3' or 5'-overhang or a conjugate group; and the first oligomeric compound comprises a plurality of modified ribofuranosyl nucleosides located at two or more of positions 4, 10, and 19 of the first oligomeric compound, counting from the terminal 5'-hybridizing nucleoside of the first oligomeric compound.

In further embodiments, the present invention provides compositions comprising a first oligomeric compound and a second oligomeric compound, wherein:

at least a portion of the first oligomeric compound is capable of hybridizing with at least a portion of the second oligomeric compound;

at least a portion of the first oligomeric compound is complementary to and capable of hybridizing to a selected target nucleic acid;

the first and the second oligomeric compounds each comprise a plurality of nucleosides linked by internucleoside linking groups;

each of the first and second oligomeric compounds optionally comprises a phosphate group, a 3' or 5'-overhang or a conjugate group; and the first oligomeric compound comprises a plurality of modified ribofuranosyl nucleosides located at two or more of positions 4, 8, and 16 of the first oligomeric compound, counting from the terminal 5'-hybridizing nucleoside of the first oligomeric compound.

In further embodiments, the present invention provides composition comprising a first oligomeric compound and a second oligomeric compound, wherein:

at least a portion of the first oligomeric compound is capable of hybridizing with at least a portion of the second oligomeric compound;

at least a portion of the first oligomeric compound is complementary to and capable of hybridizing to a selected target nucleic acid;

the first and the second oligomeric compounds each comprise a plurality of nucleosides linked by internucleoside linking groups;

each of the first and second oligomeric compounds optionally comprises a phosphate group, a 3' or 5'-overhang or a conjugate group; and the first oligomeric compound comprises a plurality of modified ribofuranosyl nucleosides located at two or more of positions 4, 11, and 19 of the first oligomeric compound, counting from the terminal 5'-hybridizing nucleoside of the first oligomeric compound.

In further embodiments, the present invention provides compositions comprising a first oligomeric compound and a second oligomeric compound, wherein:

at least a portion of the first oligomeric compound is capable of hybridizing with at least a portion of the second oligomeric compound;

at least a portion of the first oligomeric compound is complementary to and capable of hybridizing to a selected target nucleic acid;

the first and the second oligomeric compounds each comprise a plurality of nucleosides linked by internucleoside linking groups;

each of the first and second oligomeric compounds optionally comprises a phosphate group, a 3' or 5'-overhang or a conjugate group; and the first oligomeric compound comprises a plurality of modified ribofuranosyl nucleosides located at two or more of positions 3, 10, and 18 of the first oligomeric compound, counting from the terminal 5'-hybridizing nucleoside of the first oligomeric compound.

In further embodiments, the present invention provides compositions comprising a first oligomeric compound and a second oligomeric compound, wherein:

at least a portion of the first oligomeric compound is capable of hybridizing with at least a portion of the second oligomeric compound;

at least a portion of the first oligomeric compound is complementary to and capable of hybridizing to a selected target nucleic acid;

the first and the second oligomeric compounds each comprise a plurality of nucleosides linked by internucleoside linking groups;

each of the first and second oligomeric compounds optionally comprises a phosphate group, a 3' or 5'-overhang or a conjugate group; and the first oligomeric compound comprises a plurality of modified ribofuranosyl nucleosides located at three or more, four or more, five or more, six or more, or all of positions 6, 7, 10, 11, 17, 18 and 19 of the first oligomeric compound, counting from the terminal 5'-hybridizing nucleoside of the first oligomeric compound.

In further embodiments, the present invention provides compositions comprising a first oligomeric compound and a second oligomeric compound, wherein:

at least a portion of the first oligomeric compound is capable of hybridizing with at least a portion of the second oligomeric compound;

at least a portion of the first oligomeric compound is complementary to and capable of hybridizing to a selected target nucleic acid;

the first and the second oligomeric compounds each comprise a plurality of nucleosides linked by internucleoside linking groups;

each of the first and second oligomeric compounds optionally comprises a phosphate group, a 3' or 5'-overhang or a conjugate group; and the first oligomeric compound comprises a plurality of modified ribofuranosyl nucleosides located at two or more of positions 4, 9 and 18 of the first oligomeric compound, counting from the terminal 5'-hybridizing nucleoside of the first oligomeric compound.

In further embodiments, the present invention provides compositions comprising a first oligomeric compound and a second oligomeric compound, wherein:

at least a portion of the first oligomeric compound is capable of hybridizing with at least a portion of the second oligomeric compound;

at least a portion of the first oligomeric compound is complementary to and capable of hybridizing to a selected target nucleic acid;

the first and the second oligomeric compounds each comprise a plurality of nucleosides linked by internucleoside linking groups;

each of the first and second oligomeric compounds optionally comprises a phosphate group, a 3' or 5'-overhang or a conjugate group; and the first oligomeric compound comprises a plurality of modified ribofuranosyl nucleosides located at three or more, four or more, five or more, or all of positions 3, 9, 12, 17, 18 and 19 of the first oligomeric compound, counting from the terminal 5'-hybridizing nucleoside of the first oligomeric compound.

In further embodiments, the present invention provides compositions comprising a first oligomeric compound and a second oligomeric compound, wherein:

at least a portion of the first oligomeric compound is capable of hybridizing with at least a portion of the second oligomeric compound;

at least a portion of the first oligomeric compound is complementary to and capable of hybridizing to a selected target nucleic acid;

the first and the second oligomeric compounds each comprise a plurality of nucleosides linked by internucleoside linking groups;

each of the first and second oligomeric compounds optionally comprises a phosphate group, a 3' or 5'-overhang or a conjugate group; and the first oligomeric compound comprises a plurality of modified ribofuranosyl nucleosides located at three or more, four or more, or all of positions 15, 16, 17, 18 and 19 of the first oligomeric compound, counting from the terminal 5'-hybridizing nucleoside of the first oligomeric compound.

In further embodiments, the present invention provides compositions comprising a first oligomeric compound and a second oligomeric compound, wherein:

at least a portion of the first oligomeric compound is capable of hybridizing with at least a portion of the second oligomeric compound;

at least a portion of the first oligomeric compound is complementary to and capable of hybridizing to a selected target nucleic acid;

the first and the second oligomeric compounds each comprise a plurality of nucleosides linked by internucleoside linking groups;

each of the first and second oligomeric compounds optionally comprises a phosphate group, a 3' or 5'-overhang or a conjugate group; and the first oligomeric compound comprises modified ribofuranosyl nucleosides located at three or more of positions 5, 8, 11 and 14, of the first oligomeric compound, counting from the terminal 5'-hybridizing nucleoside of the first oligomeric compound, and different modified ribofuranosyl nucleosides located at two or more of positions 17, 18 and 19 of the first oligomeric compound, counting from the terminal 5'-hybridizing nucleoside of the first oligomeric compound.

In further embodiments, the present invention provides compositions comprising a first oligomeric compound and a second oligomeric compound, wherein:

at least a portion of the first oligomeric compound is capable of hybridizing with at least a portion of the second oligomeric compound;

at least a portion of the first oligomeric compound is complementary to and capable of hybridizing to a selected target nucleic acid;

the first and the second oligomeric compounds each comprise a plurality of nucleosides linked by internucleoside linking groups;

each of the first and second oligomeric compounds optionally comprises a phosphate group, a 3' or 5'-overhang or a conjugate group; and the first oligomeric compound comprises modified ribofuranosyl nucleosides located at three or more, four or more, or all of positions 1, 2, 3, 9 and 12 of the first oligomeric compound, counting from the terminal 5'-hybridizing nucleoside of the first oligomeric compound, and different modified ribofuranosyl nucleosides located at two or more of positions 17, 18 and 19 of the first oligomeric compound, counting from the terminal 5'-hybridizing nucleoside of the first oligomeric compound.

In some embodiments, the modified ribofuranosyl nucleosides of the first oligomeric compound located at three or more, four or more, or all of positions 1, 2, 3, 9 and 12, of the first oligomeric compound, are 4'-thio nucleosides; and/or the modified ribofuranosyl nucleosides of the first oligomeric compound located at two or more of positions 17, 18 and 19 of the first oligomeric compound, are 2'-Omethyl nucleosides.

In further embodiments, the present invention provides compositions comprising a first oligomeric compound and a second oligomeric compound, wherein:

at least a portion of the first oligomeric compound is capable of hybridizing with at least a portion of the second oligomeric compound;

at least a portion of the first oligomeric compound is complementary to and capable of hybridizing to a selected target nucleic acid;

the first and the second oligomeric compounds each comprise a plurality of nucleosides linked by internucleoside linking groups;

each of the first and second oligomeric compounds optionally comprises a phosphate group, a 3' or 5'-overhang or a conjugate group; and the first oligomeric compound comprises a plurality of modified ribofuranosyl nucleosides located at three or more of positions 6, 12, 15, 18, 19 and 20 of the first oligomeric compound, counting from the terminal 5'-hybridizing nucleoside of the first oligomeric compound.

In further embodiments, the present invention provides compositions comprising a first oligomeric compound and a second oligomeric compound, wherein:

at least a portion of the first oligomeric compound is capable of hybridizing with at least a portion of the second oligomeric compound;

at least a portion of the first oligomeric compound is complementary to and capable of hybridizing to a selected target nucleic acid;

the first and the second oligomeric compounds each comprise a plurality of nucleosides linked by internucleoside linking groups;

each of the first and second oligomeric compounds optionally comprises a phosphate group, a 3' or 5'-overhang or a conjugate group; and the first oligomeric compound comprises a plurality of modified ribofuranosyl nucleosides located at three or more, four or more, five or more, six or more, or all of positions 6, 7, 10, 11, 18, 19 and 20 of the first oligomeric compound, counting from the terminal 5'-hybridizing nucleoside of the first oligomeric compound.

In further embodiments, the present invention provides compositions comprising a first oligomeric compound and a second oligomeric compound, wherein:

at least a portion of the first oligomeric compound is capable of hybridizing with at least a portion of the second oligomeric compound;

at least a portion of the first oligomeric compound is complementary to and capable of hybridizing to a selected target nucleic acid;

the first and the second oligomeric compounds each comprise a plurality of nucleosides linked by internucleoside linking groups;

each of the first and second oligomeric compounds optionally comprises a phosphate group, a 3' or 5'-overhang or a conjugate group; and the first oligomeric compound comprises a plurality of modified ribofuranosyl nucleosides located at positions 6, 7, and 8; or at positions 9, 10 and 11 of the first oligomeric compound, counting from the terminal 5'-hybridizing nucleoside of the first oligomeric compound.

In further embodiments, the present invention provides compositions comprising a first oligomeric compound and a second oligomeric compound, wherein:

at least a portion of the first oligomeric compound is capable of hybridizing with at least a portion of the second oligomeric compound;

at least a portion of the first oligomeric compound is complementary to and capable of hybridizing to a selected target nucleic acid;

the first and the second oligomeric compounds each comprise a plurality of nucleosides linked by internucleoside linking groups;

each of the first and second oligomeric compounds optionally comprises a phosphate group, a 3' or 5'-overhang or a conjugate group; and the first oligomeric compound comprises a plurality of modified ribofuranosyl nucleosides located at two or more of positions 4, 10 and 19 of the first oligomeric compound, counting from the terminal 5'-hybridizing nucleoside of the first oligomeric compound.

In further embodiments, the present invention provides compositions comprising a first oligomeric compound and a second oligomeric compound, wherein:

at least a portion of the first oligomeric compound is capable of hybridizing with at least a portion of the second oligomeric compound;

at least a portion of the first oligomeric compound is complementary to and capable of hybridizing to a selected target nucleic acid;

the first and the second oligomeric compounds each comprise a plurality of nucleosides linked by internucleoside linking groups;

each of the first and second oligomeric compounds optionally comprises a phosphate group, a 3' or 5'-overhang or a conjugate group; and the first oligomeric compound comprises a plurality of modified ribofuranosyl nucleosides located at three or more, four or more, five or more, or all of positions 3, 4, 10, 11, 17 and 18 of the first oligomeric compound, counting from the terminal 5'-hybridizing nucleoside of the first oligomeric compound.

In further embodiments, the present invention provides compositions comprising a first oligomeric compound and a second oligomeric compound, wherein:

at least a portion of the first oligomeric compound is capable of hybridizing with at least a portion of the second oligomeric compound;

at least a portion of the first oligomeric compound is complementary to and capable of hybridizing to a selected target nucleic acid;

the first and the second oligomeric compounds each comprise a plurality of nucleosides linked by internucleoside linking groups;

each of the first and second oligomeric compounds optionally comprises a phosphate group, a 3' or 5'-overhang or a conjugate group; and the first oligomeric compound comprises a plurality of modified ribofuranosyl nucleosides located at six or more, seven or more, eight or more, nine or more, or all of positions 1, 2, 3, 6, 9, 12, 15, 18, 19 and 20 of the first oligomeric compound, counting from the terminal 5'-hybridizing nucleoside of the first oligomeric compound.

In further embodiments, the present invention provides compositions comprising a first oligomeric compound and a second oligomeric compound, wherein:

at least a portion of the first oligomeric compound is capable of hybridizing with at least a portion of the second oligomeric compound;

at least a portion of the first oligomeric compound is complementary to and capable of hybridizing to a selected target nucleic acid;

the first and the second oligomeric compounds each comprise a plurality of nucleosides linked by internucleoside linking groups;

each of the first and second oligomeric compounds optionally comprises a phosphate group, a 3' or 5'-overhang or a conjugate group; and the first oligomeric compound comprises a plurality of modified ribofuranosyl nucleosides located at positions 9, 10, and 11; or at positions 18, 19 and 10 of the first oligomeric compound, counting from the terminal 5'-hybridizing nucleoside of the first oligomeric compound.

In further embodiments, the present invention provides compositions comprising a first oligomeric compound and a second oligomeric compound, wherein:

at least a portion of the first oligomeric compound is capable of hybridizing with at least a portion of the second oligomeric compound;

at least a portion of the first oligomeric compound is complementary to and capable of hybridizing to a selected target nucleic acid;

the first and the second oligomeric compounds each comprise a plurality of nucleosides linked by internucleoside linking groups;

each of the first and second oligomeric compounds optionally comprises a phosphate group, a 3' or 5'-overhang or a conjugate group; and the first oligomeric compound comprises a plurality of modified ribofuranosyl nucleosides located at two or more, three or more, or at all of positions 16, 18, 19 and 20 of the first oligomeric compound, counting from the terminal 5'-hybridizing nucleoside of the first oligomeric compound.

In further embodiments, the present invention provides compositions comprising a first oligomeric compound and a second oligomeric compound, wherein:

at least a portion of the first oligomeric compound is capable of hybridizing with at least a portion of the second oligomeric compound;

at least a portion of the first oligomeric compound is complementary to and capable of hybridizing to a selected target nucleic acid;

the first and the second oligomeric compounds each comprise a plurality of nucleosides linked by internucleoside linking groups;

each of the first and second oligomeric compounds optionally comprises a phosphate group, a 3' or 5'-overhang or a conjugate group; and the first oligomeric compound comprises a plurality of modified ribofuranosyl nucleosides located at positions 1, 2, and 3, or at positions 7, 8 and 9, or at positions 12, 13 and 14, or at positions 13, 14 and 15 of the first oligomeric compound, counting from the terminal 5'-hybridizing nucleoside of the first oligomeric compound.

In further embodiments, the present invention provides compositions comprising a first oligomeric compound and a second oligomeric compound, wherein:

at least a portion of the first oligomeric compound is capable of hybridizing with at least a portion of the second oligomeric compound;

at least a portion of the first oligomeric compound is complementary to and capable of hybridizing to a selected target nucleic acid;

the first and the second oligomeric compounds each comprise a plurality of nucleosides linked by internucleoside linking groups;

each of the first and second oligomeric compounds optionally comprises a phosphate group, a 3' or 5'-overhang or a conjugate group; and the first oligomeric compound comprises a plurality of modified ribofuranosyl nucleosides located at positions 1, 2, and 3; or at positions 3, 4 and 5 of the first oligomeric compound, counting from the terminal 5'-hybridizing nucleoside of the first oligomeric compound.

In further embodiments, the present invention provides compositions comprising a first oligomeric compound and a second oligomeric compound, wherein:

at least a portion of the first oligomeric compound is capable of hybridizing with at least a portion of the second oligomeric compound;

at least a portion of the first oligomeric compound is complementary to and capable of hybridizing to a selected target nucleic acid;

the first and the second oligomeric compounds each comprise a plurality of nucleosides linked by internucleoside linking groups;

each of the first and second oligomeric compounds optionally comprises a phosphate group, a 3' or 5'-overhang or a conjugate group; and the first oligomeric compound comprises a plurality of modified ribofuranosyl nucleosides located at positions 6, 7 and 8, or at positions 9, 10 and 11, or at positions 12, 13 and 14, or at positions 15, 16 and 17, or at positions 18, 19 and 20 of the first oligomeric compound, counting from the terminal 5'-hybridizing nucleoside of the first oligomeric compound.

In some embodiments of each of the foregoing compositions, the first oligomeric compound, the second oligomeric compound, or both can comprises a 5'-overhang, a 3'-overhang, or both. In some such embodiments, the first oligomeric compound comprises a 5'-overhang, that can be, for example, a single nucleoside in length.

In some embodiments of each of the foregoing compositions, the first and the second oligomeric compounds are independently from about 12 to about 30, from about 12 to about 24, from about 19 to about 21, or are each independently 19 or 20 nucleobases in length.

In further embodiments of each of the foregoing compositions, the second oligomeric compound comprises unmodified β-D-ribofuranosyl nucleosides. In further embodiments of each of the foregoing compositions, each of the first and second oligomeric compounds are linked by phosphodiester internucleoside linking groups. In still further embodiments of each of the foregoing compositions, the nucleosides of each of the first and second oligomeric compounds are linked by phosphorothioate internucleoside linking groups.

In further embodiments of each of the foregoing compositions, each of the nucleosides of the first and the second oligomeric compounds are independently linked by phosphorothioate or phosphodiester internucleoside linking groups.

In some embodiments of each of the foregoing compositions, the second oligomeric compound comprises 2'-Omethyl nucleosides. In further embodiments of each of the foregoing compositions, the second oligomeric compound comprises modified ribofuranosyl nucleosides alternating with unmodified β-D-ribofuranosyl nucleosides. In further embodiments of each of the foregoing compositions, the modified ribofuranosyl nucleosides are either 2'-Omethyl nucleosides or 2'-methoxyethoxy nucleosides.

In further embodiments of each of the foregoing compositions, the terminal 5'-hybridizing nucleoside and the terminal 3'-hybridizing nucleoside of the second oligomeric compound are unmodified β-D-ribofuranosyl nucleosides, and the nucleosides in between the terminal hybridizing nucleosides are 2'-Omethyl nucleosides.

In further embodiments of each of the foregoing compositions, the terminal 5'-hybridizing nucleoside of the second oligomeric compound is an unmodified β-D-ribofuranosyl nucleoside and the nucleosides between the terminal 5'-hybridizing nucleoside and the terminal 3'-hybridizing nucleoside including the terminal 3'-hybridizing nucleoside are 2'-Omethyl nucleosides.

In further embodiments of each of the foregoing compositions, the second oligomeric compound comprises one or more modified ribofuranosyl nucleosides independently selected from 2'-fluoro ribofuranosyl sugar moieties, 4'-thio ribofuranosyl moieties, 2'-Omethyl ribofuranosyl sugar moieties, 2'-methoxyethoxy ribofuranosyl moieties, modified ribofuranosyl moieties having a 4'-CH2-O-2'-bridge, and ribofuranosyl moieties having a 4'-(CH2)2-O-2'-bridge.

BRIEF DESCRIPTION OF THE FIGURES

FIGS. 1a, 1b, and 1c show some preferred positional configurations for placement of modified nucleosides in compositions of the invention.

DETAILED DESCRIPTION OF THE INVENTION

In accordance with the present invention there are provided compositions comprising a first oligomeric compound and a second oligomeric compound, wherein at least a portion of the first oligomeric compound is capable of hybridizing with at least a portion of the second oligomeric compound; at least a portion of the first oligomeric compound is complementary to and capable of hybridizing to a selected target nucleic acid; the first and the second oligomeric compounds each comprise a plurality of nucleosides linked by internucleoside linking groups; each of the first and second oligomeric compounds optionally comprises a phosphate group, a 3' or 5'-overhang or a conjugate group; and the first oligomeric compound comprises a plurality of modified ribofuranosyl nucleosides at defined locations. The presence of modifications at such defined positions greatly enhances the properties of the corresponding compositions.

In some embodiments, the positional location of modified ribofuranosyl nucleosides of the first oligomeric compound of the compositions of the invention are described in relation to the terminal 5'-hybridizing nucleoside of the first oligomeric compound. As used herein, the term "terminal 5'-hybridizing nucleoside" is intended to mean the nucleoside closest to the 5'-terminus of the indicated oligomeric compound that is hybridized to a nucleoside of the other oligomeric compound. Thus, for example, in some embodiments, compositions of the invention include a first oligomeric compound and a second oligomeric compound, wherein at least a portion of first oligomeric compound is capable of hybridizing with at least a portion of the second oligomeric compound. In instances where the first and second compounds are of equal length, and are completely complementary, the "terminal 5'-hybridizing nucleoside" of each of the first and second oligomeric compounds would also be the 5'-terminal nucleosides of the respective oligomers. However, in some embodiments, either of the first or second compounds can further comprise additional non-hybridizing nucleosides, for example a 5'-overhang. In such instances, the "terminal 5'-hybridizing nucleoside" is not the terminal nucleotide at the 5'-end of the oligomeric compound (i.e., the 5-terminal nucleoside), but rather is located at a non-terminal. Thus, where a first oligomeric compound of a composition of the invention further comprises a 5'-overhang, the "terminal 5'-hybridizing nucleoside" of the first oligomeric compound is the nucleoside closest to the 5'-end of the first oligomeric compound that hybridizes to a nucleoside of the second oligomeric compound of the composition.

Preferably, the first oligomeric compound contains one or more nucleosides at defined locations (positions) that are modified ribofuranosyl nucleosides that preferably have 3'-endo sugar conformational geometry. Such modified nucleosides include those that have one or more groups in place of one or more hydrogens or hydroxyl groups of naturally occurring nucleosides. Some representative modified ribofuranosyl nucleosides useful in accordance with the present invention include 2'-fluoro ribofuranosyl sugar moieties, 4'-thio ribofuranosyl moieties, 2'-Omethyl ribofuranosyl sugar moieties, 2'-methoxyethoxy ribofuranosyl moieties, modified ribofuranosyl moieties having a 4'-$CH_2$—O-2'-bridge, and ribofuranosyl moieties having a 4'-$(CH_2)_2$—O-2'-bridge. Other representative modified ribofuranosyl nucleosides are described infra.

Compositions of the present invention will be useful for the modulation of gene expression. In one aspect of the present invention a targeted cell, group of cells, a tissue or an animal is contacted with a composition of the invention to effect reduction of message that can directly inhibit gene expression. In another embodiment the reduction of message indirectly upregulates a non-targeted gene through a pathway that relates the targeted gene to a non-targeted gene. Methods and models for the regulation of genes using oligomeric compounds of the invention are illustrated in the examples.

In another aspect a method of inhibiting gene expression is disclosed comprising contacting one or more cells, a tissue or an animal with a composition of the invention. Numerous procedures of how to use the compositions of the present invention are illustrated in the examples section.

Compositions of the invention modulate gene expression by hybridizing to a nucleic acid target resulting in loss of its normal function. As used herein, the term "target nucleic acid" or "nucleic acid target" is used for convenience to encompass any nucleic acid capable of being targeted including without limitation DNA, RNA (including pre-mRNA and mRNA or portions thereof) transcribed from such DNA, and also cDNA derived from such RNA. In a preferred embodiment of the invention the target nucleic acid is a messenger RNA. In a further preferred embodiment the degradation of the targeted messenger RNA is facilitated by a RISC complex that is formed with oligomeric compounds of the invention. In another preferred embodiment the degradation of the targeted messenger RNA is facilitated by a nuclease such as RNaseH.

The hybridization of an oligomeric compound of this invention with its target nucleic acid is generally referred to as "antisense". Consequently, the preferred mechanism in the practice of some preferred embodiments of the invention is referred to herein as "antisense inhibition." Such antisense inhibition is typically based upon hydrogen bonding-based hybridization of oligonucleotide strands or segments such that at least one strand or segment is cleaved, degraded, or otherwise rendered inoperable. In this regard, it is presently preferred to target specific nucleic acid molecules and their functions for such antisense inhibition.

The functions of DNA to be interfered with can include replication and transcription. Replication and transcription, for example, can be from an endogenous cellular template, a vector, a plasmid construct or otherwise. The functions of RNA to be interfered with can include functions such as translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which may be engaged in or facilitated by the RNA. In the context of the present invention, "modulation" and "modulation of expression" mean either an increase (stimulation) or a decrease (inhibition) in the amount or levels of a nucleic acid molecule encoding the gene, e.g., DNA or RNA. Inhibition is often the preferred form of modulation of expression and mRNA is often a preferred target nucleic acid.

The compositions and methods of the present invention are also useful in the study, characterization, validation and modulation of small non-coding RNAs. These include, but are not limited to, microRNAs (miRNA), small nuclear RNAs (snRNA), small nucleolar RNAs (snoRNA), small temporal RNAs (stRNA) and tiny non-coding RNAs (tncRNA) or their precursors or processed transcripts or their association with other cellular components.

Small non-coding RNAs have been shown to function in various developmental and regulatory pathways in a wide range of organisms, including plants, nematodes and mammals. MicroRNAs are small non-coding RNAs that are processed from larger precursors by enzymatic cleavage and inhibit translation of mRNAs. stRNAs, while processed from precursors much like miRNAs, have been shown to be involved in developmental timing regulation. Other non-coding small RNAs are involved in events as diverse as cellular splicing of transcripts, translation, transport, and chromosome organization.

As modulators of small non-coding RNA function, the compositions of the present invention find utility in the control and manipulation of cellular functions or processes such as regulation of splicing, chromosome packaging or methylation, control of developmental timing events, increase or decrease of target RNA expression levels depending on the timing of delivery into the specific biological pathway and translational or transcriptional control. In addition, the compositions of the present invention can be modified in order to optimize their effects in certain cellular compartments, such as the cytoplasm, nucleus, nucleolus or mitochondria.

The compositions of the present invention can further be used to identify components of regulatory pathways of RNA processing or metabolism as well as in screening assays or devices.

Oligomeric Compounds

In the context of the present invention, the term "oligomeric compound" refers to a polymeric structure capable of hybridizing a region of a nucleic acid molecule. This term includes oligonucleotides, oligonucleosides, oligonucleotide analogs, oligonucleotide mimetics and chimeric combinations of these. Oligomeric compounds are routinely prepared linearly but can be joined or otherwise prepared to be circular and may also include branching. Oligomeric compounds can be included double stranded constructs such as for example two strands hybridized to form double stranded compounds. The double stranded oligomeric compounds can be linked or separate and can have blunt ends, overhangs on the ends or can have a combination including a blunt end and an end with an overhang. Further modifications can include conjugate groups attached to one of the termini, selected nucleobase positions, sugar positions or to one of the internucleoside linkages. In general an oligomeric compound comprises a backbone of momeric subunits joined linking groups where each linked momeric subunit is directly or indirectly attached to a heterocyclic base moiety. Oligomeric compounds may also include monomeric subunits that are not linked to a heterocyclic base moiety thereby providing abasic sites. Any one of the repeated units making up an oligomeric compound can be modified giving rise to a variety of motifs including hemimers, gapmers and chimeras.

As is known in the art, a nucleoside comprises a sugar moiety attached to a heterocyclic base moiety. The two most common classes of such heterocyclic bases are purines and pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar giving the more common 3',5-internucleoside linkage or the not so common 2',5'-internucleoside linkage. In forming oligonucleotides, the phosphate groups covalently link the sugar moieties of adjacent nucleosides. The respective ends can be joined to form a circular structure by hybridization or by formation of a covalent bond, however, open linear structures are generally preferred.

In the context of this invention, the term "oligonucleotide" refers to an oligomer or polymer of ribonucleic acid (RNA) or deoxyribonucleic acid (DNA). This term includes oligonucleotides composed of naturally-occurring nucleobases, sugars and covalent internucleoside linkages. The term "oligonucleotide analog" refers to oligonucleotides that have one or more non-naturally occurring portions which function in a similar manner to oligonucleotides. Such oligonucleotide analogs are often preferred over the naturally occurring forms because of desirable properties such as, for example, enhanced cellular uptake, enhanced affinity for a nucleic acid target and enhanced nuclease stability.

In the context of this invention, the term "oligonucleoside" refers to a sequence of nucleosides that are joined by internucleoside linkages that do not have phosphorus atoms. Internucleoside linkages of this type include short chain alkyl, cycloalkyl, mixed heteroatom alkyl, mixed heteroatom cycloalkyl, one or more short chain heteroatomic and one or more short chain heterocyclic. These internucleoside linkages include but are not limited to siloxane, sulfide, sulfoxide, sulfone, acetyl, formacetyl, thioformacetyl, methylene formacetyl, thioformacetyl, alkeneyl, sulfamate; methyleneimino, methylenehydrazino, sulfonate, sulfonamide, amide and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, each of which is herein incorporated by reference.

Further included in the present invention are oligomeric compounds such as antisense oligomeric compounds, antisense oligonucleotides, ribozymes, external guide sequence (EGS) oligonucleotides, alternate splicers, primers, probes, and other oligomeric compounds which hybridize to at least a portion of the target nucleic acid. As such, these oligomeric compounds may be introduced in the form of single-stranded, double-stranded, circular or hairpin oligomeric compounds and may contain structural elements such as internal or terminal bulges or loops. Once introduced to a system, the oligomeric compounds of the invention may elicit the action of one or more enzymes or structural proteins to effect modification of the target nucleic acid.

One non-limiting example of such an enzyme is RNAse H, a cellular endonuclease which cleaves the RNA strand of an RNA:DNA duplex or the RNA region of a duplex that has an RNA:DNA region and may have other chemistries to enhance desired properties. It is known in the art that single-stranded antisense oligomeric compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While the preferred form of antisense oligomeric compound is a single-stranded antisense oligonucleotide, in many species the introduction of double-stranded constructs, such as double-stranded RNA (dsRNA) duplexes, has been shown to induce potent and specific antisense-mediated reduction of the function of a gene or its associated gene products. This phenomenon occurs in both plants and animals and is believed to have an evolutionary connection to viral defense and transposon silencing.

The oligomeric compounds in accordance with this invention preferably comprise from about 8 to about 80 nucleobases (i.e. from about 8 to about 80 linked nucleosides/monomeric subunits). One of ordinary skill in the art will appreciate that the invention embodies oligomeric compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases in length.

In one preferred embodiment, the oligomeric compounds of the invention are 10 to 50 nucleobases in length. One having ordinary skill in the art will appreciate that this embodies oligomeric compounds of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases in length.

In another preferred embodiment, the oligomeric compounds of the invention are 12 to 30 nucleobases in length. One having ordinary skill in the art will appreciate that this embodies oligomeric compounds of 12, 13, 14, 15, 16, 17, 18, 19, 20, 21, 22, 23, 24, 25, 26, 27, 28, 29, or 30 nucleobases in length.

In a further preferred embodiment, the oligomeric compounds of the invention are 12 to 24 nucleobases in length. One having ordinary skill in the art will appreciate that this embodies oligomeric compounds of 12, 13, 14, 15, 16, 17, 18, 19, 20, 21, 22, 23 or 24 nucleobases in length.

In a further preferred embodiment, the oligomeric compounds of the invention are 19 to 23 nucleobases in length. One having ordinary skill in the art will appreciate that this embodies oligomeric compounds of 19, 20, 21, 22 or 23 nucleobases in length.

One particularly preferred length for oligomeric compounds is from about 12 to about 30 nucleobases. Another particularly preferred length is from about 12 to about 24 nucleobases. A further particularly preferred length is from about 19 to about 23 nucleobases.

Chimeric Oligomeric Compounds

It is not necessary for all positions in a oligomeric compound to be uniformly modified, and in fact more than one of the aforementioned modifications may be incorporated in a single oligomeric compound or even at a single monomeric subunit such as a nucleoside within a oligomeric compound. The present invention also includes oligomeric compounds which are chimeric oligomeric compounds. "Chimeric" oligomeric compounds or "chimeras," in the context of this invention, are oligomeric compounds containing two or more chemically distinct regions, each made up of at least one monomer unit, i.e., a nucleotide in the case of a nucleic acid based oligomer.

Chimeric oligomeric compounds typically contain at least one region modified so as to confer increased resistance to nuclease degradation, increased cellular uptake, and/or increased binding affinity for the target nucleic acid. An additional region of the oligomeric compound may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of inhibition of gene expression. Consequently, comparable results can often be obtained with shorter oligomeric compounds when chimeras are used, compared to for example phosphorothioate deoxyoligonucleotides hybridizing to the same target region. Cleavage of the RNA target can be routinely detected by gel electrophoresis and, if necessary, associated nucleic acid hybridization techniques known in the art.

Chimeric oligomeric compounds of the invention may be formed as composite structures of two or more oligonucleotides, oligonucleotide analogs, oligonucleosides and/or oligonucleotide mimetics as described above. Routinely used chimeric compounds include but are not limited to hybrid, hemimers, gapmers, inverted gapmers and blockmers wherein the various point modifications and or regions are selected from native or modified DNA and RNA type units and or mimetic type subunits such as for example LNA, ENA, PNA, morpholinos, and others. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference in its entirety.

Oligomer Mimetics

Another preferred group of oligomeric compounds amenable to the present invention includes oligonucleotide mimetics. The term mimetic as it is applied to oligonucleotides is intended to include oligomeric compounds wherein the furanose ring or the furanose ring and the internucleotide linkage are replaced with novel groups, replacement of only the furanose ring is also referred to in the art as being a sugar surrogate. The heterocyclic base moiety or a modified heterocyclic base moiety is maintained for hybridization with an appropriate target nucleic acid.

One such oligomeric compound, an oligonucleotide mimetic that has been shown to have excellent hybridization properties, is referred to as a peptide nucleic acid (PNA). PNA's have favorable hybridization properties, high biological stability and are electrostatically neutral molecules. In one recent study PNA's were used to correct aberrant splicing in a transgenic mouse model (Sazani et al., *Nat. Biotechnol.*, 2002, 20, 1228-1233). In PNA oligomeric compounds, the sugar-backbone of an oligonucleotide is replaced with an amide containing backbone, in particular an aminoethylglycine backbone. The nucleobases are bound directly or indirectly (—C(=O)—CH$_2$— as shown below) to aza nitrogen atoms of the amide portion of the backbone. Representative United States patents that teach the preparation of PNA oligomeric compounds include, but are not limited to, U.S. Pat. Nos. 5,539,082; 5,714,331; and 5,719,262, each of which is herein incorporated by reference. PNA's can be obtained commercially from Applied Biosystems (Foster City, Calif., USA).

Numerous modifications have been made to the basic PNA backbone since it was introduced in 1991 by Nielsen and coworkers (Nielsen et al., *Science*, 1991, 254, 1497-1500). The basic structure is shown below:

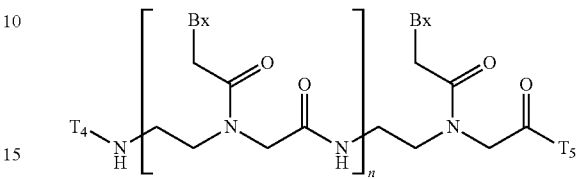

wherein

Bx is a heterocyclic base moiety;

$T_4$ is hydrogen, an amino protecting group, —C(O)R$_5$, substituted or unsubstituted C$_1$-C$_{10}$ alkyl, substituted or unsubstituted C$_2$-C$_{10}$ alkenyl, substituted or unsubstituted C$_2$-C$_{10}$ alkynyl, alkylsulfonyl, arylsulfonyl, a chemical functional group, a reporter group, a conjugate group, a D or L α-amino acid linked via the α-carboxyl group or optionally through the ω-carboxyl group when the amino acid is aspartic acid or glutamic acid or a peptide derived from D, L or mixed D and L amino acids linked through a carboxyl group, wherein the substituent groups are selected from hydroxyl, amino, alkoxy, carboxy, benzyl, phenyl, nitro, thiol, thioalkoxy, halogen, alkyl, aryl, alkenyl and alkynyl;

$T_5$ is —OH, —N(Z$_1$)Z$_2$, R$_5$, D or L α-amino acid linked via the α-amino group or optionally through the ω-amino group when the amino acid is lysine or ornithine or a peptide derived from D, L or mixed D and L amino acids linked through an amino group, a chemical functional group, a reporter group or a conjugate group;

$Z_1$ is hydrogen, C$_1$-C$_6$ alkyl, or an amino protecting group;

$Z_2$ is hydrogen, C$_1$-C$_6$ alkyl, an amino protecting group, —C(=O)—(CH$_2$)$_n$-J-Z$_3$, a D or L α-amino acid linked via the α-carboxyl group or optionally through the ω-carboxyl group when the amino acid is aspartic acid or glutamic acid or a peptide derived from D, L or mixed D and L amino acids linked through a carboxyl group;

$Z_3$ is hydrogen, an amino protecting group, —C$_1$-C$_6$ alkyl, —C(=O)—CH$_3$, benzyl, benzoyl, or —(CH$_2$)$_n$—N(H)Z$_1$;

each J is O, S or NH;

R$_5$ is a carbonyl protecting group; and n is from 2 to about 50.

Another class of oligonucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. A preferred class of linking groups have been selected to give a non-ionic oligomeric compound. The non-ionic morpholino-based oligomeric compounds are less likely to have undesired interactions with cellular proteins. Morpholino-based oligomeric compounds are non-ionic mimics of oligonucleotides which are less likely to form undesired interactions with cellular proteins (Dwaine A. Braasch and David R. Corey, *Biochemistry*, 2002, 41 (14), 4503-4510). Morpholino-based oligomeric compounds have been studied in zebrafish embryos (see: *Genesis*, volume 30, issue 3, 2001 and Heasman, J., *Dev. Biol.*, 2002, 243, 209-214). Further studies of Morpholino-based oligomeric compounds have also been reported (see: Nasevicius et al., *Nat. Genet.*, 2000, 26, 216-220; and Lacerra et al., *Proc. Natl. Acad. Sci.*, 2000, 97, 9591-9596). Morpholino-based oligomeric compounds are disclosed in U.S. Pat. No. 5,034,506. The morpholino class of oligomeric compounds have been prepared having a variety of different linking groups joining the monomeric subunits.

Morpholino nucleic acids have been prepared having a variety of different linking groups ($L_2$) joining the monomeric subunits. The basic formula is shown below:

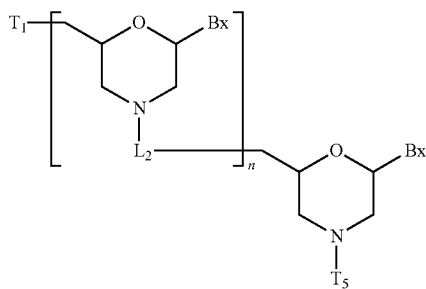

wherein $T_1$ is hydrogen, hydroxyl, a protected hydroxyl, a linked nucleoside or a linked oligomeric compound;

$T_5$ is hydrogen or a phosphate, phosphate derivative, a linked nucleoside or a linked oligomeric compound; and $L_2$ is a linking group which can be varied from chiral to achiral from charged to neutral (U.S. Pat. No. 5,166,315 discloses linkages including —O—P(=O)[N(CH$_3$)$_2$]—O—; U.S. Pat. No. 5,034,506 discloses achiral intermorpholino linkages such as for example: —S(=O)—X— where X is NH, NCH$_3$, O, S, or CH$_2$; —C(=Y)—O— where Y is O or S; —S(=O)(OH)—CH$_2$—; —S(=O)(OH)—N(R)—CH$_2$— where R is H or CH$_3$; and U.S. Pat. No. 5,185,444 discloses phosphorus containing chiral intermorpholino linkages such as for example: —P(=O)(—X)—O— where X is F, CH$_2$R, S—CH$_2$R or NR$_1$R$_2$ and each R, R$_1$ and R$_2$ is H, CH$_3$ or some other moiety that doesn't interfere with the base specific hydrogen bonding; and n is from 2 to about 50.

A further class of oligonucleotide mimetic is referred to as cyclohexenyl nucleic acids (CeNA). The furanose ring normally present in an DNA/RNA molecule is replaced with a cyclohenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., *J. Am. Chem. Soc.*, 2000, 122, 8595-8602). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation. Furthermore the incorporation of CeNA into a sequence targeting RNA was stable to serum and able to activate *E. coli* RNase resulting in cleavage of the target RNA strand.

The general formula of CeNA is shown below:

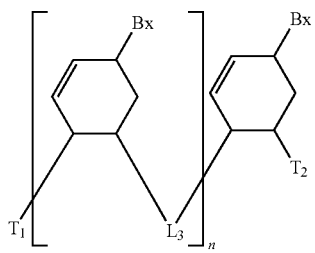

wherein each Bx is a heterocyclic base moiety;

$L_3$ is an inter cyclohexenyl linkage such as for example a phosphodiester or a phosphorothioate linkage;

$T_1$ is hydrogen, hydroxyl, a protected hydroxyl, a linked nucleoside or a linked oligomeric compound; and $T_2$ is hydrogen or a phosphate, phosphate derivative, a linked nucleoside or a linked oligomeric compound.

Another class of oligonucleotide mimetic (anhydrohexitol nucleic acid) can be prepared from one or more anhydrohexitol nucleosides (see, Wouters and Herdewijn, *Bioorg. Med. Chem. Lett.*, 1999, 9, 1563-1566) and would have the general formula:

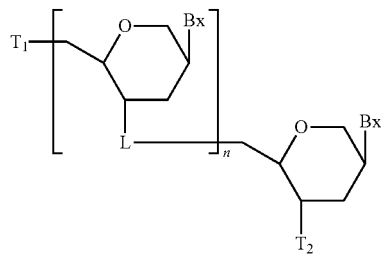

each Bx is a heterocyclic base moiety;

L is an inter anhydrohexitol linkage such as for example a phosphodiester or a phosphorothioate linkage;

$T_1$ is hydrogen, hydroxyl, a protected hydroxyl, a linked nucleoside or a linked oligomeric compound; and $T_2$ is hydrogen or a phosphate, phosphate derivative, a linked nucleoside or a linked oligomeric compound.

A further preferred modification includes bicyclic sugar moieties such as "Locked Nucleic Acids" (LNAs) in which the 2'-hydroxyl group of the ribosyl sugar ring is linked to the 4' carbon atom of the sugar ring thereby forming a 2'-C,4'-C-oxymethylene linkage to form the bicyclic sugar moiety (reviewed in Elayadi et al., *Curr. Opinion Invens. Drugs*, 2001, 2, 558-561; Braasch et al., *Chem. Biol.*, 2001, 8 1-7; and Orum et al., *Curr. Opinion Mol. Ther.*, 2001, 3, 239-243; see also U.S. Pat. Nos. 6,268,490 and 6,670,461). The linkage is preferably a methylene (—CH$_2$—)$_n$ group bridging the 2' oxygen atom and the 4' carbon atom for n=1 the term LNA (locked nucleic acid used here for 2'-O,4'-methylene-bridged nucleic acid) is used for n=2 the term ENA™ (2'-O,4'-ethylene-bridged nucleic acid) is used (Singh et al., Chem. Commun., 1998, 4, 455-456; ENA: Morita et al., *Bioorganic Medicinal Chemistry*, 2003, 11, 2211-2226). LNA and other bicyclic sugar analogs display very high duplex thermal stabilities with complementary DNA and RNA (Tm=+3 to +10 C), stability towards 3'-exonucleolytic degradation and good solubility properties. LNA's are commercially available from ProLigo (Paris, France and Boulder, Colo., USA). The basic structure of LNA showing the bicyclic ring system is shown below:

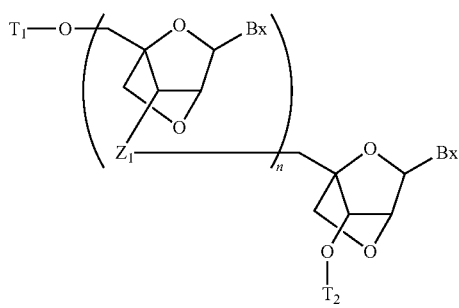

wherein each $T_1$ and $T_2$ is, independently, hydrogen, a hydroxyl protecting group, a linked nucleoside or a linked oligomeric compound, and each $Z_1$ is an internucleoside linking group such as for example phosphodiester or phosphorothioate.

An isomer of LNA that has also been studied is ∀-L-LNA which has been shown to have superior stability against a 3'-exonuclease (Frieden et al., Nucleic Acids Research, 2003, 21, 6365-6372). The ∀-L-LNA's were incorporated into antisense gapmers and chimeras that showed potent antisense activity. The structure of ∀-L-LNA is shown below:

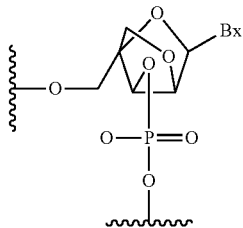

Another similar bicyclic sugar moiety that has been prepared and studied has the bridge going from the 3'-hydroxyl group via a single methylene group to the 4' carbon atom of the sugar ring thereby forming a 3'-C,4'-C-oxymethylene linkage (see U.S. Pat. No. 6,043,060).

The conformations of LNAs determined by 2D NMR spectroscopy have shown that the locked orientation of the LNA nucleotides, both in single-stranded LNA and in duplexes, constrains the phosphate backbone in such a way as to introduce a higher population of the N-type conformation (Petersen et al., J. Mol. Recognit., 2000, 13, 44-53). These conformations are associated with improved stacking of the nucleobases (Wengel et al., Nucleosides Nucleotides, 1999, 18, 1365-1370).

LNA has been shown to form exceedingly stable LNA:LNA duplexes (Koshkin et al., J. Am. Chem. Soc., 1998, 120, 13252-13253). LNA:LNA hybridization was shown to be the most thermally stable nucleic acid type duplex system, and the RNA-mimicking character of LNA was established at the duplex level. Introduction of 3 LNA monomers (T or A) significantly increased melting points (Tm=+15/+11) toward DNA complements. The universality of LNA-mediated hybridization has been stressed by the formation of exceedingly stable LNA:LNA duplexes. The RNA-mimicking of LNA was reflected with regard to the N-type conformational restriction of the monomers and to the secondary structure of the LNA:RNA duplex.

LNAs also form duplexes with complementary DNA, RNA or LNA with high thermal affinities. Circular dichroism (CD) spectra show that duplexes involving fully modified LNA (esp. LNA:RNA) structurally resemble an A-form RNA:RNA duplex. Nuclear magnetic resonance (NMR) examination of an LNA:DNA duplex confirmed the 3'-endo conformation of an LNA monomer. Recognition of double-stranded DNA has also been demonstrated suggesting strand invasion by LNA. Studies of mismatched sequences show that LNAs obey the Watson-Crick base pairing rules with generally improved selectivity compared to the corresponding unmodified reference strands. DNA•LNA chimeras have been shown to efficiently inhibit gene expression when targeted to a variety of regions (5'-untranslated region, region of the start codon or coding region) within the luciferase mRNA (Braasch et al., Nucleic Acids Research, 2002, 30, 5160-5167).

Novel types of LNA-oligomeric compounds, as well as the LNAs, are useful in a wide range of diagnostic and therapeutic applications. Among these are antisense applications, PCR applications, strand-displacement oligomers, substrates for nucleic acid polymerases and generally as nucleotide based drugs.

Potent and nontoxic antisense oligonucleotides containing LNAs have been described (Wahlestedt et al., Proc. Natl. Acad. Sci. U.S.A., 2000, 97, 5633-5638). The authors have demonstrated that LNAs confer several desired properties to antisense compounds. LNA/DNA copolymers were not degraded readily in blood serum and cell extracts. LNA/DNA copolymers exhibited potent antisense activity in assay systems as disparate as G-protein-coupled receptor signaling in living rat brain and detection of reporter genes in Escherichia coli. Lipofectin-mediated efficient delivery of LNA into living human breast cancer cells has also been accomplished. Further successful in vivo studies involving LNA's have shown knock-down of the rat delta opioid receptor without toxicity (Wahlestedt et al., Proc. Natl. Acad. Sci., 2000, 97, 5633-5638) and in another study showed a blockage of the translation of the large subunit of RNA polymerase II (Fluiter et al., Nucleic Acids Res., 2003, 31, 953-962).

The synthesis and preparation of the LNA monomers adenine, cytosine, guanine, 5-methyl-cytosine, thymine and uracil, along with their oligomerization, and nucleic acid recognition properties have been described (Koshkin et al., Tetrahedron, 1998, 54, 3607-3630). LNAs and preparation thereof are also described in WO 98/39352 and WO 99/14226.

The first analogs of LNA, phosphorothioate-LNA and 2'-thio-LNAs, have also been prepared (Kumar et al., Bioorg. Med. Chem. Lett., 1998, 8, 2219-2222). Preparation of locked nucleoside analogs containing oligodeoxyribonucleotide duplexes as substrates for nucleic acid polymerases has also been described (Wengel et al., PCT International Application WO 98-DK393 19980914). Furthermore, synthesis of 2'-amino-LNA, a novel conformationally restricted high-affinity oligonucleotide analog with a handle has been described in the art (Singh et al., J. Org. Chem., 1998, 63, 10035-10039). In addition, 2'-Amino- and 2'-methylamino-LNA's have been prepared and the thermal stability of their duplexes with complementary RNA and DNA strands has been previously reported.

Another oligonucleotide mimetic amenable to the present invention that has been prepared and studied is threose nucleic acid. This oligonucleotide mimetic is based on threose nucleosides instead of ribose nucleosides and has the general structure shown below:

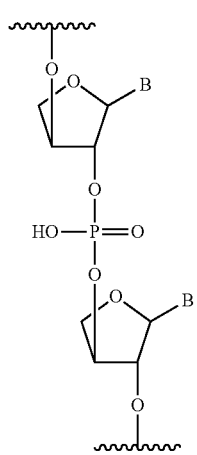

Initial interest in (3',2')-∀-L-threose nucleic acid (TNA) was directed to the question of whether a DNA polymerase existed that would copy the TNA. It was found that certain DNA polymerases are able to copy limited stretches of a TNA template (reported in C&EN/Jan. 13, 2003).

In another study it was determined that TNA is capable of antiparallel Watson-Crick base pairing with complementary DNA, RNA and TNA oligonucleotides (Chaput et al., *J. Am. Chem. Soc.,* 2003, 125, 856-857).

In one study (3',2')-∀-L-threose nucleic acid was prepared and compared to the 2' and 3' amidate analogs (Wu et al., *Organic Letters,* 2002, 4 (8), 1279-1282). The amidate analogs were shown to bind to RNA and DNA with comparable strength to that of RNA/DNA.

Further oligonucleotide mimetics have been prepared to include bicyclic and tricyclic nucleoside analogs having the formulas (amidite monomers shown):

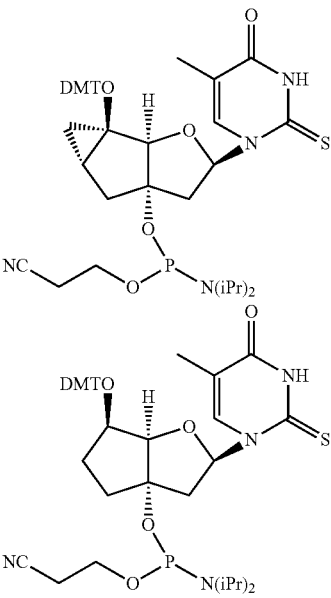

(see Steffens et al., *Helv. Chim. Acta,* 1997, 80, 2426-2439; Steffens et al., *J. Am. Chem. Soc.,* 1999, 121, 3249-3255; Renneberg et al., *J. Am. Chem. Soc.,* 2002, 124, 5993-6002; and Renneberg et al., *Nucleic acids res.,* 2002, 30, 2751-2757). These modified nucleoside analogs have been oligomerized using the phosphoramidite approach and the resulting oligomeric compounds containing tricyclic nucleoside analogs have shown increased thermal stabilities (Tm's) when hybridized to DNA, RNA and itself. Oligomeric compounds containing bicyclic nucleoside analogs have shown thermal stabilities approaching that of DNA duplexes.

Another class of oligonucleotide mimetic is referred to as phosphonomonoester nucleic acids which incorporate a phosphorus group in the backbone. This class of olignucleotide mimetic is reported to have useful physical and biological and pharmacological properties in the areas of inhibiting gene expression (antisense oligonucleotides, ribozymes, sense oligonucleotides and triplex-forming oligonucleotides), as probes for the detection of nucleic acids and as auxiliaries for use in molecular biology.

The general formula (for definitions of Markush variables see: U.S. Pat. Nos. 5,874,553 and 6,127,346 herein incorporated by reference in their entirety) is shown below.

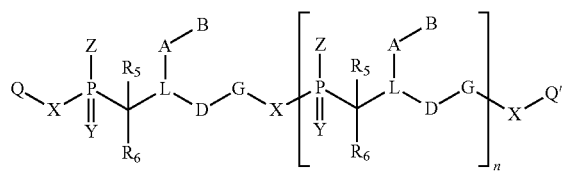

Further oligonucleotide mimetics amenable to the present invention have been prepared wherein a cyclobutyl ring replaces the naturally occurring furanosyl ring.

Oligomer and Monomer Modifications

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are generally preferred. In addition, linear compounds may have internal nucleobase complementarity and may therefore fold in a manner as to produce a fully or partially double-stranded compound. Within oligonucleotides, the phosphate groups are commonly referred to as forming the internucleoside linkage or in conjunction with the sugar ring the backbone of the oligonucleotide. The normal internucleoside linkage that makes up the backbone of RNA and DNA is a 3' to 5' phosphodiester linkage.

Modified Internucleoside Linkages

Specific examples of preferred antisense oligomeric compounds useful in this invention include oligonucleotides containing modified e.g. non-naturally occurring internucleoside linkages. As defined in this specification, oligonucleotides having modified internucleoside linkages include internucleoside linkages that retain a phosphorus atom and internucleoside linkages that do not have a phosphorus atom. For the purposes of this specification, and as sometimes referenced in the art, modified oligonucleotides that do not have a phosphorus atom in their internucleoside backbone can also be considered to be oligonucleosides.

In the *C. elegans* system, modification of the internucleotide linkage (phosphorothioate) did not significantly interfere with RNAi activity. Based on this observation, it is suggested that certain preferred oligomeric compounds of the invention can also have one or more modified internucleoside linkages. A preferred phosphorus containing modified internucleoside linkage is the phosphorothioate internucleoside linkage.

Preferred modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-allylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, phosphonoacetate and thiophosphonoacetate (see Sheehan et al., *Nucleic Acids Research*, 2003, 31 (14), 4109-4118 and Dellinger et al., *J. Am. Chem. Soc.*, 2003, 125, 940-950), selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

N3'-P5'-phosphoramidates have been reported to exhibit both a high affinity towards a complementary RNA strand and nuclease resistance (Gryaznov et al., *J. Am. Chem. Soc.*, 1994, 116, 3143-3144). N3'-P5'-phosphoramidates have been studied with some success in vivo to specifically down regulate the expression of the c-myc gene (Skorski et al., *Proc. Natl. Acad. Sci.*, 1997, 94, 3966-3971; and Faira et al., *Nat. Biotechnol.*, 2001, 19, 40-44).

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, each of which is herein incorporated by reference.

In more preferred embodiments of the invention, oligomeric compounds have one or more phosphorothioate and/or heteroatom internucleoside linkages, in particular —$CH_2$—NH—O—$CH_2$—, —$CH_2$—N($CH_3$)—O—$CH_2$—[known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester internucleotide linkage is represented as —O—P(=O)(OH)—O—$CH_2$—]. The MMI type internucleoside linkages are disclosed in the above referenced U.S. Pat. No. 5,489,677. Preferred amide internucleoside linkages are disclosed in the above referenced U.S. Pat. No. 5,602,240.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, each of which is herein incorporated by reference.

Modified Sugars

Oligomeric compounds of the invention may also contain one or more substituted or other wise modified sugar moieties. Ribosyl and related sugar moieties are routinely modified at any reactive position not involved in linking. Thus a preferred position for a sugar substituent group is the 2'-position not usually used in the native 3' to 5'-internucleoside linkage. Other preferred positions are the 3' and the 5'-termini. 3'-sugar positions are open to modification when the linkage between two adjacent sugar units is a 2',5'-linkage. Preferred sugar substituent groups include: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_3$, O($CH_2$)$_n$$NH_2$, O($CH_2$)$_n$$CH_3$, O($CH_2$)$_n$ON$H_2$, and O($CH_2$)$_n$ON[($CH_2$)$_n$$CH_3$]$_2$, where n and m are from 1 to about 10. Other preferred oligonucleotides comprise a sugar substituent group selected from: $C_1$ to $C_{10}$ lower alkyl, substituted lower alkyl, alkenyl, alkynyl, alkaryl, aralkyl, O-alkaryl or O-aralkyl, SH, S$CH_3$, OCN, Cl, Br, CN, $CF_3$, O$CF_3$, SO$CH_3$, SO$_2$$CH_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties.

A preferred modification includes 2'-methoxyethoxy (2'-O—$CH_2$$CH_2$O$CH_3$, also known as 2'-O-(2-methoxyethyl) or 2'-MOE) (Martin et al., *Helv. Chim. Acta*, 1995, 78, 486-504) i.e., an alkoxyalkoxy group. Further preferred modifications includes 2'-dimethylaminooxyethoxy, i.e., a O($CH_2$)$_2$ON ($CH_3$)$_2$ group, also known as 2'-DMAOE, as described in examples hereinbelow, 2'-dimethylaminoethoxyethoxy (also known in the art as 2'-O-dimethyl-amino-ethoxy-ethyl or 2'-DMAEOE), i.e., 2'-O—($CH_2$)$_2$O—($CH_2$)$_2$N($CH_3$)$_2$, and N-methylacetamide (also referred to as NMA, 2'-O—$CH_2$—C(=O)—N(H)$CH_3$).

Other preferred sugar substituent groups include methoxy (—O—$CH_3$), aminopropoxy (—O$CH_2$$CH_2$$CH_2$$NH_2$), allyl (—$CH_2$—CH=$CH_2$), —O-allyl (—O—$CH_2$—CH=$CH_2$) and fluoro (F). 2'-Sugar substituent groups may be in the arabino (up) position or ribo (down) position. A preferred 2'-arabino modification is 2'-F (see: Loc et al., *Biochemistry*, 2002, 41, 3457-3467). Similar modifications may also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; 5,700,920; and 6,147,200, each of which is herein incorporated by reference in its entirety.

Further representative sugar substituent groups include groups of formula $I_a$ or $II_a$:

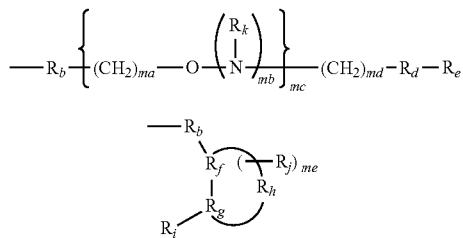

wherein:
$R_b$ is O, S or NH;
$R_d$ is a single bond, O, S or C(=O);
$R_e$ is $C_1$-$C_{10}$ alkyl, $N(R_k)(R_m)$, $N(R_k)(R_n)$, $N=C(R_p)(R_q)$, $N=C(R_p)(R_r)$ or has formula $III_a$;

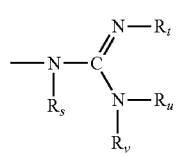

$R_p$ and $R_q$ are each independently hydrogen or $C_1$-$C_{10}$ alkyl;
$R_r$ is —$R_x$-$R_y$;
each $R_s$, $R_t$, $R_u$ and $R_v$ is, independently, hydrogen, C(O)$R_w$, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, alkylsulfonyl, arylsulfonyl, a chemical functional group or a conjugate group, wherein the substituent groups are selected from hydroxyl, amino, alkoxy, carboxy, benzyl, phenyl, nitro, thiol, thioalkoxy, halogen, alkyl, aryl, alkenyl and alkynyl;
or optionally, $R_u$ and $R_v$, together form a phthalimido moiety with the nitrogen atom to which they are attached;
each $R_w$ is, independently, substituted or unsubstituted $C_1$-$C_{10}$ alkyl, trifluoromethyl, cyanoethyloxy, methoxy, ethoxy, t-butoxy, allyloxy, 9-fluorenylmethoxy, 2-(trimethylsilyl)-ethoxy, 2,2,2-trichloroethoxy, benzyloxy, butyryl, isobutyryl, phenyl or aryl;
$R_k$ is hydrogen, a nitrogen protecting group or —$R_x$-$R_y$;
$R_x$ is a bond or a linking moiety;
$R_y$ is a chemical functional group, a conjugate group or a solid support medium;
each $R_m$ and $R_n$ is, independently, H, a nitrogen protecting group, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, wherein the substituent groups are selected from hydroxyl, amino, alkoxy, carboxy, benzyl, phenyl, nitro, thiol, thioalkoxy, halogen, alkyl, aryl, alkenyl, alkynyl; $NH_3^+$, $N(R_u)(R_v)$, guanidino and acyl where said acyl is an acid amide or an ester;
or $R_k$ and $R_m$, together, are a nitrogen protecting group, are joined in a ring structure that optionally includes an additional heteroatom selected from N and O or are a chemical functional group;
$R_i$ is $OR_z$, $SR_z$, or $N(R_z)_2$;
each $R_z$ is, independently, H, $C_1$-$C_8$ alkyl, $C_1$-$C_8$ haloalkyl, C(=NH)N(H)$R_u$, C(=O)N(H)$R_u$, or OC(=O)N(H)$R_u$;
$R_f$, $R_g$ and $R_h$ comprise a ring system having from about 4 to about 7 carbon atoms or having from about 3 to about 6 carbon atoms and 1 or 2 heteroatoms wherein said heteroatoms are selected from oxygen, nitrogen and sulfur and wherein said ring system is aliphatic, unsaturated aliphatic, aromatic, or saturated or unsaturated heterocyclic;
$R_j$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(R_k)(R_m)OR_k$, halo, $SR_k$ or CN;
$m_a$ is 1 to about 10;
each mb is, independently, 0 or 1;
mc is 0 or an integer from 1 to 10;
md is an integer from 1 to 10;
me is from 0, 1 or 2; and
provided that when mc is 0, md is greater than 1.

Representative substituents groups of Formula I are disclosed in U.S. patent application Ser. No. 09/130,973, filed Aug. 7, 1998, entitled "Capped 2'-Oxyethoxy Oligonucleotides," hereby incorporated by reference in its entirety.

Representative cyclic substituent groups of Formula II are disclosed in U.S. patent application Ser. No. 09/123,108, filed Jul. 27, 1998, entitled "RNA Targeted 2'-Oligomeric compounds that are Conformationally Preorganized," hereby incorporated by reference in its entirety.

Particularly preferred sugar substituent groups include $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3]_2$, where n and m are from 1 to about 10.

Representative guanidino substituent groups that are shown in formula III and IV are disclosed in co-owned U.S. patent application Ser. No. 09/349,040, entitled "Functionalized Oligomers", filed Jul. 7, 1999, hereby incorporated by reference in its entirety.

Representative acetamido substituent groups are disclosed in U.S. Pat. No. 6,147,200 which is hereby incorporated by reference in its entirety.

Representative dimethylaminoethyloxyethyl substituent groups are disclosed in International Patent Application PCT/US99/17895, entitled "2'-O-Dimethylaminoethyl-oxyethyl-Oligomeric compounds", filed Aug. 6, 1999, hereby incorporated by reference in its entirety.

Modified Nucleobases/Naturally Occurring Nucleobases

Oligomeric compounds may also include nucleobase (often referred to in the art simply as "base" or "heterocyclic base moiety") modifications or substitutions. As used herein, "unmodified" or "natural" nucleobases include the purine bases adenine (A) and guanine (G), and the pyrimidine bases thymine (T), cytosine (C) and uracil (U). Modified nucleobases also referred herein as heterocyclic base moieties include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH₃) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deaza-guanine and 7-deazaadenine and 3-deazaguanine and 3-deazaadenine.

Heterocyclic base moieties may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278) and are presently preferred base substitutions, even more particularly when combined with 2'-O-methoxyethyl sugar modifications.

Oligomeric compounds of the present invention can also include polycyclic heterocyclic compounds in place of one or more heterocyclic base moieties. A number of tricyclic heterocyclic compounds have been previously reported. These compounds are routinely used in antisense applications to increase the binding properties of the modified strand to a target strand. The most studied modifications are targeted to guanosines hence they have been termed G-clamps or cytidine analogs. Many of these polycyclic heterocyclic compounds have the general formula:

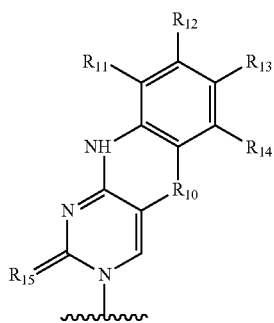

Representative cytosine analogs that make 3 hydrogen bonds with a guanosine in a second strand include 1,3-diazaphenoxazine-2-one ($R_{10}$=O, $R_{11}$-$R_{14}$=H) [Kurchavov, et al., *Nucleosides and Nucleotides*, 1997, 16, 1837-1846], 1,3-diazaphenothiazine-2-one ($R_{10}$=S, $R_{11}$-$R_{14}$=H), [Lin, K.-Y.; Jones, R. J.; Matteucci, M. J. Am. Chem. Soc. 1995, 117, 3873-3874] and 6,7,8,9-tetrafluoro-1,3-diazaphenoxazine-2-one ($R_{10}$=O, $R_{11}$-$R_{14}$=F) [Wang, J.; Lin, K.-Y., Matteucci, M. Tetrahedron Lett. 1998, 39, 8385-8388]. Incorporated into oligonucleotides these base modifications were shown to hybridize with complementary guanine and the latter was also shown to hybridize with adenine and to enhance helical thermal stability by extended stacking interactions (also see U.S. patent application entitled "Modified Peptide Nucleic Acids" filed May 24, 2002, Ser. No. 10/155,920; and U.S. patent application entitled "Nuclease Resistant Chimeric Oligonucleotides" filed May 24, 2002, Ser. No. 10/013,295, both of which are herein incorporated by reference in their entirety).

Further helix-stabilizing properties have been observed when a cytosine analog/substitute has an aminoethoxy moiety attached to the rigid 1,3-diazaphenoxazine-2-one scaffold ($R_{10}$=O, $R_{11}$=—O—(CH$_2$)$_2$—NH$_2$, $R_{12\text{-}14}$=H) [Lin, K.-Y.; Matteucci, M. J. Am. Chem. Soc. 1998, 120, 8531-8532]. Binding studies demonstrated that a single incorporation could enhance the binding affinity of a model oligonucleotide to its complementary target DNA or RNA with a $\Delta T_m$ of up to 18° relative to 5-methyl cytosine (dC5$^{me}$), which is the highest known affinity enhancement for a single modification, yet. On the other hand, the gain in helical stability does not compromise the specificity of the oligonucleotides. The $T_m$ data indicate an even greater discrimination between the perfect match and mismatched sequences compared to dC5$^{me}$. It was suggested that the tethered amino group serves as an additional hydrogen bond donor to interact with the Hoogsteen face, namely the O6, of a complementary guanine thereby forming 4 hydrogen bonds. This means that the increased affinity of G-clamp is mediated by the combination of extended base stacking and additional specific hydrogen bonding.

Further tricyclic heterocyclic compounds and methods of using them that are amenable to the present invention are disclosed in U.S. Pat. No. 6,028,183 and U.S. Pat. No. 6,007, 992, the contents of both are incorporated herein in their entirety.

The enhanced binding affinity of the phenoxazine derivatives together with their uncompromised sequence specificity makes them valuable nucleobase analogs for the development of more potent antisense-based drugs. In fact, promising data have been derived from in vitro experiments demonstrating that heptanucleotides containing phenoxazine substitutions are capable to activate RNaseH, enhance cellular uptake and exhibit an increased antisense activity [Lin, K.-Y; Mafteucci, M. J. Am. Chem. Soc. 1998, 120, 8531-8532]. The activity enhancement was even more pronounced in case of G-clamp, as a single substitution was shown to significantly improve the in vitro potency of a 20mer 2'-deoxyphosphorothioate oligonucleotides [Flanagan, W. M.; Wolf, J. J.; Olson, P.; Grant, D.; Lin, K.-Y.; Wagner, R. W.; Matteucci, M. Proc. Natl. Acad. Sci. USA, 1999, 96, 3513-3518]. Nevertheless, to optimize oligonucleotide design and to better understand the impact of these heterocyclic modifications on the biological activity, it is important to evaluate their effect on the nuclease stability of the oligomers.

Further modified polycyclic heterocyclic compounds useful as heterocyclic bases are disclosed in but not limited to, the above noted U.S. Pat. No. 3,687,808, as well as U.S. Pat. Nos. 4,845,205; 5,130,302; 5,134,066; 5,175,273; 5,367,066; 5,432,272; 5,434,257; 5,457,187; 5,459,255; 5,484,908; 5,502,177; 5,525,711; 5,552,540; 5,587,469; 5,594,121, 5,596,091; 5,614,617; 5,645,985; 5,646,269; 5,750,692; 5,830,653; 5,763,588; 6,005,096; and 5,681,941, and U.S. patent application Ser. No. 09/996,292 filed Nov. 28, 2001, each of which is herein incorporated by reference.

Conjugates

Oligomeric compounds used in the compositions of the present invention can also be modified to have one or more moieties or conjugates for enhancing the activity, cellular distribution or cellular uptake of the resulting oligomeric compounds. In one embodiment such modified oligomeric compounds are prepared by covalently attaching conjugate groups to functional groups such as hydroxyl or amino groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluoresceins, rhodamines, coumarins, and dyes such as including Cy3 and Alexa. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992 the entire disclosure of which is incorporated herein by reference.

Conjugate moieties include but are not limited to lipid moieties such as a cholesterol moiety (Letsinger et al., *Proc. Natl. Acad. Sci. USA*, 1989, 86, 6553-6556), cholic acid (Manoharan et al., *Bioorg. Med. Chem. Let.*, 1994, 4, 1053-1060), a thioether, e.g., hexyl-5-tritylthiol (Manoharan et al., *Ann. N.Y. Acad. Sci.*, 1992, 660, 306-309; Manoharan et al., *Bioorg. Med. Chem. Let.*, 1993, 3, 2765-2770), a thiocholesterol (Oberhauser et al., *Nucl. Acids Res.*, 1992, 20, 533-538), an aliphatic chain, e.g., dodecandiol or undecyl residues (Saison-Behmoaras et al., *EMBO J.*, 1991, 10, 1111-1118; Kabanov et al., *FEBS Lett.*, 1990, 259, 327-330; Svinarchuk et al., *Biochimie*, 1993, 75, 49-54), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36, 3651-3654; Shea et al., *Nucl. Acids Res.*, 1990, 18, 3777-3783), a polyamine or a polyethylene glycol chain (Manoharan et al., *Nucleosides & Nucleotides*, 1995, 14, 969-973), or adamantane acetic acid (Manoharan et al., *Tetrahedron Lett.*, 1995, 36, 3651-3654), a palmityl moiety (Mishra et al., *Biochim. Biophys. Acta*, 1995, 1264, 229-237), or an octadecylamine or hexylamino-carbonyl-oxycholesterol moiety (Crooke et al., *J. Pharmacol. Exp. Ther.*, 1996, 277, 923-937.

The oligomeric compounds of the invention may also be conjugated to active drug substances, for example, aspirin, warfarin, phenylbutazone, ibuprofen, suprofen, fenbufen, ketoprofen, (s)-(+)-pranoprofen, carprofen, dansylsarcosine, 2,3,5-triiodobenzoic acid, flufenamic acid, folinic acid, a benzothiadiazide, chlorothiazide, a diazepine, indo-methicin, a barbiturate, a cephalosporin, a sulfa drug, an antidiabetic, an antibacterial or an antibiotic. Oligonucleotide-drag conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

Oligomeric compounds used in the compositions of the present invention can also be modified to have one or more stabilizing groups that are generally attached to one or both termini of oligomeric compounds to enhance properties such as for example nuclease stability. Included in stabilizing groups are cap structures. By "cap structure or terminal cap moiety" is meant chemical modifications, which have been incorporated at either terminus of oligonucleotides (see for example Wincott et al., WO 97/26270, incorporated by reference herein). These terminal modifications protect the oligomeric compounds having terminal nucleic acid molecules from exonuclease degradation, and can help in delivery and/or localization within a cell. The cap can be present at the 5'-terminus (5'-cap) or at the 3'-terminus (3'-cap) or can be present on both termini. In non-limiting examples, the 5'-cap includes inverted abasic residue (moiety), 4',5'-methylene nucleotide; 1-(beta-D-erythrofuranosyl) nucleotide, 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl riucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety (for more details see Wincott et al., International PCT publication No. WO 97/26270, incorporated by reference herein).

Particularly preferred 3'-cap structures of the present invention include, for example 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Tyer, 1993, Tetrahedron 49, 1925; incorporated by reference herein).

Further 3' and 5'-stabilizing groups that can be used to cap one or both ends of an oligomeric compound to impart nuclease stability include those disclosed in WO 03/004602 published on Jan. 16, 2003.

3'-Endo Modifications

In one aspect of the present invention oligomeric compounds include nucleosides synthetically modified to induce a 3'-endo sugar conformation. A nucleoside can incorporate synthetic modifications of the heterocyclic base, the sugar moiety or both to induce a desired 3'-endo sugar conformation. These modified nucleosides are used to mimic RNA like nucleosides so that particular properties of an oligomeric compound can be enhanced while maintaining the desirable 3'-endo conformational geometry. There is an apparent preference for an RNA type duplex (A form helix, predominantly 3'-endo) as a requirement (e.g. trigger) of RNA interference which is supported in part by the fact that duplexes composed of 2'-deoxy-2'-F-nucleosides appears efficient in triggering RNAi response in the *C. elegans* system. Properties that are enhanced by using more stable 3'-endo nucleosides include but aren't limited to modulation of pharmacokinetic properties through modification of protein binding, protein off-rate, absorption and clearance; modulation of nuclease stability as well as chemical stability; modulation of the binding affinity and specificity of the oligomer (affinity and specificity for enzymes as well as for complementary sequences); and increasing efficacy of RNA cleavage. The present invention provides oligomeric triggers of RNAi having one or more nucleosides modified in such a way as to favor a C3'-endo type conformation.

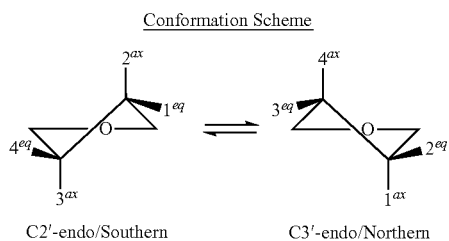

Conformation Scheme

C2'-endo/Southern    C3'-endo/Northern

Nucleoside conformation is influenced by various factors including substitution at the 2', 3' or 4'-positions of the pentofuranosyl sugar. Electronegative substituents generally prefer the axial positions, while sterically demanding substituents generally prefer the equatorial positions (Principles of Nucleic Acid Structure, Wolfgang Sanger, 1984, Springer-Verlag.) Modification of the 2' position to favor the 3'-endo conformation can be achieved while maintaining the 2'-OH as a recognition element (Gallo et al., Tetrahedron (2001), 57, 5707-5713. Harry-O'kuru et al., J. Org. Chem., (1997), 62 (6), 1754-1759 and Tang et al., J. Org. Chem. (1999), 64, 747-754). Alternatively, preference for the 3'-endo conformation can be achieved by deletion of the 2'-OH as exemplified by 2'deoxy-2'F-nucleosides (Kawasaki et al., J. Med. Chem. (1993), 36, 831-841), which adopts the 3'-endo conformation positioning the electronegative fluorine atom in the axial position. Other modifications of the ribose ring, for example substitution at the 4'-position to give 4'-F modified nucleosides (Guillerm et al., Bioorganic and Medicinal Chemistry Letters (1995), 5, 1455-1460 and Owen et al., J. Org. Chem. (1976), 41, 3010-3017), or for example modification to yield methanocarba nucleoside analogs (Jacobson et al., J. Med. Chem. Lett. (2000), 43, 2196-2203 and Lee et al., Bioorganic and Medicinal Chemistry Letters (2001), 11, 1333-1337) also induce preference for the 3'-endo conformation. Along similar lines, oligomeric triggers of RNAi response might be composed of one or more nucleosides modified in such a way that conformation is locked into a C3'-endo type conformation, i.e. Locked Nucleic Acid (LNA, Singh et al, Chem. Commun. (1998), 4, 455-456), and ethylene bridged Nucleic Acids (ENA, Morita et al, Bioorganic & Medicinal Chemistry Letters (2002), 12, 73-76).

The preferred conformation of modified nucleosides and their oligomers can be estimated by various methods such as molecular dynamics calculations, nuclear magnetic resonance spectroscopy and CD measurements. Hence, modifications predicted to induce RNA like conformations, A-form duplex geometry in an oligomeric context, are selected for use in the modified oligonucleotides of the present invention. The synthesis of numerous of the modified nucleosides amenable to the present invention are known in the art (see for example, Chemistry of Nucleosides and Nucleotides Vol 1-3, ed. Leroy B. Townsend, 1988, Plenum press., and the examples section below).

In one aspect, the present invention is directed to oligomers that are prepared having enhanced properties compared to native RNA against nucleic acid targets. A target is identified and an oligomer is selected having an effective length and sequence that is complementary to a portion of the target sequence. Each nucleoside of the selected sequence is scrutinized for possible enhancing modifications. A preferred modification would be the replacement of one or more RNA nucleosides with nucleosides that have the same 3'-endo conformational geometry. Such modifications can enhance chemical and nuclease stability relative to native RNA while at the same time being much cheaper and easier to synthesize and/or incorporate into an oligonucleotide. The selected sequence can be further divided into regions and the nucleosides of each region evaluated for enhancing modifications that can be the result of a chimeric configuration. Consideration is also given to the 5' and 3'-termini as there are often advantageous modifications that can be made to one or more of the terminal nucleosides. The oligomeric compounds of the present invention include at least one 5'-modified phosphate group on a single strand or on at least one 5'-position of a double stranded sequence or sequences. Further modifications are also considered such as internucleoside linkages, conjugate groups, substitute sugars or bases, substitution of one or more nucleosides with nucleoside mimetics and any other modification that can enhance the selected sequence for its intended target.

The terms used to describe the conformational geometry of homoduplex nucleic acids are "A Form" for RNA and "B Form" for DNA. The respective conformational geometry for RNA and DNA duplexes was determined from X-ray diffraction analysis of nucleic acid fibers (Arnott and Hukins, *Biochem. Biophys. Res. Comm.*, 1970, 47, 1504). In general, RNA:RNA duplexes are more stable and have higher melting temperatures (Tm's) than DNA:DNA duplexes (Sanger et al., Principles of Nucleic Acid Structure, 1984, Springer-Verlag; New York, N.Y.; Lesnik et al., Biochemistry, 1995, 34, 10807-10815; Conte et al., Nucleic Acids Res., 1997, 25, 2627-2634). The increased stability of RNA has been attributed to several structural features, most notably the improved base stacking interactions that result from an A-form geometry (Searle et al., Nucleic Acids Res., 1993, 21, 2051-2056). The presence of the 2' hydroxyl in RNA biases the sugar toward a C3' endo pucker, i.e., also designated as Northern pucker, which causes the duplex to favor the A-form geometry. In addition, the 2' hydroxyl groups of RNA can form a network of water mediated hydrogen bonds that help stabilize the RNA duplex (Egli et al., Biochemistry, 1996, 35, 8489-8494). On the other hand, deoxy nucleic acids prefer a C2' endo sugar pucker, i.e., also known as Southern pucker, which is thought to impart a less stable B-form geometry (Sanger, W. (1984) Principles of Nucleic Acid Structure, Springer-Verlag, New York, N.Y.). As used herein, B-form geometry is inclusive of both C2'-endo pucker and O4'-endo pucker. This is consistent with Berger, et. al., *Nucleic Acids Research*, 1998, 26, 2473-2480, who pointed out that in considering the furanose conformations which give rise to B-form duplexes consideration should also be given to a O4'-endo pucker contribution.

DNA:RNA hybrid duplexes, however, are usually less stable than pure RNA:RNA duplexes, and depending on their sequence may be either more or less stable than DNA:DNA duplexes (Searle et al., *Nucleic Acids Res.*, 1993, 21, 2051-2056). The structure of a hybrid duplex is intermediate between A- and B-form geometries, which may result in poor stacking interactions (Lane et al., *Eur. J. Biochem.*, 1993, 215, 297-306; Fedoroff et al., *J. Mol. Biol.*, 1993, 233, 509-523; Gonzalez et al., *Biochemistry*, 1995, 34, 4969-4982; Horton et al., *J. Mol. Biol.*, 1996, 264, 521-533). The stability of the duplex formed between a target RNA and a synthetic sequence is central to therapies such as but not limited to antisense and RNA interference as these mechanisms require the binding of a synthetic oligomer strand to an RNA target strand. In the case of antisense, effective inhibition of the mRNA requires that the antisense DNA have a very high binding affinity with the mRNA. Otherwise the desired interaction between the synthetic oligomer strand and target mRNA strand will occur infrequently, resulting in decreased efficacy.

One routinely used method of modifying the sugar puckering is the substitution of the sugar at the 2'-position with a substituent group that influences the sugar geometry. The influence on ring conformation is dependant on the nature of the substituent at the 2'-position. A number of different substituents have been studied to determine their sugar puckering effect. For example, 2'-halogens have been studied showing that the 2'-fluoro derivative exhibits the largest population (65%) of the C3'-endo form, and the 2'-iodo exhibits the lowest population (7%). The populations of adenosine (2'-OH) versus deoxy-adenosine (2'-H) are 36% and 19%, respectively. Furthermore, the effect of the 2'-fluoro group of adenosine dimers (2'-deoxy-2'-fluoroadenosine-2'-deoxy-2'-fluoro-adenosine) is further correlated to the stabilization of the stacked conformation.

As expected, the relative duplex stability can be enhanced by replacement of 2'-OH groups with 2'-F groups thereby increasing the C3'-endo population. It is assumed that the highly polar nature of the 2'-F bond and the extreme preference for C3'-endo puckering may stabilize the stacked conformation in an A-form duplex. Data from UV hypochromicity, circular dichroism, and $^1$H NMR also indicate that the degree of stacking decreases as the electronegativity of the halo substituent decreases. Furthermore, steric bulk at the 2'-position of the sugar moiety is better accommodated in an A-form duplex than a B-form duplex. Thus, a 2'-substituent on the 3'-terminus of a dinucleoside monophosphate is thought to exert a number of effects on the stacking conformation: steric repulsion, furanose puckering preference, electrostatic repulsion, hydrophobic attraction, and hydrogen bonding capabilities. These substituent effects are thought to be determined by the molecular size, electronegativity, and hydrophobicity of the substituent. Melting temperatures of complementary strands is also increased with the 2'-substituted adenosine diphosphates. It is not clear whether the 3'-endo preference of the conformation or the presence of the substituent is responsible for the increased binding. However, greater overlap of adjacent bases (stacking) can be achieved with the 3'-endo conformation.

One synthetic 2'-modification that imparts increased nuclease resistance and a very high binding affinity to nucleotides is the 2-methoxyethoxy (2'-MOE, 2'-OCH$_2$CH$_2$OCH$_3$) side chain (Baker et al., *J. Biol. Chem.*, 1997, 272, 11944-12000). One of the immediate advantages of the 2'-MOE substitution is the improvement in binding affinity, which is greater than many similar 2' modifications such as O-methyl, O-propyl, and O-aminopropyl. Oligomers having the 2'-O-methoxyethyl substituent also have been shown to be antisense inhibitors of gene expression with promising features for in vivo use (Martin, P., *Helv. Chim. Acta*, 1995, 78, 486-504; Altmann et al., *Chimia*, 1996, 50, 168-176; Altmann et al., *Biochem. Soc. Trans.*, 1996, 24, 630-637; and Altmann et al., *Nucleosides Nucleotides*, 1997, 16, 917-926). Relative to DNA, the oligomers having the 2'-MOE modification displayed improved RNA affinity and higher nuclease resistance. Chimeric oligomers having 2'-MOE substituents in the wing nucleosides and an internal region of deoxy-phosphorothioate nucleotides (also termed a gapped oligomer or gapmer) have shown effective reduction in the growth of tumors in animal models at low doses. 2'-MOE substituted oligomers have also shown outstanding promise as antisense compounds in several disease states. One such MOE substituted oligomer is presently being investigated in clinical trials for the treatment of CMV retinitis.

To better understand the higher RNA affinity of 2'-O-methoxyethyl substituted RNA and to examine the conformational properties of the 2'-O-methoxyethyl substituent, two dodecamer oligonucleotides were synthesized having SEQ ID NO: 1 (CGC GAA UUC GCG) and SEQ ID NO: 2 (GCG CUU AAG CGC). These self-complementary strands have every 2'-position modified with a 2'-O-methoxyethyl. The duplex was crystallized at a resolution of 1.7 Ångstrom and the crystal structure was determined. The conditions used for the crystallization were 2 mM oligonucleotide, 50 mM Na Hepes pH 6.2-7.5, 10.50 mM MgCl$_2$, 15% PEG 400. The crystal data showed: space group C2, cell constants a=41.2 Å, b=34.4 Å, c=46.6 Å, =92.4°. The resolution was 1.7 Å at −170° C. The current R=factor was 20% (R$_{free}$ 26%).

This crystal structure is believed to be the first crystal structure of a fully modified RNA oligonucleotide analogue. The duplex adopts an overall A-form conformation and all modified sugars display C3'-endo pucker. In most of the 2'-O-substituents, the torsion angle around the A'-B' bond, as depicted in Structure II below, of the ethylene glycol linker has a gauche conformation. For 2'-MOE, A' and B' of Structure II below are methylene moieties of the ethyl portion of the MOE and R' is the methoxy portion.

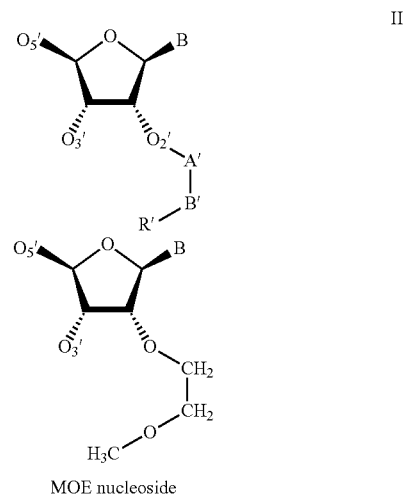

II

MOE nucleoside

In the crystal, the 2'-MOE RNA duplex adopts a general orientation such that the crystallographic 2-fold rotation axis does not coincide with the molecular 2-fold rotation axis. The duplex adopts the expected A-type geometry and all of the 24 2'-MOE substituents were visible in the electron density maps at full resolution. The electron density maps as well as the temperature factors of substituent atoms indicate flexibility of the 2'-MOE substituent in some cases.

Most of the 2'-MOE substituents display a gauche conformation around the C—C bond of the ethyl linker. However, in two cases, a trans conformation around the C—C bond is observed. The lattice interactions in the crystal include packing of duplexes against each other via their minor grooves. Therefore, for some residues, the conformation of the 2'-O-substituent is affected by contacts to an adjacent duplex. In general, variations in the conformation of the substituents (e.g. $g^+$ or $g^-$ around the C—C bonds) create a range of interactions between substituents, both inter-strand, across the minor groove, and intra-strand. At one location, atoms of substituents from two residues are in van der Waals contact across the minor groove. Similarly, a close contact occurs between atoms of substituents from two adjacent intra-strand residues.

Previously determined crystal structures of A-DNA duplexes were for those that incorporated isolated 2'-O-methyl T residues. In the crystal structure noted above for the 2'-MOE substituents, a conserved hydration pattern has been observed for the 2'-MOE residues. A single water molecule is seen located between O2', O3' and the methoxy oxygen atom of the substituent, forming contacts to all three of between 2.9 and 3.4 Å. In addition, oxygen atoms of substituents are involved in several other hydrogen bonding contacts. For example, the methoxy oxygen atom of a particular 2'-O-substituent forms a hydrogen bond to N3 of an adenosine from the opposite strand via a bridging water molecule.

In several cases a water molecule is trapped between the oxygen atoms O2', O3' and OC' of modified nucleosides. 2'-MOE substituents with trans conformation around the C—C bond of the ethylene glycol linker are associated with close contacts between OC' and N2 of a guanosine from the opposite strand, and, water-mediated, between OC' and N3(G). When combined with the available thermodynamic data for duplexes containing 2'-MOE modified strands, this crystal structure allows for further detailed structure-stability analysis of other modifications.

In extending the crystallographic structure studies, molecular modeling experiments were performed to study further enhanced binding affinity of oligonucleotides having 2'-O-modifications. The computer simulations were conducted on compounds of SEQ ID NO: 1, above, having 2'-O-modifications located at each of the nucleosides of the oligonucleotide. The simulations were performed with the oligonucleotide in aqueous solution using the AMBER force field method (Cornell et al., *J. Am. Chem. Soc.*, 1995, 117, 5179-5197) (modeling software package from UCSF, San Francisco, Calif.). The calculations were performed on an Indigo2 SGI machine (Silicon Graphics, Mountain View, Calif.).

Further 2'-O-modifications that will have a 3'-endo sugar influence include those having a ring structure that incorporates a two atom portion corresponding to the A' and B' atoms of Structure II. The ring structure is attached at the 2' position of a sugar moiety of one or more nucleosides that are incorporated into an oligonucleotide. The 2'-oxygen of the nucleoside links to a carbon atom corresponding to the A' atom of Structure II. These ring structures can be aliphatic, unsaturated aliphatic, aromatic or heterocyclic. A further atom of the ring (corresponding to the B' atom of Structure II), bears a further oxygen atom, or a sulfur or nitrogen atom. This oxygen, sulfur or nitrogen atom is bonded to one or more hydrogen atoms, alkyl moieties, or haloalkyl moieties, or is part of a further chemical moiety such as a ureido, carbamate, amide or amidine moiety. The remainder of the ring structure restricts rotation about the bond joining these two ring atoms. This assists in positioning the "further oxygen, sulfur or nitrogen atom" (part of the R position as described above) such that the further atom can be located in close proximity to the 3'-oxygen atom (O3') of the nucleoside.

Another preferred 2'-sugar substituent group that gives a 3'-endo sugar conformational geometry is the 2'-OMe group. 2'-Substitution of guanosine, cytidine, and uridine dinucleoside phosphates with the 2'-OMe group showed enhanced stacking effects with respect to the corresponding native (2'-OH) species leading to the conclusion that the sugar is adopting a C3'-endo conformation. In this case, it is believed that the hydrophobic attractive forces of the methyl group tend to overcome the destabilizing effects of its steric bulk.

The ability of oligonucleotides to bind to their complementary target strands is compared by determining the melting temperature ($T_m$) of the hybridization complex of the oligonucleotide and its complementary strand. The melting temperature ($T_m$), a characteristic physical property of double helices, denotes the temperature (in degrees centigrade) at which 50% helical (hybridized) versus coil (unhybridized) forms are present. $T_m$ is measured by using the UV spectrum to determine the formation and breakdown (melting) of the hybridization complex. Base stacking, which occurs during hybridization, is accompanied by a reduction in UV absorption (hypochromicity). Consequently, a reduction in UV absorption indicates a higher $T_m$. The higher the $T_m$, the greater the strength of the bonds between the strands.

Freier and Altmann, Nucleic Acids Research, (1997) 25:4429-4443, have previously published a study on the influence of structural modifications of oligonucleotides on the stability of their duplexes with target RNA. In this study, the authors reviewed a series of oligonucleotides containing more than 200 different modifications that had been synthesized and assessed for their hybridization affinity and Tm. Sugar modifications studied included substitutions on the 2'-position of the sugar, 3'-substitution, replacement of the 4'-oxygen, the use of bicyclic sugars, and four member ring replacements. Several nucleobase modifications were also studied including substitutions at the 5, or 6 position of thymine, modifications of pyrimidine heterocycle and modifications of the purine heterocycle. Modified internucleoside linkages were also studied including neutral, phosphorus and non-phosphorus containing internucleoside linkages.

Increasing the percentage of C3'-endo sugars in a modified oligonucleotide targeted to an RNA target strand should pre-organize this strand for binding to RNA. Of the several sugar modifications that have been reported and studied in the literature, the incorporation of electronegative substituents such as 2'-fluoro or 2'-alkoxy shift the sugar conformation towards the 3' endo (northern) pucker conformation. This preorganizes an oligonucleotide that incorporates such modifications to have an A-form conformational geometry. This A-form conformation results in increased binding affinity of the oligonucleotide to a target RNA strand.

Molecular modeling experiments were performed to study further enhanced binding affinity of oligonucleotides having 2'-O-modifications. Computer simulations were conducted on compounds having SEQ ID NO: 1, r(CGC GAA UUC GCG), having 2'-O-modifications of the invention located at each of the nucleoside of the oligonucleotide. The simulations were performed with the oligonucleotide in aqueous solution using the AMBER force field method (Cornell et al., *J. Am. Chem. Soc.,* 1995, 117, 5179-5197) (modeling software package from UCSF, San Francisco, Calif.). The calculations were performed on an Indigo2 SGI machine (Silicon Graphics, Mountain View, Calif.).

In addition, for 2'-substituents containing an ethylene glycol motif, a gauche interaction between the oxygen atoms around the O—C—C—O torsion of the side chain may have a stabilizing effect on the duplex (Freier ibid.). Such gauche interactions have been observed experimentally for a number of years (Wolfe et al., *Acc. Chem. Res.,* 1972, 5, 102; Abe et al., *J. Am. Chem. Soc.,* 1976, 98, 468). This gauche effect may result in a configuration of the side chain that is favorable for duplex formation. The exact nature of this stabilizing configuration has not yet been explained. While we do not want to be bound by theory, it may be that holding the O—C—C—O torsion in a single gauche configuration, rather than a more random distribution seen in an alkyl side chain, provides an entropic advantage for duplex formation.

Representative 2'-substituent groups amenable to the present invention that give A-form conformational properties (3'-endo) to the resultant duplexes include 2'-O-alkyl, 2'-O-substituted alkyl and 2'-fluoro substituent groups. Preferred for the substituent groups are various alkyl and aryl ethers and thioethers, amines and monoalkyl and dialkyl substituted amines. It is further intended that multiple modifications can be made to one or more of the oligomeric compounds of the invention at multiple sites of one or more monomeric subunits (nucleosides are preferred) and or internucleoside linkages to enhance properties such as but not limited to activity in a selected application. Tables I through VII list nucleoside and internucleotide linkage modifications/replacements that have been shown to give a positive ΔTm per modification when the modification/replacement was made to a DNA strand that was hybridized to an RNA complement.

TABLE I

Modified DNA strand having 2'-substituent groups that gave an overall increase in Tm against an RNA complement:
Positive ΔTm/mod 2'-substituents 2'-OH
2'-O—$C_1$-$C_4$ alkyl
2'-O—$(CH_2)_2CH_3$
2'-O—$CH_2CH$=$CH_2$
2'-F
2'-O—$(CH_2)_2$—O—$CH_3$
2'-[O—$(CH_2)_2]_2$—O—$CH_3$
2'-[O—$(CH_2)_2]_3$—O—$CH_3$
2'-[O—$(CH_2)_2]_4$—O—$CH_3$
2'-[O—$(CH_2)_2]_3$—O—$(CH_2)_8CH_3$
2'-O—$(CH_2)_2CF_3$
2'-O—$(CH_2)_2OH$
2'-O—$(CH_2)_2F$
2'-O—$CH_2CH(CH_3)F$
2'-O—$CH_2CH(CH_2OH)OH$
2'-O—$CH_2CH(CH_2OCH_3)OCH_3$
2'-O—$CH_2CH(CH_3)OCH_3$
2'-O—$CH_2$—$C_{14}H_7O_2$(—$C_{14}H_7O_2$ = Anthraquinone)
2'-O—$(CH_2)_3$—$NH_2$*
2'-O—$(CH_2)_4$—$NH_2$*

*These modifications can increase the Tm of oligonucleotides but can also decrease the Tm depending on positioning and number (motiff dependant).

TABLE II

Modified DNA strand having modified sugar ring
(see structure x) that gave an
overall increase in Tm against an RNA complement:

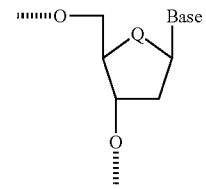

Positive ΔTm/mod

| Q | |
|---|---|
| | —S— |
| | —$CH_2$— |

Note:
In general ring oxygen substitution with sulfur or methylene had only a minor effect on Tm for the specific motiffs studied. Substitution at the 2'-position with groups shown to stabilize the duplex were destabilizing when $CH_2$ replaced the ring O. This is thought to be due to the necessary gauche interaction between the ring O with particular 2'-substituents (for example —O—$CH_3$ and —(O—$CH_2CH_2)_3$—O—$CH_3$.

TABLE III

Modified DNA strand having modified sugar ring
that give an overall increase in
Tm against an RNA complement:

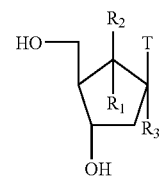

Positive ΔTm/mod

| —C(H)$R_1$ effects ($R_2$, $R_3$ both = H) | OH |
|---|---|
| | $CH_3$* |
| | $CH_2OH$* |
| | $OCH_3$* |

*These modifications can increase the Tm of oligonucleotides but can also decrease the Tm depending on positioning and number (motiff dependant).

TABLE IV

Modified DNA strand having bicyclic substitute sugar
modifications that give an overall increase in
Tm against an RNA complement:

| Formula | Positive ΔTm/mod |
|---|---|
| I | + |
| II | + |

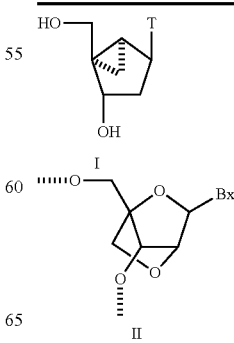

TABLE V

Modified DNA strand having modified heterocyclic base moieties that give an overall increase in Tm against an RNA complement:

Modification/Formula Positive ΔTm/mod

| Heterocyclic base modifications | 2-thioT |
| --- | --- |
| | 2'-O-methylpseudoU |
| | 7-halo-7-deaza purines |
| | 7-propyne-7-deaza purines |
| | 2-aminoA(2,6-diaminopurine) |

Modification/Formula Positive ΔTm/mod

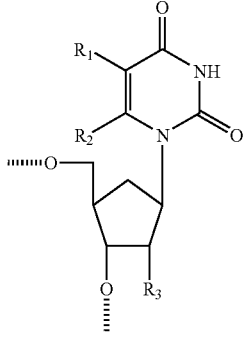

($R_2$, $R_3$ = H), $R_1$ = Br
C/C—$CH_3$
$(CH_2)_3NH_2$
$CH_3$

Motiffs-disubstitution

| $R_1$ = C/C—$CH_3$, $R_2$ = H, $R_3$ = | F |
| --- | --- |
| $R_1$ = C/C—$CH_3$, $R_2$ = H | $R_3$ = O—$(CH_2)_2$—O—$CH_3$ |
| $R_1$ = O—$CH_3$, $R_2$ = H, | $R_3$ = O—$(CH_2)_2$—O—$CH_3$* |

*This modification can increase the Tm of oligonucleotides but can also decrease the Tm depending on positioning and number (motiff dependant).

Substitution at $R_1$ can be stabilizing, substitution at $R_2$ is generally greatly destabilizing (unable to form anti conformation), motiffs with stabilizing 5 and 2'-substituent groups are generally additive e.g. increase stability.

Substitution of the O4 and O2 positions of 2'-O-methyl uridine was greatly duplex destabilizing as these modifications remove hydrogen binding sites that would be an expected result. 6-Aza T also showed extreme destabilization as this substitution reduces the $pK_a$ and shifts the nucleoside toward the enol tautomer resulting in reduced hydrogen bonding.

TABLE VI

DNA strand having at least one modified phosphorus containing internucleoside linkage and the effect on the Tm against an RNA complement:

| ΔTm/mod + | ΔTm/mod − |
| --- | --- |
| phosphoramidate (the 3'-bridging atom replaced with an N(H)R group, stabilization effect enhanced when also have 2'-F) | phosphorothioate[1] |
| | phosphoramidate[1] |
| | methyl phosphonates[1] |

([1]one of the non-bridging oxygen atoms replaced with S, N(H)R or —$CH_3$)

TABLE VII

DNA strand having at least one non-phosphorus containing internucleoside linkage and the effect on the Tm against an RNA complement:
Positive ΔTm/mod —$CH_2C(=O)NHCH_2$—*
—$CH_2C(=O)N(CH_3)CH_2$—*
—$CH_2C(=O)N(CH_2CH_2CH_3)CH_2$—*
—$CH_2C(=O)N(H)CH_2$— (motiff with 5'-propyne on T's)
—$CH_2N(H)C(=O)CH_2$—*
—$CH_2N(CH_3)OCH_2$—*
—$CH_2N(CH_3)N(CH_3)CH_2$—*

*This modification can increase the Tm of oligonucleotides but can also decrease the Tm depending on positioning and number (motiff dependant).
Notes:
In general carbon chain internucleotide linkages were destabilizing to duplex formation. This destabilization was not as severe when double and tripple bonds were utilized. The use of glycol and flexible ether linkages were also destabilizing.

Preferred ring structures of the invention for inclusion as a 2'-O modification include cyclohexyl, cyclopentyl and phenyl rings as well as heterocyclic rings having spacial footprints similar to cyclohexyl, cyclopentyl and phenyl rings. Particularly preferred 2'-O-substituent groups of the invention included but are not limited to 2'-O-(trans 2-methoxy cyclohexyl, 2'-O-(trans 2-methoxy cyclopentyl, 2'-O-(trans 2-ureido cyclohexyl) and 2'-O-(trans 2-methoxyphenyl).

Examples of some modified nucleosides that are expected to have 3'-endo sugar conformation are shown below in Table I. These examples are meant to be representative and not exhaustive.

TABLE I

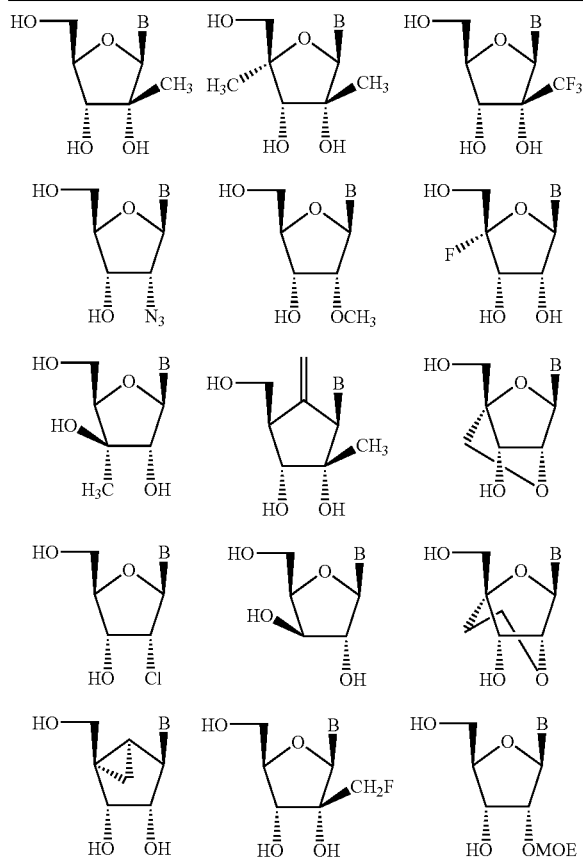

TABLE I-continued

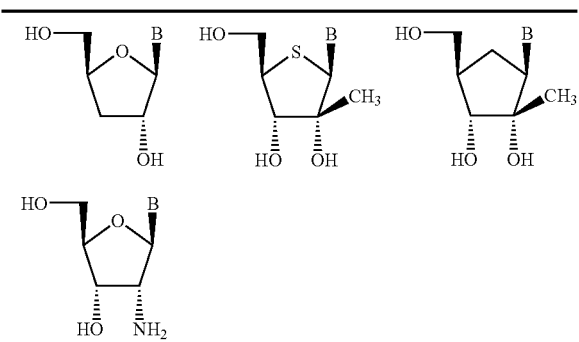

Although the overall stability of the DNA:RNA hybrids depends on several factors including sequence-dependencies and the purine content in the DNA or RNA strands DNA:RNA hybrids are usually less stable than RNA:RNA duplexes and, in some cases, even less stable than DNA:DNA duplexes. Available experimental data attributes the relatively lowered stability of DNA:RNA hybrids largely to its intermediate conformational nature between DNA:DNA (B-family) and RNA:RNA (A-family) duplexes. The overall thermodynamic stability of nucleic acid duplexes may originate from several factors including the conformation of backbone, base-pairing and stacking interactions. While it is difficult to ascertain the individual thermodynamic contributions to the overall stabilization of the duplex, it is reasonable to argue that the major factors that promote increased stability of hybrid duplexes are better stacking interactions (electrostatic π-π interactions) and more favorable groove dimensions for hydration. The C2'-S-methyl substitution has been shown to destabilize the hybrid duplex. The notable differences in the rise values among the three hybrids may offer some explanation. While the 2'-S-methyl group has a strong influence on decreasing the base-stacking through high rise values (~3.2 Å), the 2'-O-methyl group makes the overall structure more compact with a rise value that is equal to that of A-form duplexes (~2.6 Å). Despite its overall A-like structural features, the SMe_DNA:RNA hybrid structure possesses an average rise value of 3.2 Å which is quite close to that of B-family duplexes. In fact, some local base-steps (CG steps) may be observed to have unusually high rise values (as high as 4.5 Å). Thus, the greater destabilization of 2'-S-methyl substituted DNA:RNA hybrids may be partly attributed to poor stacking interactions.

Chemistries Defined

Unless otherwise defined herein, alkyl means $C_1$-$C_{12}$, preferably $C_1$-$C_8$, and more preferably $C_1$-$C_6$, straight or (where possible) branched chain aliphatic hydrocarbyl.

Unless otherwise defined herein, heteroalkyl means $C_1$-$C_{12}$, preferably $C_1$-$C_8$, and more preferably $C_1$-$C_6$, straight or (where possible) branched chain aliphatic hydrocarbyl containing at least one, and preferably about 1 to about 3, hetero atoms in the chain, including the terminal portion of the chain. Preferred heteroatoms include N, O and S.

Unless otherwise defined herein, cycloalkyl means $C_3$-$C_{12}$, preferably $C_3$-$C_8$, and more preferably $C_3$-$C_6$, aliphatic hydrocarbyl ring.

Unless otherwise defined herein, alkenyl means $C_2$-$C_{12}$, preferably $C_2$-$C_8$, and more preferably $C_2$-$C_6$ alkenyl, which may be straight or (where possible) branched hydrocarbyl moiety, which contains at least one carbon-carbon double bond.

Unless otherwise defined herein, alkynyl means $C_2$-$C_{12}$, preferably $C_2$-$C_8$, and more preferably $C_2$-$C_6$ alkynyl, which may be straight or (where possible) branched hydrocarbyl moiety, which contains at least one carbon-carbon triple bond.

Unless otherwise defined herein, heterocycloalkyl means a ring moiety containing at least three ring members, at least one of which is carbon, and of which 1, 2 or three ring members are other than carbon. Preferably the number of carbon atoms varies from 1 to about 12, preferably 1 to about 6, and the total number of ring members varies from three to about 15, preferably from about 3 to about 8. Preferred ring heteroatoms are N, O and S. Preferred heterocycloalkyl groups include morpholino, thiomorpholino, piperidinyl, piperazinyl, homopiperidinyl, homopiperazinyl, homomorpholino, homothiomorpholino, pyrrolodinyl, tetrahydrooxazolyl, tetrahydroimidazolyl, tetrahydrothiazolyl, tetrahydroisoxazolyl, tetrahydropyrrazolyl, furanyl, pyranyl, and tetrahydroisothiazolyl.

Unless otherwise defined herein, aryl means any hydrocarbon ring structure containing at least one aryl ring. Preferred aryl rings have about 6 to about 20 ring carbons. Especially preferred aryl rings include phenyl, napthyl, anthracenyl, and phenanthrenyl.

Unless otherwise defined herein, hetaryl means a ring moiety containing at least one fully unsaturated ring, the ring consisting of carbon and non-carbon atoms. Preferably the ring system contains about 1 to about 4 rings. Preferably the number of carbon atoms varies from 1 to about 12, preferably 1 to about 6, and the total number of ring members varies from three to about 15, preferably from about 3 to about 8. Preferred ring heteroatoms are N, O and S. Preferred hetaryl moieties include pyrazolyl, thiophenyl, pyridyl, imidazolyl, tetrazolyl, pyridyl, pyrimidinyl, purinyl, quinazolinyl, quinoxalinyl, benzimidazolyl, benzothiophenyl, etc.

Unless otherwise defined herein, where a moiety is defined as a compound moiety, such as hetarylalkyl (hetaryl and alkyl), aralkyl (aryl and alkyl), etc., each of the sub-moieties is as defined herein.

Unless otherwise defined herein, an electron withdrawing group is a group, such as the cyano or isocyanato group that draws electronic charge away from the carbon to which it is attached. Other electron withdrawing groups of note include those whose electronegativities exceed that of carbon, for example halogen, nitro, or phenyl substituted in the ortho- or para-position with one or more cyano, isothiocyanato, nitro or halo groups.

Unless otherwise defined herein, the terms halogen and halo have their ordinary meanings. Preferred halo (halogen) substituents are Cl, Br, and I.

The aforementioned optional substituents are, unless otherwise herein defined, suitable substituents depending upon desired properties. Included are halogens (Cl, Br, I), alkyl, alkenyl, and alkynyl moieties, $NO_2$, $NH_3$ (substituted and unsubstituted), acid moieties (e.g. —$CO_2H$, —$OSO_3H_2$, etc.), heterocycloalkyl moieties, hetaryl moieties, aryl moieties, etc.

In all the preceding formulae, the squiggle (~) indicates a bond to an oxygen or sulfur of the 5'-phosphate. Phosphate protecting groups include those described in U.S. Pat. No. 5,760,209, U.S. Pat. No. 5,614,621, U.S. Pat. No. 6,051,699, U.S. Pat. No. 6,020,475, U.S. Pat. No. 6,326,478, U.S. Pat. No. 6,169,177, U.S. Pat. No. 6,121,437, U.S. Pat. No. 6,465,628 each of which is expressly incorporated herein by reference in its entirety.

Oligomer Synthesis

Oligomerization of modified and unmodified nucleosides is performed according to literature procedures for DNA (Protocols for Oligonucleotides and Analogs, Ed. Agrawal (1993), Humana Press) and/or RNA (Scaringe, Methods (2001), 23, 206-217. Gait et al., Applications of Chemically synthesized RNA in RNA:Protein Interactions, Ed. Smith (1998), 1-36. Gallo et al., Tetrahedron (2001), 57, 5707-5713) synthesis as appropriate. In addition specific protocols for the synthesis of oligomeric compounds of the invention are illustrated in the examples below.

The oligomeric compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The present invention is also useful for the preparation of oligomeric compounds incorporating at least one 2'-O-protected nucleoside. After incorporation and appropriate deprotection the 2'-O-protected nucleoside will be converted to a ribonucleoside at the position of incorporation. The number and position of the 2-ribonucleoside units in the final oligomeric compound can vary from one at any site or the strategy can be used to prepare up to a full 2'-OH modified oligomeric compound. All 2'-O-protecting groups amenable to the synthesis of oligomeric compounds are included in the present invention. In general a protected nucleoside is attached to a solid support by for example a succinate linker. Then the oligonucleotide is elongated by repeated cycles of deprotecting the 5'-terminal hydroxyl group, coupling of a further nucleoside unit, capping and oxidation (alternatively sulfurization). In a more frequently used method of synthesis the completed oligonucleotide is cleaved from the solid support with the removal of phosphate protecting groups and exocyclic amino protecting groups by treatment with an ammonia solution. Then a further deprotection step is normally required for removal of the more specialized protecting groups used for the protection of 2'-hydroxyl groups thereby affording the fully deprotected oligonucleotide.

A large number of 2'-O-protecting groups have been used for the synthesis of oligoribonucleotides but over the years more effective groups have been discovered. The key to an effective 2'-O-protecting group is that it is capable of selectively being introduced at the 2'-O-position and that it can be removed easily after synthesis without the formation of unwanted side products. The protecting group also needs to be inert to the normal deprotecting, coupling, and capping steps required for oligoribonucleotide synthesis. Some of the protecting groups used initially for oligoribonucleotide synthesis included tetrahydropyran-1-yl and 4-methoxytetrahydropyran-4-yl. These two groups are not compatible with all 5'-O-protecting groups so modified versions were used with 5'-DMT groups such as 1-(2-fluorophenyl)-4-methoxypiperidin-4-yl (Fpmp). Reese has identified a number of piperidine derivatives (like Fpmp) that are useful in the synthesis of oligoribonucleotides including 1-[(chloro-4-methyl)phenyl]-4'-methoxypiperidin-4-yl (Reese et al., Tetrahedron Lett., 1986, (27), 2291). Another approach was to replace the standard 5'-DMT (dimethoxytrityl) group with protecting groups that were removed under non-acidic conditions such as levulinyl and 9-fluorenylmethoxycarbonyl. Such groups enable the use of acid labile 2'-protecting groups for oligoribonucleotide synthesis. Another more widely used protecting group initially used for the synthesis of oligoribonucleotides was the t-butyldimethylsilyl group (Ogilvie et al., Tetrahedron Lett., 1974, 2861; Hakimelahi et al., Tetrahedron Lett., 1981, (22), 2543; and Jones et al., J. Chem. Soc. Perkin I., 2762). The 2'-O-protecting groups can require special reagents for their removal such as for example the t-butyldimethylsilyl group is normally removed after all other cleaving/deprotecting steps by treatment of the oligomeric compound with tetrabutylammonium fluoride (TBAF).

One group of researchers examined a number of 2'-O-protecting groups (Pitsch, S., Chimia, 2001, (55), 320-324). The group examined fluoride labile and photolabile protecting groups that are removed using moderate conditions. One photolabile group that was examined was the [2-(nitrobenzyl)oxy]methyl (nbm) protecting group (Schwartz et al., Bioorg. Med. Chem. Lett., 1992, (2), 1019). Other groups examined included a number structurally related formaldehyde acetal-derived, 2'-O-protecting groups. Also prepared were a number of related protecting groups for preparing 2'-O-alkylated nucleoside phosphoramidites including 2'-O-[(triisopropylsilyl)oxy]methyl (2'-O—CH$_2$—O—Si(iPr)$_3$, TOM). One 2'-O-protecting group that was prepared to be used orthogonally to the TOM group was 2'-O—[(R)-1-(2-nitrophenyl)ethyloxy)methyl]((R)-mnbm).

Another strategy using a fluoride labile 5'-O-protecting group (non-acid labile) and an acid labile 2'-O-protecting group has been reported (Scaringe, Stephen A., Methods, 2001, (23) 206-217). A number of possible silyl ethers were examined for 5'-O-protection and a number of acetals and orthoesters were examined for 2'-O-protection. The protection scheme that gave the best results was 5'-O-silyl ether-2'-ACE (5'-O-bis(trimethylsiloxy)cyclododecyloxysilyl ether (DOD)-2'-O-bis(2-acetoxyethoxy)methyl (ACE). This approach uses a modified phosphoramidite synthesis approach in that some different reagents are required that are not routinely used for RNA/DNA synthesis.

Although a lot of research has focused on the synthesis of oligoribonucleotides the main RNA synthesis strategies that are presently being used commercially include 5'-O-DMT-2'-O-t-butyldimethylsilyl (TBDMS), 5'-O-DMT-2'-O-[1(2-fluorophenyl)-4-methoxypiperidin-4-yl] (FPMP), 2'-O-[(triisopropylsilyl)oxy]methyl (2'-O—CH$_2$—O—Si(ipr)$_3$ (TOM), and the 5'-O-silyl ether-2'-ACE (5'-O-bis(trimethylsiloxy)cyclododecyloxysilyl ether (DOD)-2'-O-bis(2-acetoxyethoxy)methyl (ACE). A current list of some of the major companies currently offering RNA products include Pierce Nucleic Acid Technologies, Dharmacon Research Inc., Ameri Biotechnologies Inc., and Integrated DNA Technologies, Inc. One company, Princeton Separations, is marketing an RNA synthesis activator advertised to reduce coupling times especially with TOM and TBDMS chemistries. Such an activator would also be amenable to the present invention.

The primary groups being used for commercial RNA synthesis are:
TBDMS=5'-O-DMT-2'-O-t-butyldimethylsilyl;
TOM=2'-O-[(triisopropylsilyl)oxy]methyl;
DOD/ACE=(5'-O-bis(trimethylsiloxy)cyclododecyloxysilyl ether-2'-O-bis(2-acetoxyethoxy)methyl
FPMP=5'-O-DMT-2'-O-[1(2-fluorophenyl)-4-methoxypiperidin-4-yl].

All of the aforementioned RNA synthesis strategies are amenable to the present invention. Strategies that would be a hybrid of the above e.g. using a 5'-protecting group from one strategy with a 2'-O-protecting from another strategy is also amenable to the present invention.

The preparation of ribonucleotides and oligomeric compounds having at least one ribonucleoside incorporated and all the possible configurations falling in between these two extremes are encompassed by the present invention. The corresponding oligomeric compounds can be hybridized to further oligomeric compounds including oligoribonucleotides having regions of complementarity to form double-stranded (duplexed) oligomeric compounds. Such double stranded oligonucleotide moieties have been shown in the art to modulate target expression and regulate translation as well as RNA processing via an antisense mechanism. Moreover, the double-stranded moieties may be subject to chemical modifications (Fire et al., Nature, 1998, 391, 806-811; Timmons and Fire, Nature 1998, 395, 854; Timmons et al., Gene, 2001, 263, 103-112; Tabara et al., Science, 1998, 282, 430-431; Montgomery et al., Proc. Natl. Acad. Sci. USA, 1998, 95, 15502-15507; Tuschl et al., Genes Dev., 1999, 13, 3191-3197; Elbashir et al., Nature, 2001, 411, 494-498; Elbashir et al., Genes Dev. 2001, 15, 188-200). For example, such double-stranded moieties have been shown to inhibit the target by the classical hybridization of antisense strand of the duplex to the target, thereby triggering enzymatic degradation of the target (Tijsterman et al., Science, 2002, 295, 694-697).

The methods of preparing oligomeric compounds of the present invention can also be applied in the areas of drug discovery and target validation. The present invention comprehends the use of the oligomeric compounds and preferred targets identified herein in drug discovery efforts to elucidate relationships that exist between proteins and a disease state, phenotype, or condition. These methods include detecting or modulating a target peptide comprising contacting a sample, tissue, cell, or organism with the oligomeric compounds of the present invention, measuring the nucleic acid or protein level of the target and/or a related phenotypic or chemical endpoint at some time after treatment, and optionally comparing the measured value to a non-treated sample or sample treated with a further oligomeric compound of the invention. These methods can also be performed in parallel or in combination with other experiments to determine the function of unknown genes for the process of target validation or to determine the validity of a particular gene product as a target for treatment or prevention of a particular disease, condition, or phenotype.

Effect of nucleoside modifications on RNAi activity is evaluated according to existing literature (Elbashir et al., Nature (2001), 411, 494-498; Nishikura et al., Cell (2001), 107, 415-416; and Bass et al., Cell (2000), 101, 235-238).

Targets of the Invention

"Targeting" an antisense oligomeric compound to a particular nucleic acid molecule, in the context of this invention, can be a multistep process. The process usually begins with the identification of a target nucleic acid whose function is to be modulated. This target nucleic acid may be, for example, a cellular gene (or mRNA transcribed from the gene) whose expression is associated with a particular disorder or disease state, or a nucleic acid molecule from an infectious agent.

The targeting process usually also includes determination of at least one target region, segment, or site within the target nucleic acid for the antisense interaction to occur such that the desired effect, e.g., modulation of expression, will result. Within the context of the present invention, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid. The terms region, segment, and site can also be used to describe an oligomeric compound of the invention such as for example a gapped oligomeric compound having 3 separate segments.

Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA transcribed from a gene encoding a nucleic acid target, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions which may be targeted effectively with the antisense oligomeric compounds of the present invention.

The open reading frame (ORF) or "coding region," which is known in the art to refer to the region between the translation initiation codon and the translation termination codon, is also a region which may be targeted effectively. Within the context of the present invention, a preferred region is the intragenic region encompassing the translation initiation or termination codon of the open reading frame (ORF) of a gene.

Other target regions include the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene), and the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. It is also preferred to target the 5' cap region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. Targeting splice sites, i.e., intron-exon junctions or exon-intron junctions, may also be particularly useful in situations where aberrant splicing is implicated in disease, or where an overproduction of a particular splice product is implicated in disease. Aberrant fusion junctions due to rearrangements or deletions are also preferred target sites. mRNA transcripts produced via the process of splicing of two (or more) mRNAs from different gene sources are known as "fusion transcripts". It is also known that introns can be effectively targeted using antisense oligomeric compounds targeted to, for example, DNA or pre-mRNA.

It is also known in the art that alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and exonic sequences. Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Within the context of the invention, the types of variants described herein are also preferred target nucleic acids.

The locations on the target nucleic acid to which the preferred antisense oligomeric compounds hybridize are herein-below referred to as "preferred target segments." As used herein the term "preferred target segment" is defined as at least an 8-nucleobase portion of a target region to which an active antisense oligomeric compound is targeted. While not wishing to be bound by theory, it is presently believed that these target segments represent accessible portions of the target nucleic acid for hybridization.

Exemplary preferred antisense oligomeric compounds include oligomeric compounds that comprise at least the 8 consecutive nucleobases from the 5'-terminus of a targeted nucleic acid e.g. a cellular gene or mRNA transcribed from the gene (the remaining nucleobases being a consecutive stretch of the same oligonucleotide beginning immediately upstream of the 5'-terminus of the antisense compound which is specifically hybridizable to the target nucleic acid and continuing until the oligonucleotide contains from about 8 to about 80 nucleobases). Similarly preferred antisense oligomeric compounds are represented by oligonucleotide sequences that comprise at least the 8 consecutive nucleobases from the 3'-terminus of one of the illustrative preferred antisense compounds (the remaining nucleobases being a consecutive stretch of the same oligonucleotide beginning immediately downstream of the 3'-terminus of the antisense compound which is specifically hybridizable to the target nucleic acid and continuing until the oligonucleotide contains from about 8 to about 80 nucleobases). One having skill in the art armed with the preferred antisense compounds illustrated herein will be able, without undue experimentation, to identify further preferred antisense compounds.

Once one or more target regions, segments or sites have been identified, antisense oligomeric compounds are chosen which are sufficiently complementary to the target, i.e., hybridize sufficiently well and with sufficient specificity, to give the desired effect.

In accordance with one embodiment of the present invention, a series of preferred compositions of nucleic acid duplexes comprising the antisense oligomeric compounds of the present invention and their complements can be designed for a specific target or targets. The ends of the strands may be modified by the addition of one or more natural or modified nucleobases to form an overhang. The sense strand of the duplex is then designed and synthesized as the complement of the antisense strand and may also contain modifications or additions to either terminus. For example, in one embodiment, both strands of the duplex would be complementary over the central nucleobases, each having overhangs at one or both termini.

For example, a duplex comprising an antisense oligomeric compound having the sequence CGAGAGGCGGACGG-GACCG (SEQ ID NO: 16) and having a two-nucleobase overhang of deoxythymidine (dT) would have the following structure:

```
cgagaggcggacgggaccgdTdT    Antisense      (SEQ ID
|||||||||||||||||||        Strand         NO: 17)
dTdTgctctccgcctgccctggc    Complement     (SEQ ID
                           Strand         NO: 18)
```

RNA strands of the duplex can be synthesized by methods disclosed herein or purchased from various RNA synthesis companies such as for example Dharmacon Research Inc., (Lafayette, Colo.). Once synthesized, the complementary strands are annealed. The single strands are aliquoted and diluted to a concentration of 50 uM. Once diluted, 30 uL of each strand is combined with 15 uL of a 5× solution of annealing buffer. The final concentration of the buffer is 100 mM potassium acetate, 30 mM HEPES-KOH pH 7.4, and 2 mM magnesium acetate. The final volume is 75 uL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA compound is 20 uM. This solution can be stored frozen (−20° C.) and freeze-thawed up to 5 times.

Once prepared, the desired synthetic duplexes are evaluated for their ability to modulate target expression. When cells reach 80% confluency, they are treated with synthetic duplexes comprising at least one oligomeric compound of the invention. For cells grown in 96-well plates, wells are washed once with 200 μL OPTI-MEM-1 reduced-serum medium (Gibco BRL) and then treated with 130 μL of OPTI-MEM-1 containing 12 μg/mL LIPOFECTIN (Gibco BRL) and the desired dsRNA compound at a final concentration of 200 nM. After 5 hours of treatment, the medium is replaced with fresh medium. Cells are harvested 16 hours after treatment, at which time RNA is isolated and target reduction measured by RT-PCR.

In a further embodiment, the "preferred target segments" identified herein may be employed in a screen for additional oligomeric compounds that modulate the expression of a target. "Modulators" are those oligomeric compounds that decrease or increase the expression of a nucleic acid molecule encoding a target and which comprise at least an 8-nucleobase portion which is complementary to a preferred target segment. The screening method comprises the steps of contacting a preferred target segment of a nucleic acid molecule encoding a target with one or more candidate modulators, and selecting for one or more candidate modulators which decrease or increase the expression of a nucleic acid molecule encoding a target. Once it is shown that the candidate modulator or modulators are capable of modulating (e.g. either decreasing or increasing) the expression of a nucleic acid molecule encoding a target, the modulator may then be employed in further investigative studies of the function of a target, or for use as a research, diagnostic, or therapeutic agent in accordance with the present invention.

The preferred target segments of the present invention may also be combined with their respective complementary antisense oligomeric compounds of the present invention to form stabilized double-stranded (duplexed) oligonucleotides.

Hybridization

In the context of this invention, "hybridization" occurs when two sequences come together with enough base complementarity to form a double stranded region. The source of the two sequences can be synthetic or native and can occur in a single strand when the strand has regions of self complementarity. In the present invention, the preferred mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds or between an oligomeric compound and a target nucleic acid. For example, adenine and thymine are complementary nucleobases which pair through the formation of hydrogen bonds. Hybridization can occur under varying circumstances.

An antisense oligomeric compound is specifically hybridizable when binding of the compound to the target nucleic acid interferes with the normal function of the target nucleic acid to cause a loss of activity, and there is a sufficient degree of complementarity to avoid non-specific binding of the antisense oligomeric compound to non-target nucleic acid sequences under conditions in which specific binding is desired, i.e., under physiological conditions in the case of in vivo assays or therapeutic treatment, and under conditions in which assays are performed in the case of in vitro assays.

In the present invention the phrase "stringent hybridization conditions" or "stringent conditions" refers to conditions under which an oligomeric compound of the invention will hybridize to its target sequence, but to a minimal number of other sequences. Stringent conditions are sequence-dependent and will vary with different circumstances and in the context of this invention, "stringent conditions" under which oligomeric compounds hybridize to a target sequence are determined by the nature and composition of the oligomeric compounds and the assays in which they are being investigated.

"Complementary," as used herein, refers to the capacity for precise pairing of two nucleobases regardless of where the two are located. For example, if a nucleobase at a certain position of an oligomeric compound is capable of hydrogen bonding with a nucleobase at a certain position of a target nucleic acid, the target nucleic acid being a DNA, RNA, or oligonucleotide molecule, then the position of hydrogen bonding between the oligonucleotide and the target nucleic acid is considered to be a complementary position. The oligomeric compound and the further DNA, RNA, or oligonucleotide molecule are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligonucleotide and a target nucleic acid.

It is understood in the art that the sequence of an antisense oligomeric compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure or hairpin structure). It is preferred that the antisense oligomeric compounds of the present invention comprise at least 70% sequence complementarity to a target region within the target nucleic acid, more preferably that they comprise 90% sequence complementarity and even more preferably comprise 95% sequence complementarity to the target region within the target nucleic acid sequence to which they are targeted. For example, an antisense oligomeric compound in which 18 of 20 nucleobases of the antisense oligomeric compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense oligomeric compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense oligomeric compound with a region of a target nucleic acid can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656).

Screening and Target Validation

In a further embodiment, "preferred target segments" may be employed in a screen for additional oligomeric compounds that modulate the expression of a selected protein. "Modulators" are those oligomeric compounds that decrease or increase the expression of a nucleic acid molecule encoding a protein and which comprise at least an 8-nucleobase portion which is complementary to a preferred target segment. The screening method comprises the steps of contacting a preferred target segment of a nucleic acid molecule encoding a protein with one or more candidate modulators, and selecting for one or more candidate modulators which decrease or increase the expression of a nucleic acid molecule encoding a protein. Once it is shown that the candidate modulator or modulators are capable of modulating (e.g. either decreasing or increasing) the expression of a nucleic acid molecule encoding a peptide, the modulator may then be employed in further investigative studies of the function of the peptide, or for use as a research, diagnostic, or therapeutic agent in accordance with the present invention.

The preferred target segments of the present invention may also be combined with their respective complementary antisense oligomeric compounds of the present invention to form stabilized double-stranded (duplexed) oligonucleotides. Such double stranded oligonucleotide moieties have been shown in the art to modulate target expression and regulate translation as well as RNA processing via an antisense mechanism. Moreover, the double-stranded moieties may be subject to chemical modifications (Fire et al., *Nature*, 1998, 391, 806-811; Timmons and Fire, *Nature* 1998, 395, 854; Timmons et al., *Gene*, 2001, 263, 103-112; Tabara et al., *Science*, 1998, 282, 430-431; Montgomery et al., *Proc. Natl. Acad. Sci. USA*, 1998, 95, 15502-15507; Tuschl et al., *Genes Dev.*, 1999, 13, 3191-3197; Elbashir et al., *Nature*, 2001, 411, 494-498; Elbashir et al., *Genes Dev.* 2001, 15, 188-200). For example, such double-stranded moieties have been shown to inhibit the target by the classical hybridization of antisense strand of the duplex to the target, thereby triggering enzymatic degradation of the target (Tijsterman et al., *Science*, 2002, 295, 694-697).

The compositions comprising oligomeric compounds of the present invention can also be applied in the areas of drug discovery and target validation. The present invention comprehends the use of the oligomeric compounds and preferred targets identified herein in drug discovery efforts to elucidate relationships that exist between proteins and a disease state, phenotype, or condition. These methods include detecting or modulating a target peptide comprising contacting a sample, tissue, cell, or organism with the oligomeric compounds of the present invention, measuring the nucleic acid or protein level of the target and/or a related phenotypic or chemical endpoint at some time after treatment, and optionally comparing the measured value to a non-treated sample or sample treated with a further oligomeric compound of the invention. These methods can also be performed in parallel or in combination with other experiments to determine the function of unknown genes for the process of target validation or to determine the validity of a particular gene product as a target for treatment or prevention of a particular disease, condition, or phenotype.

Effect of nucleoside modifications on RNAi activity is evaluated according to existing literature (Elbashir et al., Nature (2001), 411, 494-498; Nishikura et al., Cell (2001), 107, 415-416; and Bass et al., Cell (2000), 101, 235-238).

Kits, Research Reagents, Diagnostics, and Therapeutics

The compositions of oligomeric compounds of the present invention can be utilized for diagnostics, therapeutics, prophylaxis and as research reagents and kits. Furthermore, antisense oligonucleotides, which are able to inhibit gene expression with exquisite specificity, are often used by those of ordinary skill to elucidate the function of particular genes or to distinguish between functions of various members of a biological pathway.

For use in kits and diagnostics, the compositions of the present invention, either alone or in combination with other oligomeric compounds or therapeutics, can be used as tools in differential and/or combinatorial analyses to elucidate expression patterns of a portion or the entire complement of genes expressed within cells and tissues. As one nonlimiting example, expression patterns within cells or tissues treated with one or more antisense oligomeric compounds are compared to control cells or tissues not treated with antisense oligomeric compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds and or oligomeric compounds that affect expression patterns.

Examples of methods of gene expression analysis known in the art include DNA arrays or microarrays (Brazma and Vilo, *FEBS Lett.*, 2000, 480, 17-24; Celis, et al., *FEBS Lett.*, 2000, 480, 2-16), SAGE (serial analysis of gene expression) (Madden, et al., *Drug Discov. Today*, 2000, 5, 415-425), READS (restriction enzyme amplification of digested cDNAs) (Prashar and Weissman, *Methods Enzymol.*, 1999, 303, 258-72), TOGA (total gene expression analysis) (Sutcliffe, et al., *Proc. Natl. Acad. Sci. U.S.A.*, 2000, 97, 1976-81), protein arrays and proteomics (Celis, et al., *FEBS Lett.*, 2000, 480, 2-16; Jungblut, et al., *Electrophoresis*, 1999, 20, 2100-10), expressed sequence tag (EST) sequencing (Celis, et al., *FEBS Lett.*, 2000, 480, 2-16; Larsson, et al., *J. Biotechnol.*, 2000, 80, 143-57), subtractive RNA fingerprinting (SuRF) (Fuchs, et al., *Anal. Biochem.*, 2000, 286, 91-98; Larson, et al., *Cytometry*, 2000, 41, 203-208), subtractive cloning, differential display (DD) (Jurecic and Belmont, *Curr. Opin. Microbiol.*, 2000, 3, 316-21), comparative genomic hybridization (Carulli, et al., *J. Cell Biochem. Suppl.*, 1998, 31, 286-96), FISH (fluorescent in situ hybridization) techniques (Going and Gusterson, *Eur. J. Cancer*, 1999, 35, 1895-904) and mass spectrometry methods (To, *Comb. Chem. High Throughput Screen*, 2000, 3, 235-41).

The compositions of the invention are useful for research and diagnostics in one sense because the oligomeric compounds of the compositions hybridize to nucleic acids encoding proteins. For example, oligonucleotides that are shown to hybridize with such efficiency and under such conditions as disclosed herein as to be effective protein inhibitors will also be effective primers or probes under conditions favoring gene amplification or detection, respectively. These primers and probes are useful in methods requiring the specific detection of nucleic acid molecules encoding proteins and in the amplification of the nucleic acid molecules for detection or for use in further studies. Hybridization of the antisense oligonucleotides, particularly the primers and probes, of the invention with a nucleic acid can be detected by means known in the art. Such means may include conjugation of an enzyme to the oligonucleotide, radiolabelling of the oligonucleotide or any other suitable detection means. Kits using such detection means for detecting the level of selected proteins in a sample may also be prepared.

The specificity and sensitivity of antisense methodologies is also harnessed by those of skill in the art for therapeutic uses. Antisense oligomeric compounds have been employed as therapeutic moieties in the treatment of disease states in animals, including humans. Antisense oligonucleotide drugs, including ribozymes, have been safely and effectively administered to humans and numerous clinical trials are presently underway. It is thus established that antisense oligomeric compounds can be useful therapeutic modalities that can be configured to be useful in treatment regimes for the treatment of cells, tissues and animals, especially humans.

For therapeutics, an animal, preferably a human, suspected of having a disease or disorder which can be treated by modulating the expression of a selected protein is treated by administering compositions of the invention in accordance with this invention. For example, in one non-limiting embodiment, the methods comprise the step of administering to the animal in need of treatment, a therapeutically effective amount of a protein inhibitor. The protein inhibitors of the present invention effectively inhibit the activity of the protein or inhibit the expression of the protein. In one embodiment, the activity or expression of a protein in an animal is inhibited by about 10%. Preferably, the activity or expression of a protein in an animal is inhibited by about 30%. More preferably, the activity or expression of a protein in an animal is inhibited by 50% or more. For example, the reduction of the expression of a protein may be measured in serum, adipose tissue, liver or any other body fluid, tissue or organ of the animal. Preferably, the cells contained within the fluids, tissues or organs being analyzed contain a nucleic acid molecule encoding a protein and/or the protein itself.

The compositions of the invention can be utilized in pharmaceutical compositions by adding an effective amount to a suitable pharmaceutically acceptable diluent or carrier. Use of the compositions and methods of the invention may also be useful prophylactically.

Formulations

The compositions of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The compositions of the invention encompass any pharmaceutically acceptable salts, esters, or salts of such esters, or any other compound which, upon administration to an animal, including a human, is capable of providing (directly or indirectly) the biologically active metabolite or residue thereof. Accordingly, for example, the disclosure is also drawn to prodrugs and pharmaceutically acceptable salts of the compositions of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the oligomeric compounds of the invention: i.e., salts that retain the desired biological activity of the parent compound and do not impart undesired toxicological effects thereto. For oligonucleotides, preferred examples of pharmaceutically acceptable salts and their uses are further described in U.S. Pat. No. 6,287,860, which is incorporated herein in its entirety.

The present invention also includes pharmaceutical compositions and formulations which include the compositions of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients. Emulsions are typically heterogenous systems of one liquid dispersed in another in the form of droplets usually exceeding 0.1 μm in diameter. Emulsions may contain additional components in addition to the dispersed phases, and the active drug which may be present as a solution in either the aqueous phase, oily phase or itself as a separate phase. Microemulsions are included as an embodiment of the present invention. Emulsions and their uses are well known in the art and are further described in U.S. Pat. No. 6,287,860, which is incorporated herein in its entirety.

Formulations of the present invention include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes which are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860, which is incorporated herein in its entirety.

The pharmaceutical formulations and compositions of the present invention may also include surfactants. The use of surfactants in drug products, formulations and in emulsions is well known in the art. Surfactants and their uses are further described in U.S. Pat. No. 6,287,860, which is incorporated herein in its entirety.

In one embodiment, the present invention employs various penetration enhancers to effect the efficient delivery of nucleic acids, particularly oligonucleotides. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is incorporated herein in its entirety.

One of skill in the art will recognize that formulations are routinely designed according to their intended use, i.e. route of administration.

Preferred formulations for topical administration include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA).

For topical or other administration, oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters, pharmaceutically acceptable salts thereof, and their uses are further described in U.S. Pat. No. 6,287,860, which is incorporated herein in its entirety. Topical formulations are described in detail in U.S. patent application Ser. No. 09/315, 298 filed on May 20, 1999, which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Preferred bile acids/salts and fatty acids and their uses are further described in U.S. Pat. No. 6,287, 860, which is incorporated herein in its entirety. Also preferred are combinations of penetration enhancers, for example, fatty acids/salts in combination with bile acids/ salts. A particularly preferred combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally, in granular form including sprayed dried particles, or complexed to form micro or nanoparticles. Oligonucleotide complexing agents and their uses are further described in U.S. Pat. No. 6,287,860, which is incorporated herein in its entirety. Oral formulations for oligonucleotides and their preparation are described in detail in U.S. application Ser. Nos. 09/108,673 (filed Jul. 1, 1998), 09/315,298 (filed May 20, 1999) and 10/071,822, filed Feb. 8, 2002, each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Certain embodiments of the invention provide pharmaceutical compositions containing one or more of the compositions of the invention and one or more other chemotherapeutic agents which function by a non-antisense mechanism. Examples of such chemotherapeutic agents include but are not limited to cancer chemotherapeutic drugs such as daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethyl-melamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). When used with the compositions of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Combinations of compositions of the invention and other non-antisense drugs are also within the scope of this invention. One or more compositions of the invention can be used in combination with other therapeutic agents to create a cocktail as is currently the strategy for certain viral infections.

In another related embodiment, therapeutically effective combination therapies may comprise the use of two or more compositions of the invention wherein the multiple compositions are targeted to a single or multiple nucleic acid targets. Numerous examples of antisense oligomeric compounds are known in the art. Two or more combined compounds may be used together or sequentially Dosing The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

While the present invention has been described with specificity in accordance with certain of its preferred embodiments, the following examples serve only to illustrate the invention and are not intended to limit the same.

Example 1

Positionally Modified Compositions

The table below shows exemplary positionally modified compositions prepared in accordance with the present invention. In the recited sequences, the first subscripted letter to the right of a nucleobase designation indicates the type of nucleoside modification for that nucleobase, and the second subscripted letter to the right of a nucleobase designation indicates the type of internucleoside linkage at the 3'-position of that nucleobase, using the abbreviations in the Tables below. Target descriptors are: P=PTEN; S=Survivin; E=eIF4E.

The lowercase descriptors for each nucleoside they follow are: a single letter indicates that the internucleoside linkage is phosphodiester with the letters indicating: m=2'-O-methyl; e=2'-O-methoxyethyl (MOE); f=2'-deoxy-2'-fluoro; s=4'-thioribose; l=LNA. When there are two letters the second letter indicates: s=phosphorothioate, o=phosphodiester.

| SEQ ID NO | ISIS Number | Description (Target) | Sequence |
|---|---|---|---|
| 6 | 345838 | antisense(P) | UCCUGGmoAUCCUUmoCACmoCAAmoUmoGm |
| 7 | 338939 | sense | CAUUGGUGAAGGAUCCAGGA |
| 6 | 345839 | antisense(E) | CCUGGmoAmoUCCmoUmoUCACCAAmoUmoGm |
| 7 | 338939 | sense | CAUUGGUGAAGGAUCCAGGA |
| 8 | 345853 | antisense(E) | AUACUCmoAmoGAAmoGmoGUGUCUUmoCmoUm |
| 9 | 338952 | sense | AGAAGACACCUUCUGAGUAU |
| 10 | 352505 | antisense(S) | UUUGAmoAAAmoUGUmoUGAmoUCUmoCmoCm |
| 11 | 343868 | sense(S) | GGAGAUCAACAUUUUCAAA |
| 10 | 352506 | antisense(S) | UUUGAAmoAmoAUGmoUmoUGAUCUmoCmoCm |
| 11 | 343868 | sense(S) | GGAGAUCAACAUUUUCAAA |
| 10 | 352506 | antisense(S) | UUUGAAmoAmoAUGmoUmoUGAUCUmoCmoCm |
| 11 | 346287 | sense(S) | GrsGrsArsGrsArsUrsCrsArsArsCrsArsUrsUrsUrsCrsArsArsA |
| 10 | 352505 | antisense(S) | UUUGAmoAAAmoUGUmoUGAmoUCUmoCmoCm |
| 11 | 346287 | sense(S) | GrsGrsArsGrsArsUrsCrsArsArsCrsArsUrsUrsUrsCrsArsArsA |
| 10 | 352505 | antisense(S) | UUUGAmoAAAmoUGUmoUGAmoUCUmoCmoCm |
| 11 | 352511 | sense | GGmoAGmoAUmoCAmoACmoAUmoUUmoUCmoAAmoA |
| 10 | 352505 | antisense(S) | UUUGAmoAAAmoUGUmoUGAmoUCUmoCmoCm |
| 11 | 352513 | sense | GGmoAmoGmoAmoUmoCmoAmoAmoCmoAmoUmoUmoUmoUmoCmoAmoA |
| 10 | 352506 | antisense(S) | UUUGAAmoAmoAUGmoUmoUGAUCUmoCmoCm |
| 11 | 352511 | sense | GGmoAGmoAUmoCAmoACmoAUmoUUmoUCmoAAmoA |
| 10 | 352505 | antisense(S) | UUUGAmoAAAmoUGUmoUGAmoUCUmoCmoCm |
| 11 | 352514 | sense | GGeoAGeoAUeoCAeoACeoAUeoUUeoUCeoAAeoA |

| SEQ ID NO | ISIS Number | Description (Target) | Sequence |
|---|---|---|---|
| 10 | 352506 | antisense(S) | UUUGAAmoAmoAUGmoUmoUGAUCUmoCmoCm |
| 11 | 352514 | sense | GGeoAGeoAUeoCAeoACeoAUeoUUeoUCeoAAeoA |
| 10 | 352505 | antisense(S) | UUUGAmoAAAmoUGUmoUGAmoUCUmoCmoCm |
| 11 | 352512 | sense | GmoGmoAmoGmoAmoUmoCmoAmoAmo CmoAmoUmoUmoUmoUmoCmoAmoAmoAm |
| 8 | 345853 | antisense(E) | AUACUCmoAmoGAAmoGmoGUGUCUUmo CmoUm |
| 9 | 345857 | sense | AGmoAmoAmoGmoAmoCmoAmoCmoCmo UmoUmoCmoUmoGmoAmoGmoUmoAmoU |
| 10 | 352506 | antisense(S) | UUUGAAmoAmoAUGmoUmoUGAUCUmoCmoCm |
| 11 | 352512 | sense | GmoGmoAmoGmoAmoUmoCmoAmoAmoCmo AmoUmoUmoUmoUmoCmoAmoAmoAm |
| 10 | 352506 | antisense(S) | UUUGAAmoAmoAUGmoUmoUGAUCUmoCmoCm |
| 11 | 352513 | sense | GGmoAmoGmoAmoUmoCmoAmoAmoCmo AmoUmoUmoUmoUmoCmoAmoAmoA |
| 12 | 335225 | antisense(P) | UrsUrsUrsGrsUrsCrsUrsCrsUmsGmsGmsUrsCrsCrs UrsUrsArsCrsUrsU |
| 13 | 308746 | sense | AAGUAAGGACCAGAGACAAA |
| 12 | 335226 | antisense(P) | UrsUrsUrsGrsUrsCmsUmsCmsUrsGrsGrsUrs CrsCrsUrsUrsArsCrsUrsU |
| 13 | 308746 | sense | AAGUAAGGACCAGAGACAAA |
| 12 | 345711 | antisense | UUUGloUCUCUGloGUCCUUACUloU |
| 13 | 308746 | sense(P) | AAGUAAGGACCAGAGACAAA |
| 12 | 345712 | antisense | UUUloGloUCUCUGloGloUCCUUAloCloUU |
| 13 | 308746 | sense(P) | AAGUAAGGACCAGAGACAAA |
| 12 | 347348 | antisense | UloUloUloGUCloUCUloGGUloCCUloUACloUloU1 |
| 13 | 308746 | sense(P) | AAGUAAGGACCAGAGACAAA |
| 12 | 348467 | antisense | UlsUlsUlsGrsUrsClsUrsCrsUlsGrsGrsUlsCrs CrsUlsUrsArsClsUlsU1 |
| 13 | 308746 | sense(P) | AAGUAAGGACCAGAGACAAA |
| 10 | 355715 | antisense | UUUGloAAAAUloGUUGAUCUCloC |
| 11 | 343868 | sense(S) | GGAGAUCAACAUUUCAAA |
| 12 | 331426 | antisense | UrsUrsUrsGrsUrsCrsUrsCrsUlsGlsGlsUrsCrs CrsUrsUrsArsCrsUrsU |
| 13 | 308746 | sense(P) | AAGUAAGGACCAGAGACAAA |
| 12 | 331695 | antisense | UrsUrsUrsGrsUrsCrsUrsCrsUrsGrsGrsUrsCrs CrsUrsUrsArsClsUlsU1 |
| 13 | 308746 | sense(P) | AAGUAAGGACCAGAGACAAA |
| 12 | 332231 | antisense | UrsUrsUrsGrsUrsCrsUrsCrsUrsGrsGrsUrsCrsCrs UrsUrsArsCrsUlsU |
| 13 | 308746 | sense(P) | AAGUAAGGACCAGAGACAAA |
| 10 | 355712 | antisense | UUUGAloAAAloUGUloUGAloUCUmoCmoCm |
| 11 | 343868 | sense(S) | GGAGAUCAACAUUUCAAA |

-continued

| SEQ ID NO | ISIS Number | Description (Target) | Sequence |
|---|---|---|---|
| 10 | 353538 | antisense | UUUsoGAAAAUsoGUUsoGAUCUsoCsoCs |
| 11 | 343868 | sense(S) | GGAGAUCAACAUUUCAAA |
| 12 | 336671 | antisense(P) | UUUGUCUCUGGUCCUUACsoUsoUs |
| 13 | 308746 | sense | AAGUAAGGACCAGAGACAAA |
| 12 | 336674 | antisense(P) | UUUGUCUCUGGUCCUUsoACsoUsoUs |
| 13 | 308746 | sense | AAGUAAGGACCAGAGACAAA |
| 12 | 336675 | antisense(P) | UUUGUCUCUGGUCCUUACUUs |
| 13 | 308746 | sense | AAGUAAGGACCAGAGACAAA |
| 12 | 336672 | antisense(P) | UUUGUCUCUGGUCsoCsoUsoUACUU |
| 13 | 308746 | sense | AAGUAAGGACCAGAGACAAA |
| 12 | 336673 | antisense(P) | UUUGUCUCUGGUsoCsoCsoUUACUU |
| 13 | 308746 | sense | AAGUAAGGACCAGAGACAAA |
| 12 | 336676 | antisense(P) | UUUGUCUsoCsoUsoGGUCCUUACUU |
| 13 | 308746 | sense | AAGUAAGGACCAGAGACAAA |
| 12 | 336678 | antisense(P) | UsoUsoUsoGUCUCUGGUCCUUACUU |
| 13 | 308746 | sense | AAGUAAGGACCAGAGACAAA |
| 10 | 352515 | antisense | UUUGAAAAUGUUGAUmoCmoUmoCmoCm |
| 11 | 343868 | sense(S) | GGAGAUCAACAUUUCAAA |
| 14 | 330919 | antisense | UrsUrsTesGesTesCrsUrsCrsUrsGrsGrsUrsCrsCrs UrsUrsArsCrsUrsU |
| 13 | 308746 | sense(P) | AAGUAAGGACCAGAGACAAA |
| 15 | 330997 | antisense | TesTesTesGrsTrsCrsUrsCrsUrsGrsGrsUrsCrsCrsUrs UrsArsCrsUrsU |
| 13 | 308746 | sense(P) | AAGUAAGGACCAGAGACAAA |
| 12 | 333749 | sntisense | UrsUrsUrsGrsUrsCrsUrsCrsUrsGrsGrsUrsCrsCrsUfs UfsAfsCrsUrsU |
| 13 | 308746 | sense(P) | AAGUAAGGACCAGAGACAAA |
| 12 | 333750 | antisense | UrsUrsUrsGrsUrsCrsUrsCrsUrsGrsGrsUfs CfsCfsUrsUrs ArsCrsUrsU |
| 13 | 308746 | sense(P) | AAGUAAGGACCAGAGACAAA |
| 12 | 333752 | antisense | UrsUrsUrsGrsUrsCfsUfsCfsUrsGrsGrsUrsCrs CrsUrsUrsArsCrsUrsU |
| 13 | 308746 | sense(P) | AAGUAAGGACCAGAGACAAA |
| 12 | 333756 | amtisense | UrsUrsUrsGrsUrsCrsUrsCrsUrsGrsGrsUrsCrsCrsUrs UrsArsCfsUfsUf |
| 13 | 308746 | sense(P) | AAGUAAGGACCAGAGACAAA |
| 12 | 334253 | antisnese | UrsUrsUrsGrsUrsCrsUrsCrsUfsGfsGfsUrsCrsCrs UrsUrsArsCrsUrsU |
| 13 | 308746 | sense(P) | AAGUAAGGACCAGAGACAAA |
| 10 | 353539 | antisense | UsoUsoUsoGAAAAUsoGUUsoGAUCUmoCmoCm |
| 11 | 343868 | sense(S) | GGAGAUCAACAUUUCAAA |

The above constructs were tested in HeLa cells, MH-S cells or U-87 MG cells using a standard assay as shown below. The $IC_{50}$'s were calculated as shown below.

| SEQ ID NO/Construct | Species/Cell Line | Gene | IC50 |
|---|---|---|---|
| 6:7/345838:338939 | Mouse/MH-S | eIF4E | 0.022859 |
| 6:7/345839:338939 | Mouse/MH-S | eIF4E | 0.01205 |
| 8:9/345853:338952 | Mouse/MH-S | eIF4E | 0.075517 |
| 10:11/352505:343868 | Human/HeLA | Survivin | 0.17024 |
| 10:11/352506:343868 | Human/HeLA | Survivin | 0.055386 |
| 10:11/352506:346287 | Human/HeLA | Survivin | 0.11222 |
| 10:11/352505:346287 | Human/HeLA | Survivin | 0.96445 |
| 10:11/352505:352511 | Human/HeLA | Survivin | 0.21527 |
| 10:11/352505:352513 | Human/HeLA | Survivin | 0.12453 |
| 10:11/352506:352511 | Human/HeLA | Survivin | 0.045167 |
| 10:11/352505:352514 | Human/HeLA | Survivin | 0.47593 |
| 10:11/352506:352514 | Human/HeLA | Survivin | 0.11759 |
| 10:11/352506:352514 | Human/HeLA | Survivin | 0.376 |
| 10:11/352505:352514 | Human/U-87 MG | Survivin | 0.261 |
| 10:11/352505:352512 | Human/HeLA | Survivin | 0.075608 |
| 8:9/345853:345857 | Mouse/MH-S | eIF4E | 0.025677 |
| 10:11/352506:352512 | Human/HeLA | Survivin | 0.11093 |
| 10:11/352506:352513 | Human/HeLA | Survivin | 0.24503 |
| 12:13/335225:308746 | Human/HeLA | PTEN | 0.809 |
| 12:13/335226:308746 | Human/HeLA | PTEN | 1.57 |
| 12:13/308746:345711 | Human/HeLA | PTEN | 1.13 |
| 12:13/308746:345712 | Human/HeLA | PTEN | 0.371 |
| 12:13/308746:347348 | Human/HeLA | PTEN | 0.769 |
| 12:13/308746:348467 | Human/HeLA | PTEN | 18.4 |
| 10:11/355715:343868 | Human/HeLA | Survivin | 0.020825 |
| 12:13/331426:308746 | Human/HeLA | PTEN | 0.5627 |
| 12:13/331695:308746 | Human/HeLA | PTEN | 0.27688 |
| 12:13/332231:308746 | Human/HeLA | PTEN | 5.58 |
| 10:11/355712:343868 | Human/HeLA | Survivin | 0.022046 |
| 10:11/353538:343868 | Human/HeLA | Survivin | 0.491 |
| 10:11/353538:343868 | Human/U87-MG | Survivin | 0.46 |
| 12:13/336671:308746 | Human/HeLA | PTEN | 0.273 |
| 12:13/336674:308746 | Human/HeLA | PTEN | 0.363 |
| 12:13/336675:308746 | Human/HeLA | PTEN | 0.131 |
| 12:13/336672:308746 | Human/HeLA | PTEN | 0.428 |
| 12:13/336673:308746 | Human/HeLA | PTEN | 0.122 |
| 12:13/336676:308746 | Human/HeLA | PTEN | 7.08 |
| 12:13/336678:308746 | Human/HeLA | PTEN | 0.144 |
| 10:11/352515:343868 | Human/HeLA | Survivin | 0.031541 |
| 14:13/330919:308746 | Human/HeLA | PTEN | 29.4 |
| 15:13/330997:308746 | Human/HeLA | PTEN | 3.39 |
| 12:13/333749:308746 | Human/HeLA | PTEN | 1.3 |
| 12:13/333750:308746 | Human/HeLA | PTEN | 0.30815 |
| 12:13/333752:308746 | Human/HeLA | PTEN | 1.5416 |
| 12:13/333756:308746 | Human/HeLA | PTEN | 1.0933 |
| 12:13/334253:308746 | Human/HeLA | PTEN | 0.68552 |
| 10:11/353539:343868 | Human/HeLA | Survivin | 0.13216. |

Determination of IC50 Values for Constructs

The $IC_{50}$ values were determined by the following procedure:

Once prepared as described in previous examples, the duplexed oligomeric compounds were evaluated in HeLa cells (American Type Culture Collection, Manassas Va.). Culture methods used for HeLa cells are available from the ATCC and may be found, for example, at http://www.atcc.org. For cells grown in 96-well plates, wells were washed once with 200 μL OPTI-MEM-1 reduced-serum medium (Gibco BRL) and then treated with 130 μL of OPTI-MEM-1 containing 12 μg/mL LIPOFECTIN™ (Gibco BRL) and the dsRNA at the desired concentration. After 5 hours of treatment, the medium was replaced with fresh medium. Cells were harvested 16 hours after dsRNA treatment, at which time RNA was isolated and target reduction measured by RT-PCR as described in previous examples.

The following table describes some preferred positional compositions of the invention. In the listed constructs, the 5'-terminal nucleoside or the sense (upper) strand is hybridized to the 3'-terminal nucleoside of the antisense (lower) strand. Some further preferred positional motifs are shown FIG. 1.

| Compound (sense/antisense) | Construct (sense 5'→3'/antisense) |
|---|---|
| sense RNA<br>4'thio (bold) dispersed antisense | 5'-XXXXXXXXXXXXXXXXXXX-3'<br>3'-XXX$_{17}$XXXXXX$_{12}$XXXX$_9$XXXXXXX$_3$X$_2$X$_1$-5' |
| Sense RNA<br>2'-OMe (italic)/4'-thio (bold) dispersed antisense | 5'-XXXXXXXXXXXXXXXXXXX-3'<br>3'-$X_{19}X_{18}X_{17}$XXXXXXXXXXXXXXXX-5' |
| Sense RNA<br>Chimeric 2'-OMe (italic)/2'-fluoro(bold italic) antisense | 5'-XXXXXXXXXXXXXXXXXXX-3' |
| Alternate<br>MOE(underline)/OH sense<br>Chimeric OMe (italic)/OH antisense | 5'-<u>XXXXXXXXXXXXXXXXXXX</u>-3'<br>3'-$X_{20}X_{19}X_{18}$XXXXXXX$X_{11}X_{10}$XXX$X_7X_6$XXXXX-5' |
| OMe Gapmer Sense/<br>Chimeric OMe (italic)/OH antisense | 5'-XXXXXXXXXXXXXXXXXXX-3'<br>3'-$X_{20}X_{19}X_{18}$XXX$X_{15}$XXX$X_{12}$XXXXXX$X_6$XXXXX-5' |
| Sense RNA<br>Chimeric OMe/OH antisense | 5'-XXXXXXXXXXXXXXXXXXX-3'<br>3'-$XXX_{17}$XXX$X_{14}$XXX$X_{11}$XXX$X_8$XXX$X_5$XXXX-5' |

Example 2

Synthesis of Nucleoside Phosphoramidites

The following compounds, including amidites and their intermediates were prepared as described in U.S. Pat. No. 6,426,220 and published PCT WO 02/36743; 5'-O-Dimethoxytrityl-thymidine intermediate for 5-methyl dC amidite, 5'-O-Dimethoxytrityl-2'-deoxy-5-methylcytidine intermediate for 5-methyl-dC amidite, 5'-O-Dimethoxytrityl-2'-deoxy-N4-benzoyl-5-methylcytidine penultimate intermediate for 5-methyl dC amidite, [5'-O-(4,4'-Dimethoxytriphenylmethyl)-2'-deoxy-$N^4$-benzoyl-5-methylcytidin-3'-O-yl]-2-cyanoethyl-N,N-diisopropylphosphoramidite (5-methyl dC amidite), 2'-Fluorodeoxyadenosine, 2'-Fluorodeoxyguanosine, 2'-Fluorouridine, 2'-Fluorodeoxycytidine, 2'-O-(2-Methoxyethyl) modified amidites, 2'-O-(2-methoxyethyl)-5-methyluridine intermediate, 5'-O-DMT-2'-O-(2-methoxyethyl)-5-methyluridine penultimate intermediate, [5'-O-(4,4'-Dimethoxytriphenylmethyl)-2'-O-(2-methoxyethyl)-5-methyluridin-3'-O-yl]-2-cyanoethyl-N,N-diisopropylphosphoramidite (MOE T amidite), 5'-O-Dimethoxytrityl-2'-O-(2-methoxyethyl)-5-methylcytidine intermediate, 5'-O-dimethoxytrityl-2'-O-(2-methoxyethyl)-$N^4$-benzoyl-5-methyl-cytidine penultimate intermediate, [5'-O-(4,4'-Dimethoxytriphenylmethyl)-2'-O-(2-methoxyethyl)-$N^4$-benzoyl-5-methylcytidin-3'-O-yl]-2-cyanoethyl-N,N-diisopropylphosphoramidite (MOE 5-Me-C amidite), [5'-O-(4,4'-Dimethoxytriphenylmethyl)-2'-O-(2-methoxyethyl)-$N^6$-benzoyladenosin-3'-O-yl]-2-cyanoethyl-N,N-diisopropylphosphoramidite (MOE A amdite), [5'-O-(4,4'-Dimethoxytriphenylmethyl)-2'-O-(2-methoxyethyl)-$N^4$-isobutyrylguanosin-3'-O-yl]-2-cyanoethyl-N,N-diisopropylphosphoramidite (MOE G amidite), 2'-O-(Aminooxyethyl) nucleoside amidites and 2'-O-(dimethylaminooxyethyl) nucleoside amidites, 2'-(Dimethylaminooxyethoxy) nucleoside amidites, 5'-O-tert-Butyldiphenylsilyl-$O^2$-2'-anhydro-5-methyluridine, 5'-O-tert-Butyldiphenylsilyl-2'-O-(2-hydroxyethyl)-5-methyluridine, 2'-O-([2-phthalimidoxy)ethyl]-5'-t-butyldiphenylsilyl-5-methyluridine, 5'-O-tert-butyldiphenylsilyl-2'-O-[(2-formadoximinooxy)ethyl]-5-methyluridine, 5'-O-tert-Butyldiphenylsilyl-2'-O—[N,N dimethylaminooxyethyl]-5-methyluridine, 2'-O-(dimethylaminooxyethyl)-5-methyluridine, 5'-O-DMT-2'-O-(dimethylaminooxyethyl)-5-methyluridine, 5'-O-DMT-2'-O-(2-N,N-dimethylaminooxyethyl)-5-methyluridine-3'-[(2-cyanoethyl)-N,N-diisopropylphosphoramidite], 2'-(Aminooxyethoxy) nucleoside amidites, N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite], 2'-dimethylaminoethoxyethoxy (2'-DMAEOE) nucleoside amidites, 2'-O-[2(2-N,N-dimethylaminoethoxy)ethyl]-5-methyl uridine, 5'-O-dimethoxytrityl-2'-O-[2(2-N,N-dimethylaminoethoxy)-ethyl)]-5-methyl uridine and 5'-O-Dimethoxytrityl-2'-O-[2(2-N,N-dimethylaminoethoxy)-ethyl)]-5-methyl uridine-3'-O-(cyanoethyl-N,N-diisopropyl) phosphoramidite.

Example 3

Oligonucleotide and Oligonucleoside Synthesis

The oligomeric compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

Oligonucleotides: Unsubstituted and substituted phosphodiester (P=O) oligonucleotides are synthesized on an automated DNA synthesizer (Applied Biosystems model 394) using standard phosphoramidite chemistry with oxidation by iodine.

Phosphorothioates (P=S) are synthesized similar to phosphodiester oligonucleotides with the following exceptions: thiation was effected by utilizing a 10% w/v solution of 3,H-1,2-benzodithiole-3-one 1,1-dioxide in acetonitrile for the oxidation of the phosphite linkages. The thiation reaction step time was increased to 180 sec and preceded by the normal capping step. After cleavage from the CPG column and deblocking in concentrated ammonium hydroxide at 55° C. (12-16 hr), the oligonucleotides were recovered by precipitating with >3 volumes of ethanol from a 1 M NH₄OAc solution. Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. No. 5,610,289 or U.S. Pat. No. 5,625,050, herein incorporated by reference.

Phosphoramidite oligonucleotides are prepared as described in U.S. Pat. No. 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Oligonucleosides: Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligo-nucleosides, as well as mixed backbone oligomeric compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 4

RNA Synthesis

In general, RNA synthesis chemistry is based on the selective incorporation of various protecting groups at strategic intermediary reactions. Although one of ordinary skill in the art will understand the use of protecting groups in organic synthesis, a useful class of protecting groups includes silyl ethers. In particular bulky silyl ethers are used to protect the 5'-hydroxyl in combination with an acid-labile orthoester protecting group on the 2'-hydroxyl. This set of protecting groups is then used with standard solid-phase synthesis technology. It is important to lastly remove the acid labile orthoester protecting group after all other synthetic steps. Moreover, the early use of the silyl protecting groups during synthesis ensures facile removal when desired, without undesired deprotection of 2' hydroxyl.

Following this procedure for the sequential protection of the 5'-hydroxyl in combination with protection of the 2'-hydroxyl by protecting groups that are differentially removed and are differentially chemically labile, RNA oligonucleotides were synthesized.

RNA oligonucleotides are synthesized in a stepwise fashion. Each nucleotide is added sequentially (3'- to 5'-direction) to a solid support-bound oligonucleotide. The first nucleoside at the 3'-end of the chain is covalently attached to a solid support. The nucleotide precursor, a ribonucleoside phosphoramidite, and activator are added, coupling the second base onto the 5'-end of the first nucleoside. The support is washed and any unreacted 5'-hydroxyl groups are capped with acetic anhydride to yield 5'-acetyl moieties. The linkage is then oxidized to the more stable and ultimately desired P(V) linkage. At the end of the nucleotide addition cycle, the 5'-silyl group is cleaved with fluoride. The cycle is repeated for each subsequent nucleotide.

Following synthesis, the methyl protecting groups on the phosphates are cleaved in 30 minutes utilizing 1 M disodium-2-carbamoyl-2-cyanoethylene-1,1-dithiolate trihydrate ($S_2Na_2$) in DMF. The deprotection solution is washed from the solid support-bound oligonucleotide using water. The support is then treated with 40% methylamine in water for 10 minutes at 55° C. This releases the RNA oligonucleotides into solution, deprotects the exocyclic amines, and modifies the 2'-groups. The oligonucleotides can be analyzed by anion exchange HPLC at this stage.

The 2'-orthoester groups are the last protecting groups to be removed. The ethylene glycol monoacetate orthoester protecting group developed by Dharmacon Research, Inc. (Lafayette, Colo.), is one example of a useful orthoester protecting group which, has the following important properties. It is stable to the conditions of nucleoside phosphoramidite synthesis and oligonucleotide synthesis. However, after oligonucleotide synthesis the oligonucleotide is treated with methylamine which not only cleaves the oligonucleotide from the solid support but also removes the acetyl groups from the orthoesters. The resulting 2-ethyl-hydroxyl substituents on the orthoester are less electron withdrawing than the acetylated precursor. As a result, the modified orthoester becomes more labile to acid-catalyzed hydrolysis. Specifically, the rate of cleavage is approximately 10 times faster after the acetyl groups are removed. Therefore, this orthoester possesses sufficient stability in order to be compatible with oligonucleotide synthesis and yet, when subsequently modified, permits deprotection to be carried out under relatively mild aqueous conditions compatible with the final RNA oligonucleotide product.

Additionally, methods of RNA synthesis are well known in the art (Scaringe, S. A. Ph.D. Thesis, University of Colorado, 1996; Scaringe, S. A., et al., *J. Am. Chem. Soc.*, 1998, 120, 11820-11821; Matteucci, M. D. and Caruthers, M. H. *J. Am. Chem. Soc.*, 1981, 103, 3185-3191; Beaucage, S. L. and Caruthers, M. H. *Tetrahedron Lett.*, 1981, 22, 1859-1862; Dahl, B. J., et al., *Acta Chem. Scand*, 1990, 44, 639-641; Reddy, M. P., et al., *Tetrahedron Lett.*, 1994, 25, 4311-4314; Wincott, F. et al., *Nucleic Acids Res.*, 1995, 23, 2677-2684; Griffin, B. E., et al., *Tetrahedron*, 1967, 23, 2301-2313; Griffin, B. E., et al., *Tetrahedron*, 1967, 23, 2315-2331).

RNA antisense oligomeric compounds (RNA oligonucleotides) of the present invention can be synthesized by the methods herein or purchased from Dharmacon Research, Inc (Lafayette, Colo.). Once synthesized, complementary RNA antisense oligomeric compounds can then be annealed by methods known in the art to form double stranded (duplexed) antisense oligomeric compounds. For example, duplexes can be formed by combining 30 µl of each of the complementary strands of RNA oligonucleotides (50 uM RNA oligonucleotide solution) and 15 µl of 5× annealing buffer (100 mM potassium acetate, 30 mM HEPES-KOH pH 7.4, 2 mM magnesium acetate) followed by heating for 1 minute at 90° C., then 1 hour at 37° C. The resulting duplexed antisense oligomeric compounds can be used in kits, assays, screens, or other methods to investigate the role of a target nucleic acid.

Example 5

Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]-[2'-deoxy]-[2'-O-Me] Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 394, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by incorporating coupling steps with increased reaction times for the 5'-dimethoxytrityl-2'-O-methyl-3'-O-phosphoramidite. The fully protected oligonucleotide is cleaved from the support and deprotected in concentrated ammonia ($NH_4OH$) for 12-16 hr at 55° C. The deprotected oligo is then recovered by an appropriate method precipitation, column chromatography, volume reduced in vacuo and analyzed spectrophotometrically for yield and for purity by capillary electrophoresis and by mass spectrometry.

[2'-O-(2-Methoxyethyl)]-[2'-deoxy]-[2'-O-(Methoxyethyl)] Chimeric Phosphorothioate Oligonucleotides

[2'-O-(2-methoxyethyl)]-[2'-deoxy]-[-2'-O-(methoxyethyl)] chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]-[2'-deoxy Phosphorothioate]-[2'-O-(2-Methoxyethyl) Phosphodiester] Chimeric Oligonucleotides

[2'-O-(2-methoxyethyl phosphodiester]-[2'-deoxy phosphorothioate]-[2'-O-(methoxyethyl)phosphodiester] chimeric oligonucleotides are prepared as per the above procedure for the 2'-O-methyl chimeric oligonucleotide with the substitution of 2'-O-(methoxyethyl) amidites for the 2'-O-methyl amidites, oxidation with iodine to generate the phosphodiester linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 6

Design and Screening of Duplexed Antisense Oligomeric Compounds Directed to a Selected Target In accordance with the present invention, a series of nucleic acid duplexes comprising the antisense oligomeric compounds of the present invention and their complements can be designed to target a target. The ends of the strands may be modified by the addition of one or more natural or modified nucleobases to form an overhang. The sense strand of the dsRNA is then designed and synthesized as the complement of the antisense strand and may also contain modifications or additions to either terminus. For example, in one embodiment, both strands of the dsRNA duplex would be complementary over the central nucleobases, each having overhangs at one or both termini.

For example, a duplex comprising an antisense strand having the sequence CGAGAGGCGGACGGGACCG (SEQ ID NO: 16) and having a two-nucleobase overhang of deoxythymidine (dT) would have the following structure:

```
cgagaggcggacgggaccgTT  Antisense    (SEQ ID NO: 17)
|||||||||||||||||||    Strand
TTgctctccgcctgccctggc  Complement   (SEQ ID NO: 18)
                       Strand
```

RNA strands of the duplex can be synthesized by methods disclosed herein or purchased from Dharmacon Research Inc., (Lafayette, Colo.). Once synthesized, the complementary strands are annealed. The single strands are aliquoted and diluted to a concentration of 50 uM. Once diluted, 30 uL of each strand is combined with 15 uL of a 5× solution of annealing buffer. The final concentration of said buffer is 100 mM potassium acetate, 30 mM HEPES-KOH pH 7.4, and 2 mM magnesium acetate. The final volume is 75 uL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA duplex is 20 uM. This solution can be stored frozen (−20° C.) and freeze-thawed up to 5 times.

Once prepared, the duplexed antisense oligomeric compounds are evaluated for their ability to modulate a target expression.

When cells reached 80% confluency, they are treated with duplexed antisense oligomeric compounds of the invention. For cells grown in 96-well plates, wells are washed once with 200 μL OPTI-MEM-1 reduced-serum medium (Gibco BRL) and then treated with 130 μL of OPTI-MEM-1 containing 12 μg/mL LIPOFECTIN (Gibco BRL) and the desired duplex antisense oligomeric compound at a final concentration of 200 nM. After 5 hours of treatment, the medium is replaced with fresh medium. Cells are harvested 16 hours after treatment, at which time RNA is isolated and target reduction measured by RT-PCR.

Example 7

Oligonucleotide Isolation

After cleavage from the controlled pore glass solid support and deblocking in concentrated ammonium hydroxide at 55° C. for 12-16 hours, the oligonucleotides or oligonucleosides are recovered by precipitation out of 1 M $NH_4OAc$ with >3 volumes of ethanol. Synthesized oligonucleotides were analyzed by electrospray mass spectroscopy (molecular weight determination) and by capillary gel electrophoresis and judged to be at least 70% full length material. The relative amounts of phosphorothioate and phosphodiester linkages obtained in the synthesis was determined by the ratio of correct molecular weight relative to the −16 amu product (+/−32+−48). For some studies oligonucleotides were purified by HPLC, as described by Chiang et al., *J. Biol. Chem.* 1991, 266, 18162-18171. Results obtained with HPLC-purified material were similar to those obtained with non-HPLC purified material.

Example 8

Oligonucleotide Synthesis

96 Well Plate Format

Oligonucleotides were synthesized via solid phase P(III) phosphoramidite chemistry on an automated synthesizer capable of assembling 96 sequences simultaneously in a 96-well format. Phosphodiester internucleotide linkages were afforded by oxidation with aqueous iodine. Phosphorothioate internucleotide linkages were generated by sulfurization utilizing 3,H-1,2benzodithiole-3-one 1,1dioxide (Beaucage Reagent) in anhydrous acetonitrile. Standard base-protected beta-cyanoethyl-diiso-propyl phosphoramidites were purchased from commercial vendors (e.g. PE-Applied Biosystems, Foster City, Calif., or Pharmacia, Piscataway, N.J.). Non-standard nucleosides are synthesized as per standard or patented methods. They are utilized as base protected beta-cyanoethyldiisopropyl phosphoramidites.

Oligonucleotides were cleaved from support and deprotected with concentrated $NH_4OH$ at elevated temperature (55-60° C.) for 12-16 hours and the released product then dried in vacuo. The dried product was then re-suspended in sterile water to afford a master plate from which all analytical and test plate samples are then diluted utilizing robotic pipettors.

Example 9

Oligonucleotide Analysis Using 96-Well Plate Format

The concentration of oligonucleotide in each well was assessed by dilution of samples and UV absorption spectroscopy. The full-length integrity of the individual products was evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition was confirmed by mass analysis of the oligomeric compounds utilizing electrospray-mass spectroscopy. All assay test plates were diluted from the master plate using single and multi-channel robotic pipettors. Plates were judged to be acceptable if at least 85% of the oligomeric compounds on the plate were at least 85% full length.

Example 10

Cell Culture and Oligonucleotide Treatment

The effect of oligomeric compounds on target nucleic acid expression can be tested in any of a variety of cell types provided that the target nucleic acid is present at measurable levels. This can be routinely determined using, for example, PCR or Northern blot analysis. The following cell types are provided for illustrative purposes, but other cell types can be routinely used, provided that the target is expressed in the cell type chosen. This can be readily determined by methods routine in the art, for example Northern blot analysis, ribonuclease protection assays, or RT-PCR.

T-24 Cells:

The human transitional cell bladder carcinoma cell line T-24 was obtained from the American Type Culture Collection (ATCC) (Manassas, Va.). T-24 cells were routinely cultured in complete McCoy's 5A basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence. Cells were seeded into 96-well plates (Falcon-Primaria #353872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells:

The human lung carcinoma cell line A549 was obtained from the American Type Culture Collection (ATCC) (Manassas, Va.). A549 cells were routinely cultured in DMEM basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence.

NHDF Cells:

Human neonatal dermal fibroblast (NHDF) were obtained from the Clonetics Corporation (Walkersville, Md.). NHDFs were routinely maintained in Fibroblast Growth Medium (Clonetics Corporation, Walkersville, Md.) supplemented as recommended by the supplier. Cells were maintained for up to 10 passages as recommended by the supplier.

HEK Cells:

Human embryonic keratinocytes (HEK) were obtained from the Clonetics Corporation (Walkersville, Md.). HEKs were routinely maintained in Keratinocyte Growth Medium (Clonetics Corporation, Walkersville, Md.) formulated as recommended by the supplier. Cells were routinely maintained for up to 10 passages as recommended by the supplier.

Treatment with Oligomeric Compounds:

When cells reached 65-75% confluency, they were treated with oligonucleotide. For cells grown in 96-well plates, wells were washed once with 100 μL OPTI-MEM™-1 reduced-serum medium (Invitrogen Corporation, Carlsbad, Calif.) and then treated with 130 μL of OPTI-MEM™-1 containing 3.75 μg/mL LIPOFECTIN™ (Invitrogen Corporation, Carlsbad, Calif.) and the desired concentration of oligonucleotide. Cells are treated and data are obtained in triplicate. After 4-7 hours of treatment at 37° C., the medium was replaced with fresh medium. Cells were harvested 16-24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is selected from either ISIS 13920 (TCCGTCATCGCTCCT-CAGGG, SEQ ID NO: 3) which is targeted to human H-ras, or ISIS 18078, (GTGCGCGCGAGCCCGAAATC, SEQ ID NO: 4) which is targeted to human Jun-N-terminal kinase-2 (JNK2). Both controls are 2'-O-methoxyethyl gapmers (2'-O-methoxyethyls shown in bold) with a phosphorothioate backbone. For mouse or rat cells the positive control oligonucleotide is ISIS 15770, ATGCATTCTGCCCCCAAGGA, SEQ ID NO: 5, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-H-ras (for ISIS 13920), JNK2 (for ISIS 18078) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of c-H-ras, JNK2 or c-raf mRNA is then utilized as the oligonucleotide screening concentration in subsequent experiments for that cell line. If 60% inhibition is not achieved, that particular cell line is deemed as unsuitable for oligonucleotide transfection experiments. The concentrations of antisense oligonucleotides used herein are from 50 nM to 300 nM.

Example 11

Analysis of Oligonucleotide Inhibition of a Target Expression

Antisense modulation of a target expression can be assayed in a variety of ways known in the art. For example, a target mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+ mRNA. The preferred method of RNA analysis of the present invention is the use of total cellular RNA as described in other examples herein. Methods of RNA isolation are well known in the art. Northern blot analysis is also routine in the art. Real-time quantitative (PCR) can be conveniently accomplished using the commercially available ABI PRISM™ 7600, 7700, or 7900 Sequence Detection System, available from PE-Applied Biosystems, Foster City, Calif. and used according to manufacturer's instructions.

Protein levels of a target can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art.

Example 12

Design of Phenotypic Assays and In Vivo Studies for the Use of a Target Inhibitors Phenotypic Assays Once a target inhibitors have been identified by the methods disclosed herein, the oligomeric compounds are further investigated in one or more phenotypic assays, each having measurable endpoints predictive of efficacy in the treatment of a particular disease state or condition.

Phenotypic assays, kits and reagents for their use are well known to those skilled in the art and are herein used to investigate the role and/or association of a target in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with a target inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Analysis of the genotype of the cell (measurement of the expression of one or more of the genes of the cell) after treatment is also used as an indicator of the efficacy or potency of the a target inhibitors. Hallmark genes, or those genes suspected to be associated with a specific disease state, condition, or phenotype, are measured in both treated and untreated cells.

In Vivo Studies

The individual subjects of the in vivo studies described herein are warm-blooded vertebrate animals, which includes humans.

The clinical trial is subjected to rigorous controls to ensure that individuals are not unnecessarily put at risk and that they are fully informed about their role in the study.

To account for the psychological effects of receiving treatments, volunteers are randomly given placebo or a target inhibitor. Furthermore, to prevent the doctors from being biased in treatments, they are not informed as to whether the medication they are administering is a target inhibitor or a placebo. Using this randomization approach, each volunteer has the same chance of being given either the new treatment or the placebo.

Volunteers receive either the a target inhibitor or placebo for eight week period with biological parameters associated with the indicated disease state or condition being measured at the beginning (baseline measurements before any treatment), end (after the final treatment), and at regular intervals during the study period. Such measurements include the levels of nucleic acid molecules encoding a target or a target protein levels in body fluids, tissues or organs compared to pre-treatment levels. Other measurements include, but are not limited to, indices of the disease state or condition being treated, body weight, blood pressure, serum titers of pharmacologic indicators of disease or toxicity as well as ADME (absorption, distribution, metabolism and excretion) measurements. Information recorded for each patient includes age (years), gender, height (cm), family history of disease state or condition (yes/no), motivation rating (some/moderate/great) and number and type of previous treatment regimens for the indicated disease or condition.

Volunteers taking part in this study are healthy adults (age 18 to 65 years) and roughly an equal number of males and females participate in the study. Volunteers with certain characteristics are equally distributed for placebo and a target inhibitor treatment. In general, the volunteers treated with placebo have little or no response to treatment, whereas the volunteers treated with the a target inhibitor show positive trends in their disease state or condition index at the conclusion of the study.

Example 13

RNA Isolation

Poly(A)+ mRNA Isolation

Poly(A)+ mRNA was isolated according to Miura et al., (*Clin. Chem.*, 1996, 42, 1758-1764). Other methods for poly (A)+ mRNA isolation are routine in the art. Briefly, for cells grown on 96-well plates, growth medium was removed from the cells and each well was washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 µL of lysate was transferred to Oligo d(T) coated 96-well plates (AGCT Inc., Irvine Calif.). Plates were incubated for 60 minutes at room temperature, washed 3 times with 200 µL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 µL of elution buffer (5 mM Tris-HCl pH 7.6), preheated to 70° C., was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Total RNA Isolation

Total RNA was isolated using an RNEASY 96™ kit and buffers purchased from Qiagen Inc. (Valencia, Calif.) following the manufacturer's recommended procedures. Briefly, for cells grown on 96-well plates, growth medium was removed from the cells and each well was washed with 200 µL cold PBS. 150 µL Buffer RLT was added to each well and the plate vigorously agitated for 20 seconds. 150 µL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 1 minute. 500 µL of Buffer RW1 was added to each well of the RNEASY 96™ plate and incubated for 15 minutes and the vacuum was again applied for 1 minute. An additional 500 µL of Buffer RW1 was added to each well of the RNEASY 96™ plate and the vacuum was applied for 2 minutes. 1 mL of Buffer RPE was then added to each well of the RNEASY 96™ plate and the vacuum applied for a period of 90 seconds. The Buffer RPE wash was then repeated and the vacuum was applied for an additional 3 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 140 µL of RNAse free water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 14

Real-Time Quantitative PCR Analysis of a Target mRNA Levels

Quantitation of a target mRNA levels was accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from Invitrogen Corporation, (Carlsbad, Calif.). RT-PCR reactions were carried out by adding 20 µL PCR cocktail (2.5×PCR buffer minus $MgCl_2$, 6.6 mM $MgCl_2$, 375 µM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5× ROX dye) to 96-well plates containing 30 µL total RNA solution (20-200 ng). The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH, a gene whose expression is constant, or by quantifying total RNA using RiboGreen™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent (Molecular Probes, Inc. Eugene, Oreg.). Methods of RNA quantification by RiboGreen™ are taught in Jones, L. J., et al, (Analytical Biochemistry, 1998, 265, 368-374).

In this assay, 170 µL of RiboGreen™ working reagent (RiboGreen™ reagent diluted 1:350 in 10 mM Tris-HCl, 1 mM EDTA, pH 7.5) is pipetted into a 96-well plate containing 30 µL purified, cellular RNA. The plate is read in a CytoFluor 4000 (PE Applied Biosystems) with excitation at 485 nm and emission at 530 nm.

Probes and are designed to hybridize to a human a target sequence, using published sequence information.

Example 15

Northern Blot Analysis of a Target mRNA Levels

Eighteen hours after antisense treatment, cell monolayers were washed twice with cold PBS and lysed in 1 mL RNAZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 (Stratagene, Inc, La Jolla, Calif.) and then probed using QUICKHYB™ hybridization solution (Stratagene, La Jolla, Calif.) using manufacturer's recommendations for stringent conditions.

To detect human a target, a human a target specific primer probe set is prepared by PCR To normalize for variations in loading and transfer efficiency membranes are stripped and probed for human glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 16

Inhibition of Human a Target Expression by Oligomeric Compounds

In accordance with the present invention, a series of oligomeric compounds are designed to target different regions of the human target RNA. The oligomeric compounds are analyzed for their effect on human target mRNA levels by quantitative real-time PCR as described in other examples herein. Data are averages from three experiments. The target regions to which these preferred sequences are complementary are herein referred to as "preferred target segments" and are therefore preferred for targeting by oligomeric compounds of the present invention. The sequences represent the reverse complement of the preferred oligomeric compounds.

As these "preferred target segments" have been found by experimentation to be open to, and accessible for, hybridization with the oligomeric compounds of the present invention, one of skill in the art will recognize or be able to ascertain, using no more than routine experimentation, further embodiments of the invention that encompass other oligomeric compounds that specifically hybridize to these preferred target segments and consequently inhibit the expression of a target.

According to the present invention, oligomeric compounds include antisense oligomeric compounds, antisense oligonucleotides, ribozymes, external guide sequence (EGS) oligonucleotides, alternate splicers, primers, probes, and other short oligomeric compounds which hybridize to at least a portion of the target nucleic acid.

Example 17

Western Blot Analysis of Target Protein Levels

Western blot analysis (immunoblot analysis) is carried out using standard methods. Cells are harvested 16-20 h after oligonucleotide treatment, washed once with PBS, suspended in Laemmli buffer (100 ul/well), boiled for 5 minutes and loaded on a 16% SDS-PAGE gel. Gels are run for 1.5 hours at 150 V, and transferred to membrane for western blotting. Appropriate primary antibody directed to a target is used, with a radiolabeled or fluorescently labeled secondary antibody directed against the primary antibody species. Bands are visualized using a PHOSPHORIMAGER™ (Molecular Dynamics, Sunnyvale Calif.).

Example 18

Representative Cell Lines

MCF-7 Cells

The human breast carcinoma cell line MCF-7 is obtained from the American Type Culture Collection (Manassas, Va.). These cells contain a wild-type p53 gene. MCF-7 cells are routinely cultured in DMEM low glucose (Gibco/Life Technologies, Gaithersburg, Md.) supplemented with 10% fetal calf serum (Gibco/Life Technologies, Gaithersburg, Md.). Cells are routinely passaged by trypsinization and dilution when they reach 90% confluence. Cells are seeded into 96-well plates (Falcon-Primaria #3872) at a density of 7000 cells/well for treatment with the oligomeric compounds of the invention.

HepB3 Cells

The human hepatoma cell line HepB3 (Hep3B2.1-7) is obtained from the American Type Culture Collection (ATCC-ATCC Catalog #HB-8064) (Manassas, Va.). This cell line was initially derived from a hepatocellular carcinoma of an 8-yr-old black male. The cells are epithelial in morphology and are tumorigenic in nude mice. HepB3 cells are routinely cultured in Minimum Essential Medium (MEM) with Earle's Balanced Salt Solution, 2 mM L-glutamine, 1.5 g/L sodium bicarbonate, 0.1 mM nonessential amino acids, 1.0 mM sodium pyruvate (ATCC #20-2003, Manassas, Va.) and with 10% heat-inactivated fetal bovine serum (Gibco/Life Technologies, Gaithersburg, Md.). Cells are routinely passaged by trypsinization and dilution when they reach 90% confluence.

T-24 Cells

The transitional cell bladder carcinoma cell line T-24 is obtained from the American Type Culture Collection (ATCC) (Manassas, Va.). T-24 cells are routinely cultured in complete McCoy's 5A basal media (Gibco/Life Technologies, Gaithersburg, Md.) supplemented with 10% fetal calf serum (Gibco/Life Technologies, Gaithersburg, Md.), penicillin 100 units per mL, and streptomycin 100 µg/mL (Gibco/Life Technologies, Gaithersburg, Md.). Cells are routinely passaged by trypsinization and dilution when they reach 90% confluence. Cells are seeded into 96-well plates (Falcon-Primaria #3872) at a density of 7000 cells/well for treatment with the compound of the invention.

A549 Cells

The human lung carcinoma cell line A549 is obtained from the American Type Culture Collection (ATCC) (Manassas, Va.). A549 cells are routinely cultured in DMEM basal media (Gibco/Life Technologies, Gaithersburg, Md.) supplemented with 10% fetal calf serum (Gibco/Life Technologies, Gaithersburg, Md.), penicillin 100 units per mL, and streptomycin 100 µg/mL (Gibco/Life Technologies, Gaithersburg, Md.). Cells are routinely passaged by trysinization and dilution when they reach 90% confluence. Cells are seeded into 96-well plates (Falcon-Primaria #3872) at a density of 7000 cells/well for treatment with the compound of the invention.

Primary Mouse Hepatocytes

Primary mouse hepatocytes are prepared from CD-1 mice purchased from Charles River Labs. Primary mouse hepatocytes are routinely cultured in Hepatocyte Attachment Media (Invitrogen Life Technologies, Carlsbad, Calif.) supplemented with 10% Fetal Bovine Serum (Invitrogen Life Technologies, Carlsbad, Calif.), 250 nM dexamethasone (Sigma-Aldrich Corporation, St. Louis, Mo.), 10 nM bovine insulin (Sigma-Aldrich Corporation, St. Louis, Mo.). Cells are seeded into 96-well plates (Falcon-Primaria #353872, BD Biosciences, Bedford, Mass.) at a density of 4000-6000 cells/well for treatment with the oligomeric compounds of the invention.

Example 19

Liposome-Mediated Treatment with Oligomeric Compounds of the Invention

When cells reach the desired confluency, they can be treated with the oligomeric compounds of the invention by liposome-mediated transfection. For cells grown in 96-well plates, wells are washed once with 200 μL OPTI-MEM™-1 reduced-serum medium (Gibco BRL) and then treated with 100 μL of OPTI-MEM™-1 containing 2.5 μg/mL LIPOFECTIN™ (Gibco BRL) and the oligomeric compounds of the invention at the desired final concentration. After 4 hours of treatment, the medium is replaced with fresh medium. Cells are harvested 16 hours after treatment with the oligomeric compounds of the invention for target mRNA expression analysis by real-time PCR.

Example 20

Electroporation-Mediated Treatment with Oligomeric Compounds of the Invention

When the cells reach the desired confluency, they can be treated with the oligomeric compounds of the invention by electorporation. Cells are electroporated in the presence of the desired concentration of an oligomeric compound of the invention in 1 mm cuvettes at a density of $1 \times 10^7$ cells/mL, a voltage of 75V and a pulse length of 6 ms. Following the delivery of the electrical pulse, cells are replated for 16 to 24 hours. Cells are then harvested for target mRNA expression analysis by real-time PCR.

Example 21

Apoptosis Assay

Caspase-3 activity is evaluated with an fluorometric HTS Caspase-3 assay (Oncogene Research Products, San Diego, Calif.) that detects cleavage after aspartate residues in the peptide sequence (DEVD). The DEVD substrate is labeled with a fluorescent molecule, which exhibits a blue to green shift in fluorescence upon cleavage. Active caspase-3 in treated cells is measured by this assay according to the manufacturer's instructions. Following treatment with the oligomeric compounds of the invention, 50 μL of assay buffer is added to each well, followed by addition 20 μL of the caspase-3 fluorescent substrate conjugate. Data are obtained in triplicate. Fluorescence in wells is immediately detected (excitation/emission 400/505 nm) using a fluorescent plate reader (SpectraMAX GeminiXS, Molecular Devices, Sunnyvale, Calif.). The plate is covered and incubated at 37° C. for an additional three hours, after which the fluorescence is again measured (excitation/emission 400/505 nm). The value at time zero is subtracted from the measurement obtained at 3 hours. The measurement obtained from the untreated control cells is designated as 100% activity.

Example 22

Cell Proliferation and Viability Assay

Cell viability and proliferation are measured using the CyQuant Cell Proliferation Assay Kit (Molecular Probes, Eugene, Oreg.) utilizing the CyQuant GR green fluorescent dye which exhibits strong fluorescence enhancement when bound to cellular nucleic acids. The assay is performed according to the manufacturer's instructions. After the treatment with one or more oligomeric compounds of the invention, the microplate is gently inverted to remove the medium from the wells, which are each washed once with 200 μL of phosphate-buffered saline. Plates are frozen at −70° C. and then thawed. A volume of 200 μL of the CyQUANT GR dye/cell-lysis buffer is added to each well. The microplate is incubated for 5 minutes at room temperature, protected from light. Data are obtained in triplicate. Fluorescence in wells is immediately detected (excitation/emission 480/520 nm) using a fluorescent plate reader (SpectraMAX GeminiXS, Molecular Devices, Sunnyvale, Calif.). The measurement obtained from the untreated control cells is designated as 100% activity.

Example 23

Leptin-Deficient Mice

A Model of Obesity and Diabetes (ob/ob Mice)

Leptin is a hormone produced by fat that regulates appetite. Deficiencies in this hormone in both humans and non-human animals leads to obesity. ob/ob mice have a mutation in the leptin gene which results in obesity and hyperglycemia. As such, these mice are a useful model for the investigation of obesity and diabetes and treatments designed to treat these conditions. ob/ob mice have higher circulating levels of insulin and are less hyperglycemic than db/db mice, which harbor a mutation in the leptin receptor. In accordance with the present invention, the oligomeric compounds of the invention are tested in the ob/ob model of obesity and diabetes.

Seven-week old male C57B1/6J-Lepr ob/ob mice (Jackson Laboratory, Bar Harbor, Me.) are fed a diet with a fat content of 10-15% and are subcutaneously injected with the oligomeric compounds of the invention or a control compound at a dose of 25 mg/kg two times per week for 4 weeks. Saline-injected animals, leptin wildtype littermates (i.e. lean littermates) and ob/ob mice fed a standard rodent diet serve as controls. After the treatment period, mice are sacrificed and target levels are evaluated in liver, brown adipose tissue (BAT) and white adipose tissue (WAT). RNA isolation and target mRNA expression level quantitation are performed as described by other examples herein.

To assess the physiological effects resulting from inhibition of target mRNA, the ob/ob mice are further evaluated at the end of the treatment period for serum lipids, serum free fatty acids, serum cholesterol (CHOL), liver triglycerides, fat tissue triglycerides and liver enzyme levels. Hepatic steatosis, or clearing of lipids from the liver, is assessed by measuring the liver triglyceride content. Hepatic steatosis is assessed by routine histological analysis of frozen liver tissue sections stained with oil red O stain, which is commonly used to visualize lipid deposits, and counterstained with hematoxylin and eosin, to visualize nuclei and cytoplasm, respectively.

The effects of target inhibition on glucose and insulin metabolism are evaluated in the ob/ob mice treated with the oligomeric compounds of the invention. Plasma glucose is measured at the start of the treatment and after 2 weeks and 4 weeks of treatment. Plasma insulin is similarly measured at the beginning of the treatment, and following at 2 weeks and at 4 weeks of treatment. Glucose and insulin tolerance tests are also administered in fed and fasted mice. Mice receive intraperitoneal injections of either glucose or insulin, and the blood glucose and insulin levels are measured before the insulin or glucose challenge and at 15, 20 or 30 minute intervals for up to 3 hours.

To assess the metabolic rate of ob/ob mice treated with the oligomeric compounds of the invention, the respiratory quotient and oxygen consumption of the mice are also measured.

The ob/ob mice that received treatment are further evaluated at the end of the treatment period for the effects of target inhibition on the expression genes that participate in lipid metabolism, cholesterol biosynthesis, fatty acid oxidation, fatty acid storage, gluconeogenesis and glucose metabolism. These genes include, but are not limited to, HMG-CoA reductase, acetyl-CoA carboxylase 1 and acetyl-CoA carboxylase 2, carnitine palmitoyltransferase I and glycogen phosphorylase, glucose-6-phosphatase and phosphoenolpyruvate carboxykinase 1, lipoprotein lipase and hormone sensitive lipase. mRNA levels in liver and white and brown adipose tissue are quantitated by real-time PCR as described in other examples herein, employing primer-probe sets that are generated using published sequences of each gene of interest.

Example 24

Leptin Receptor-Deficient Mice

A Model of Obesity and Diabetes (db/db Mice)

Leptin is a hormone produced by fat that regulates appetite. Deficiencies in this hormone in both humans and non-human animals leads to obesity. db/db mice have a mutation in the leptin receptor gene which results in obesity and hyperglycemia. As such, these mice are a useful model for the investigation of obesity and diabetes and treatments designed to treat these conditions. db/db mice, which have lower circulating levels of insulin and are more hyperglycemic than ob/ob mice which harbor a mutation in the leptin gene, are often used as a rodent model of type 2 diabetes. In accordance with the present invention, oligomeric compounds of the present invention are tested in the db/db model of obesity and diabetes.

Seven-week old male C57Bl/6J-Lepr db/db mice (Jackson Laboratory, Bar Harbor, Me.) are fed a diet with a fat content of 15-20% and are subcutaneously injected with one or more of the oligomeric compounds of the invention or a control compound at a dose of 25 mg/kg two times per week for 4 weeks. Saline-injected animals, leptin receptor wildtype littermates (i.e. lean littermates) and db/db mice fed a standard rodent diet serve as controls. After the treatment period, mice are sacrificed and target levels are evaluated in liver, brown adipose tissue (BAT) and white adipose tissue (WAT). RNA isolation and target mRNA expression level quantitation are performed as described by other examples herein.

After the treatment period, mice are sacrificed and target levels are evaluated in liver, brown adipose tissue (BAT) and white adipose tissue (WAT). RNA isolation and target mRNA expression level quantitation are performed as described by other examples herein.

To assess the physiological effects resulting from inhibition of target mRNA, the db/db mice that receive treatment are further evaluated at the end of the treatment period for serum lipids, serum free fatty acids, serum cholesterol (CHOL), liver triglycerides, fat tissue triglycerides and liver enzyme levels. Hepatic steatosis, or clearing of lipids from the liver, is assessed by measuring the liver triglyceride content. Hepatic steatosis is also assessed by routine histological analysis of frozen liver tissue sections stained with oil red O stain, which is commonly used to visualize lipid deposits, and counterstained with hematoxylin and eosin, to visualize nuclei and cytoplasm, respectively.

The effects of target inhibition on glucose and insulin metabolism are also evaluated in the db/db mice treated with the oligomeric compounds of the invention. Plasma glucose is measured at the start of the treatment and after 2 weeks and 4 weeks of treatment. Plasma insulin is similarly measured at the beginning of the treatment, and following 2 weeks and 4 weeks of treatment. Glucose and insulin tolerance tests are also administered in fed and fasted mice. Mice receive intraperitoneal injections of either glucose or insulin, and the blood glucose levels are measured before the insulin or glucose challenge and 15, 30, 60, 90 and 120 minutes following the injection.

To assess the metabolic rate of db/db mice treated with the oligomeric compounds of the invention, the respiratory quotient and oxygen consumption of the mice is also measured.

The db/db mice that receive treatment are further evaluated at the end of the treatment period for the effects of target inhibition on the expression genes that participate in lipid metabolism, cholesterol biosynthesis, fatty acid oxidation, fatty acid storage, gluconeogenesis and glucose metabolism. These genes include, but are not limited to, HMG-CoA reductase, acetyl-CoA carboxylase 1 and acetyl-CoA carboxylase 2, carnitine palmitoyltransferase I and glycogen phosphorylase, glucose-6-phosphatase and phosphoenolpyruvate carboxykinase 1, lipoprotein lipase and hormone sensitive lipase. mRNA levels in liver and white and brown adipose tissue are quantitated by real-time PCR as described in other examples herein, employing primer-probe sets that are generated using published sequences of each gene of interest.

Example 25

Lean Mice on a Standard Rodent Diet

C57Bl/6 mice are maintained on a standard rodent diet and are used as control (lean) animals. In a further embodiment of the present invention, the oligomeric compounds of the invention are tested in normal, lean animals. Seven-week old male C57Bl/6 mice are fed a diet with a fat content of 4% and are subcutaneously injected with one or more of the oligomeric compounds of the invention or control compounds at a dose of 25 mg/kg two times per week for 4 weeks. Saline-injected animals serve as a control. After the treatment period, mice are sacrificed and target levels are evaluated in liver, brown adipose tissue (BAT) and white adipose tissue (WAT). RNA isolation and target mRNA expression level quantitation are performed as described by other examples herein. After the treatment period, mice are sacrificed and target levels are evaluated in liver, brown adipose tissue (BAT) and white adipose tissue (WAT). RNA isolation and target mRNA expression level quantitation are performed as described by other examples herein.

To assess the physiological effects resulting from inhibition of target mRNA, the lean mice that receive treatment are further evaluated at the end of the treatment period for serum lipids, serum free fatty acids, serum cholesterol (CHOL), liver triglycerides, fat tissue triglycerides and liver enzyme levels. Hepatic steatosis, or clearing of lipids from the liver, is assessed by measuring the liver triglyceride content. Hepatic steatosis is also assessed by routine histological analysis of frozen liver tissue sections stained with oil red O stain, which is commonly used to visualize lipid deposits, and counterstained with hematoxylin and eosin, to visualize nuclei and cytoplasm, respectively.

The effects of target inhibition on glucose and insulin metabolism are also evaluated in the lean mice treated with the oligomeric compounds of the invention. Plasma glucose is measured at the start of the treatment and after 2 weeks and 4 weeks of treatment. Plasma insulin is similarly measured at the beginning of the treatment, and following 2 weeks and 4 weeks of treatment. Glucose and insulin tolerance tests are also administered in fed and fasted mice. Mice receive intraperitoneal injections of either glucose or insulin, and the blood glucose levels are measured before the insulin or glucose challenge and 15, 30, 60, 90 and 120 minutes following the injection. To assess the metabolic rate of lean mice treated with the oligomeric compounds of the invention, the respiratory quotient and oxygen consumption of the mice is also measured.

The lean mice that received treatment are further evaluated at the end of the treatment period for the effects of target inhibition on the expression genes that participate in lipid metabolism, cholesterol biosynthesis, fatty acid oxidation, fatty acid storage, gluconeogenesis and glucose metabolism. These genes include, but are not limited to, HMG-CoA reductase, acetyl-CoA carboxylase 1 and acetyl-CoA carboxylase 2, carnitine palmitoyltransferase I and glycogen phosphorylase, glucose-6-phosphatase and phosphoenolpyruvate carboxykinase 1, lipoprotein lipase and hormone sensitive lipase. mRNA levels in liver and white and brown adipose tissue are quantitated by real-time PCR as described in other examples herein, employing primer-probe sets that are generated using published sequences of each gene of interest.

It is intended that each reference referred to herein, including but not limited to publications, patents and patent applications, be incorporated by reference herein in its entirety.

What is claimed is:

1. A composition comprising a first oligomeric compound and a second oligomeric compound, wherein:
   the first oligomeric compound is capable of hybridizing with at least a portion of the second oligomeric compound and to a selected target nucleic acid;
   each of the first and the second oligomeric compounds independently comprises a contiguous sequence of from about 19 to about 23 nucleosides linked by internucleoside linking groups;
   each of the first and the second oligomeric compounds optionally comprises a phosphate group, a 3' or 5'-overhang or a conjugate group; and
   the first oligomeric compound having a plurality of modified ribofuranosyl nucleosides at defined positions, and the modified ribofuranosyl nucleosides consisting of 2'-OCH$_3$ modified nucleosides at positions 6, 7, 10, 11, 17, 18 and 19 of the first oligomeric compound counting from the terminal 5'-hybridizing nucleoside.

2. The composition of claim 1 wherein the first and the second oligomeric compounds are independently from about 19 to about 21 nucleosides in length.

3. The composition of claim 1 wherein the first and the second oligomeric compounds are each independently 19 or 20 nucleosides in length.

4. The composition of claim 1 wherein the second oligomeric compound comprises unmodified β-D-ribofuranosyl nucleosides.

5. The composition of claim 1 wherein the nucleosides of each of the first and the second oligomeric compounds are linked by phosphodiester internucleoside linking groups.

6. The composition of claim 1 wherein the nucleosides of each of the first and the second oligomeric compounds are linked by phosphorothioate internucleoside linking groups.

7. The composition of claim 1 wherein the nucleosides of each of the first and the second oligomeric compounds are independently linked by phosphorothioate or phosphodiester internucleoside linking groups.

8. The composition of claim 1 wherein the second oligomeric compound comprises modified nucleosides.

9. The composition of claim 1 wherein the second oligomeric compound comprises modified ribofuranosyl nucleosides alternating with unmodified β-D-ribofuranosyl nucleosides.

10. The composition of claim 9 wherein the modified ribofuranosyl nucleosides are either 2'-OCH$_3$ modified nucleosides or 2'-methoxyethoxy modified nucleosides.

11. The composition of claim 1 wherein the terminal 5'-hybridizing nucleoside and the terminal 3'-hybridizing nucleoside of the second oligomeric compound are unmodified β-D-ribofuranosyl nucleosides, and the nucleosides in between the terminal hybridizing nucleosides are 2'-OCH$_3$ modified nucleosides.

12. The composition of claim 1 wherein the terminal 5'-hybridizing nucleoside of the second oligomeric compound is an unmodified β-D-ribofuranosyl nucleoside, the nucleosides between the terminal 5'-hybridizing nucleoside and the terminal 3'-hybridizing nucleoside are 2'-OCH₃ modified nucleosides, and the terminal 3'-hybridizing nucleoside is a 2'-OCH₃ modified nucleoside.

13. The composition of claim 1 wherein the second oligomeric compound comprises one or more modified ribofuranosyl nucleosides independently selected from 2'-fluoro ribofuranosyl sugar moieties, 4'-thio ribofuranosyl moieties, 2'-OCH₃ ribofuranosyl sugar moieties, 2'-methoxyethoxy ribofuranosyl moieties, modified ribofuranosyl moieties having a 4'-CH₂—O-2'-bridge, and ribofuranosyl moieties having a 4'-(CH₂)₂—O-2'-bridge.

14. The composition of claim 1, wherein the second oligomeric compound comprises one or more modified ribofuranosyl nucleosides independently selected from 2'-fluoro ribofuranosyl sugar moieties and 2'-methoxyethoxy ribofuranosyl moieties.

15. The composition of claim 1 additionally comprising one or more moieties or conjugates for enhancing the activity, cellular distribution or cellular uptake of the resulting oligomeric compounds.

* * * * *

UNITED STATES PATENT AND TRADEMARK OFFICE
CERTIFICATE OF CORRECTION

PATENT NO. : 8,394,947 B2  Page 1 of 1
APPLICATION NO. : 11/569939
DATED : March 12, 2013
INVENTOR(S) : Bhat et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1493 days.

Signed and Sealed this
First Day of September, 2015

Michelle K. Lee
*Director of the United States Patent and Trademark Office*

```
                          SEQUENCE LISTING

<160> NUMBER OF SEQ ID NOS: 19

<210> SEQ ID NO 1
<211> LENGTH: 12
<212> TYPE: RNA
<213> ORGANISM: Artificial Sequence
<220> FEATURE:
<223> OTHER INFORMATION: Synthetic oligonucleotide

<400> SEQUENCE: 1
cgcgaauucg cg                                                          12

<210> SEQ ID NO 2
<211> LENGTH: 12
<212> TYPE: RNA
<213> ORGANISM: Artificial Sequence
<220> FEATURE:
<223> OTHER INFORMATION: Synthetic oligonucleotide

<400> SEQUENCE: 2
gcgcuuaagc gc                                                          12

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 3
tccgtcatcg ctcctcaggg                                                  20

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 4
gtgcgcgcga gcccgaaatc                                                  20

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide
```

```
<400> SEQUENCE: 5
atgcattctg cccccaagga                                              20

<210> SEQ ID NO 6
<211> LENGTH: 20
<212> TYPE: RNA
<213> ORGANISM: Artificial Sequence
<220> FEATURE:
<223> OTHER INFORMATION: siRNA construct

<400> SEQUENCE: 6
uccuggaucc uucaccaaug                                              20

<210> SEQ ID NO 7
<211> LENGTH: 20
<212> TYPE: RNA
<213> ORGANISM: Artificial Sequence
<220> FEATURE:
<223> OTHER INFORMATION: siRNA construct

<400> SEQUENCE: 7
cauuggugaa ggauccagga                                              20

<210> SEQ ID NO 8
<211> LENGTH: 20
<212> TYPE: RNA
<213> ORGANISM: Artificial Sequence
<220> FEATURE:
<223> OTHER INFORMATION: siRNA construct

<400> SEQUENCE: 8
auacucagaa ggugucuucu                                              20

<210> SEQ ID NO 9
<211> LENGTH: 20
<212> TYPE: RNA
<213> ORGANISM: Artificial Sequence
<220> FEATURE:
<223> OTHER INFORMATION: siRNA construct

<400> SEQUENCE: 9
agaagacacc uucugaguau                                              20

<210> SEQ ID NO 10
<211> LENGTH: 19
<212> TYPE: RNA
<213> ORGANISM: Artificial Sequence
<220> FEATURE:
<223> OTHER INFORMATION: siRNA construct

<400> SEQUENCE: 10
uuugaaaaug uugaucucc                                               19

<210> SEQ ID NO 11
<211> LENGTH: 19
<212> TYPE: RNA
<213> ORGANISM: Artificial Sequence
<220> FEATURE:
<223> OTHER INFORMATION: siRNA construct

<400> SEQUENCE: 11
ggagaucaac auuuucaaa                                               19

<210> SEQ ID NO 12
<211> LENGTH: 20
```

```
<212> TYPE: RNA
<213> ORGANISM: Artificial Sequence
<220> FEATURE:
<223> OTHER INFORMATION: siRNA construct

<400> SEQUENCE: 12 uugucucug guccuuacuu                                                    20

<210> SEQ ID NO 13
<211> LENGTH: 20
<212> TYPE: RNA
<213> ORGANISM: Artificial Sequence
<220> FEATURE:
<223> OTHER INFORMATION: siRNA construct

<400> SEQUENCE: 13
aaguaaggac cagagacaaa                                                   20

<210> SEQ ID NO 14
<211> LENGTH: 20
<212> TYPE: DNA
<213> ORGANISM: Artificial Sequence
<220> FEATURE:
<223> OTHER INFORMATION: siRNA construct
<220> FEATURE:
<221> NAME/KEY: misc_feature
<222> LOCATION: (3)..(5)
<223> OTHER INFORMATION: Bases at these positions are RNA

<400> SEQUENCE: 14
uutgtcucug guccuuacuu                                                   20

<210> SEQ ID NO 15
<211> LENGTH: 20
<212> TYPE: DNA
<213> ORGANISM: Artificial Sequence
<220> FEATURE:
<223> OTHER INFORMATION: siRNA construct
<220> FEATURE:
<221> NAME/KEY: misc_feature
<222> LOCATION: (1)..(3)
<223> OTHER INFORMATION: Bases at these positions are RNA

<400> SEQUENCE: 15
tttgtcucug guccuuacuu                                                   20

<210> SEQ ID NO 16
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 16
cgagaggcgg acgggaccg                                                    19

<210> SEQ ID NO 17
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: Bases at these positions are RNA

<400> SEQUENCE: 17
cgagaggcgg acgggaccgt t                                                 21
```

```
<210> SEQ ID NO 18
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(4)
<223> OTHER INFORMATION: Bases at these positions are RNA
<220> FEATURE:
<221> NAME/KEY: misc_feature
<222> LOCATION: (6)..(6)
<223> OTHER INFORMATION: Base at this position is RNA
<220> FEATURE:
<221> NAME/KEY: misc_feature
<222> LOCATION: (8)..(12)
<223> OTHER INFORMATION: Bases at these positions are RNA
<220> FEATURE:
<221> NAME/KEY: misc_feature
<222> LOCATION: (14)..(17)
<223> OTHER INFORMATION: Bases at these positions are RNA
<220> FEATURE:
<221> NAME/KEY: misc_feature
<222> LOCATION: (19)..(21)
<223> OTHER INFORMATION: Bases at these positions are RNA

<400> SEQUENCE: 18
ttgctctccg cctgccctgg c                                              21

<210> SEQ ID NO 19
<211> LENGTH: 19
<212> TYPE: RNA
<213> ORGANISM: Artificial Sequence
<220> FEATURE:
<223> OTHER INFORMATION: siRNA construct

<400> SEQUENCE: 19
aaguaaggac cagagacaa                                                 19
```